United States Patent
Voelker

(10) Patent No.: US 9,861,649 B2
(45) Date of Patent: Jan. 9, 2018

(54) SURFACTANT LIPIDS, COMPOSITIONS THEREOF, AND USES THEREOF

(71) Applicant: National Jewish Health, Denver, CO (US)

(72) Inventor: Dennis R. Voelker, Greenwood Village, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 14/318,303

(22) Filed: Jun. 27, 2014

(65) Prior Publication Data

US 2015/0150891 A1    Jun. 4, 2015

Related U.S. Application Data

(60) Division of application No. 13/732,929, filed on Jan. 2, 2013, now Pat. No. 8,796,243, which is a continuation of application No. 12/057,967, filed on Mar. 28, 2008, now Pat. No. 8,367,643.

(60) Provisional application No. 61/025,298, filed on Jan. 31, 2008, provisional application No. 60/908,837, filed on Mar. 29, 2007.

(51) Int. Cl.
*A61K 31/683* (2006.01)
*A61K 9/127* (2006.01)
*A61K 31/66* (2006.01)
*A61K 9/00* (2006.01)

(52) U.S. Cl.
CPC ............ *A61K 31/683* (2013.01); *A61K 9/007* (2013.01); *A61K 9/127* (2013.01); *A61K 31/66* (2013.01)

(58) Field of Classification Search
CPC .................................................. A61K 31/683
See application file for complete search history.

(56) References Cited

U.S. PATENT DOCUMENTS

| | | |
|---|---|---|
| 4,666,893 A | 5/1987 | Tsuchiya |
| 5,006,343 A | 4/1991 | Benson et al. |
| 5,725,871 A | 3/1998 | Illum |
| 8,367,643 B2 | 2/2013 | Voelker |
| 8,796,243 B2 | 8/2014 | Voelker |
| 2003/0007930 A1 | 1/2003 | Bot et al. |

(Continued)

FOREIGN PATENT DOCUMENTS

| WO | WO 2004/006847 | | 1/2004 |
|---|---|---|---|
| WO | WO2005/007169 | * | 1/2005 |

(Continued)

OTHER PUBLICATIONS

Sabroe et al., Clin Exp Allergy, 2002;32:984-989.*

(Continued)

*Primary Examiner* — San-Ming Hui
(74) *Attorney, Agent, or Firm* — Sheridan Ross P.C.

(57) ABSTRACT

The invention generally relates to methods to inhibit inflammation or pathogen infection by administering at least one anionic lipid or compositions comprising at least one anionic lipid to an individual. The invention also relates to methods to prevent or inhibit respiratory syncytial virus (RSV) infection by administering at least one anionic lipid or compositions comprising at least one anionic lipid to an individual. The invention further relates to compositions comprising randomly mixed surfactant lipids and methods to produce the compositions.

8 Claims, 50 Drawing Sheets

(56) References Cited

U.S. PATENT DOCUMENTS

| | | |
|---|---|---|
| 2005/0070477 A1 | 3/2005 | Cochrane |
| 2005/0176625 A1* | 8/2005 | Curstedt .............. C07K 14/785 514/1.5 |
| 2006/0189571 A1 | 8/2006 | Yedgar |

FOREIGN PATENT DOCUMENTS

| | | |
|---|---|---|
| WO | WO 2006/029886 | 3/2006 |
| WO | WO 2006/071796 | 7/2006 |
| WO | WO 2006/125970 | 11/2006 |

OTHER PUBLICATIONS

Asai, et al., "Treponemal glycoconjugate inhibits Toll-like receptor ligand-induced cell activation by blocking LPS-binding protein and CD 14 functions", Eur J Immunol, Nov. 2003, vol. 33, No. II, pp. 3196-3204.

Bochkov, et al., "Protective role of phospholipid oxidation products in endotoxin-induced tissue damage", Nature, Sep. 5, 2002, vol. 419, No. 6902, pp. 77-81.

Chiba, et al., "Pulmonary surfactant proteins and lipids as modulators of inflammation and innate immunity", Respirology, Jan. 2006, vol. II Suppl, pp. S2-S6.

Cochrane, "Pulmonary surfactant in allergic inflammation: new insights into the molecular mechanisms of surfactant function", Am J Physiol Lung Cell Mol Physiol., Apr. 2005, vol. 288, No. 4, pp. L608-L609.

Haeberle, et al. "Respiratory syncytial virus-induced activation of nuclear factor-kappaB in the lung involves alveolar macrophages and toll-like receptor 4-dependent pathways", J Infect Dis., Nov. 1, 2002, vol. 186, No. 9, pp. 1199-1206. Epub Oct. 11, 2002.

Hashimoto, et al., "Treponemal phospholipids inhibit innate immune responses induced by pathogen-associated molecular patterns", J Biol Chem, Nov. 7, 2003, vol. 278, No. 45, pp. 44205-44213, Epub Aug. 28, 2003.

Kneyber et al. "Bench-to-bedside review: Paediatric viral lower respiratory tract disease necessitating mechanical ventilation—should we use exogenous surfactant?" Critical Care, Dec. 2005, vol. 9, No. 6, pp. 550-555.

Kuronuma et al., "Anionic surfactant phospholipids inhibit lipopolysaccharide-induced inflammation from alveolar macrophages and U937 cells," Experimental Biology 2006 Meeting, San Francisco, CA, Apr. 1-5, 2006, p. A59 (BIOSIS abstract only).

Kurt-Jones, et al., "Pattern recognition receptors TLR4 and CD14 mediate response to respiratory syncytial virus", Nat Immunol., Nov. 2000, vol. I, No. 5, pp. 398-401.

Le Goffic, et al., "Detrimental contribution of the Toll-like receptor (TLR)3 to influenza A virus-induced acute pneumonia", PLoS Pathog, Jun. 2006,vol. 2, No. 6, p. e53, Epub Jun. 9, 2006.

Lee, et al., "Saturated fatty acid activates but polyunsaturated fatty acid inhibits Tolllike receptor 2 dimerized with Toll-like receptor 6 or 1", J Biol Chem., Apr. 23, 2004, vol. 279, No. 2, pp. 16971-16979, Epub Feb. 13, 2004.

Loughlin, et al., "The cell biology of acute childhood respiratory disease: therapeutic implications", Pediatr Clin North Am, Oct. 2006, vol. 53, No. 5, pp. 929-959, ix-x, review.

Mayo Clinic Staff, Respiratory syncytial virus (RSV), Mayo Foundation for Medical Education and Research, Jul. 29, 2011 [retrieved on Oct. 1, 2012], 8 pages. Retrieved from: www.mayoclinic.com/health/respiratory-syncytial-virus/DS00414.

Mueller, et al., "Phospholipids inhibit lipopolysaccharide (LPS)-induced cell activation: a role for LPS-binding protein", J Immunol., Jan. 15, 2005, vol. 174, No. 2, pp. 1091-1096.

Poelma, et al., "Influence of phosphatidylglycerol on the uptake of liposomes by alveolar cells and on lung function", J Appl Physiol., May 2005, vol. 98, No. 5, pp. 1784-1791, Epub Jan. 20, 2005.

Racke et al. "Toll-Like Receptors in Multiple Sclerosis," Current Topics in Microbiology and Immunology, 2009, vol. 336, pp. 155-168.

Rallabhandi, et al., "Analysis of TLR4 polymorphic variants: new insights into TLR4/MD-2/CD14 stoichiometry, structure, and signaling", J Immunol., Jul. 1, 2006, vol. 177, No. I, pp. 322-332.

Tegtmeyer, et al., "In vitro modulation of induced neutrophil activation by different surfactant preparations", Eur Respir J., Apr. 1996, vol. 9, No. 4, pp. 752-757.

Weatherill, et al., "Saturated and polyunsaturated fatty acids reciprocally modulate dendritic cell functions mediated through TLR4", J Immunol., May 1, 2005, vol. 174, No. 9, pp. 5390-5397.

Wu, et al., "Surfactant protein-A and phosphatidylglycerol suppress type IIA phospholipase A2 synthesis via nuclear factor-kappaB", Am J Respir Crit Care Med., Sep. 15, vol. 168, No. 6, pp. 692-699, Epub Jul. 25, 2003.

International Search Report for International (PCT) Patent Application No. PCT/US08/58646, dated Sep. 16, 2008.

Written Opinion for International (PCT) Patent Application No. PCT/US08/58646, dated Sep. 16, 2008.

Extended European Search Report for European Patent Application No. 08744598.7, dated Jun. 2, 2010.

* cited by examiner a  Beas2B

CONTROL RSV   RSV☐POPG OPG c  NHBE

CONTROL RSV   RSV☐POPG OPG

POPG BINDS RSV WITH HIGH AFFINITY AND SUPPRESSES IL-8 PRODUCTION FROM EPITHELIAL CELLS IN A CONCENTRATION DEPENDENT MANNER

Figure 37

SURFACTANT LIPIDS, COMPOSITIONS THEREOF, AND USES THEREOF

CROSS-REFERENCE TO RELATED APPLICATIONS

This application is a divisional Application of U.S. application Ser. No. 13/732,929, filed Jan. 2, 2013, now U.S. Pat. No. 8,796,243, which is a continuation Application of U.S. application Ser. No. 12/057,967, filed Mar. 28, 2008, now U.S. Pat. No. 8,367,643 which claims the benefit of priority under 35 U.S.C. §119(e) of U.S. Provisional Application Nos. 60/908,837, filed Mar. 29, 2007, and 61/025,298, filed Jan. 31, 2008, the entire disclosures of which are incorporated herein by reference for all purposes.

GOVERNMENT SUPPORT

This invention was made with government support under NIH Grant Nos. HL045286 and HL073907, each awarded by the National Institutes of Health. The government has certain rights in the invention.

FIELD OF THE INVENTION

The invention generally relates to methods to inhibit inflammation or pathogen infection by administering at least one anionic lipid or compositions comprising at least one anionic lipid to an individual. The invention also relates to methods to prevent or inhibit respiratory syncytial virus (RSV) infection by administering at least one anionic lipid or compositions comprising at least one anionic lipid to an individual. The invention further relates to compositions comprising randomly mixed surfactant lipids and methods to produce the compositions.

BACKGROUND OF THE INVENTION

Pulmonary surfactant was initially identified as a lipoprotein complex that reduces surface tension at the air-liquid interface of the alveolar compartment of the lung (Pattle, R. E. 1955. *Nature* 175:1125; Clements, J. A. 1957. *Proc Soc Exp Biol Med* 95:170). Pulmonary surfactant is synthesized and secreted by alveolar type II cells (King et al., 1973. *Am J Physiol* 224:788). Approximately 10% of surfactant is composed of proteins, including the hydrophilic surfactant proteins A and D (SP-A and SP-D), and the hydrophobic proteins, SP-B and SP-C (Kuroki and Voelker. 1994. *J. Biol. Chem.* 269:25943). SP-A and SP-D are now recognized to play important roles in innate immunity (Sano and Kuroki. 2005. *Mol Immunol* 42:279). SP-A and SP-D directly interact with various microorganisms and pathogen-derived components (Lawson and Reid. 2000. *Immunol Rev* 173:66). Moreover, by associating with cell surface pattern-recognition receptors, SP-A and SP-D regulate inflammatory cellular responses such as the release of lipopolysaccharide (LPS)-induced proinflammatory cytokines (Sano et al., 1999. *J. Immunol.* 163:387). LPS, derived from Gram-negative bacteria, is a potent stimulator of inflammation (O'Brien et al., 1980. *J Immunol* 124:20; Ulevitch and Tobias. 1995. *Annu Rev Immunol* 13:437). LPS molecules are engaged by the plasma LPS binding protein (LBP) (Wright et al., 1990. *Science* 249:1431) and transferred to CD14, a glycosylphosphatidylinisitol (GPI)-anchored protein, abundantly expressed on macrophages. LPS responses are dependent on the peripherally associated plasma membrane protein MD-2 (Nagai et al. 2002. *Nat Immunol* 3:667). and the membrane-spanning complex formed by toll-like receptor (TLR) 4 (Poltorak et al., 1998. *Science* 282:2085), through which signaling is propagated. TLRs activate four intracellular protein kinase cascades, the IB kinase (IKK)/NF-kB transcription factor cascade, the extracellular signal-regulated kinase (ERK), c-Jun NH2-terminal kinase (JNK) and p38 mitogen-activated protein kinase (MAPK) cascades, leading to the induction of many key cytokine genes that are essential for the innate immune response (Takeda et al., 2003. *Annu Rev Immunol* 21:335; Medzhitov, R. 2001. *Nat Rev Immunol* 1:135; Barton and Medzhitov. 2003. *Science* 300:1524). At least one important function of SP-A and SP-D is to suppress the inflammatory response of the lung to LPS.

By weight, approximately 90% of surfactant consists of lipids. Although the lipid composition varies in different species, its major component is phosphatidylcholine (PC) (70-80%) of which nearly 80% is disaturated, consisting primarily of dipalmitoyl-phosphatidylcholine (DPPC). In addition, pulmonary surfactant contains variable amounts of phosphatidylglycerol (PG) (7-18%), phosphatidylinositol (PI) (2-4%) and phosphatidylethanolamine (PE) (2-3%) (Veldhuizen et al. 1998. *Biochem Biophys Acta* 1408:90). In contrast to PC, more than 50% of PG is unsaturated in many species, and in humans there is little or no disaturated PG (Schmidt et al., 2002. *Am J Physiol Lung Cell Mol Physiol* 283:1079; Wright et al., 2000. *J Appl Physiol* 89:1283). The functions of the minor phospholipid and the neutral lipid components of surfactant are largely unclear and there is a need in the art for further information regarding the roles of these components.

Previous work has provided some evidence that specific phospholipids can modulate inflammation. Oxidized phospholipid inhibits LPS-induced inflammatory responses in human umbilical-vein endothelial cells (Bochkov et al., 2002. *Nature* 419:77). Dioleoyl-phosphatidylglycerol (DOPG) inhibits phospholipase A2 secretion via a down-regulation of NF-kB activation in guinea pig macrophages (Wu et al. 2003. *Am J Respir Crit Care Med* 168:692). Treponemal membrane phosphatidylglycerol inhibits LPS-induced immune responses from macrophages by inhibiting the binding of biotinylated LPS to LBP and blocked the binding of soluble CD14 (sCD14) to LPS (Hashimoto et al., 2003. *J Biol Chem* 278:44205). Cardiolipin, PG and PI exhibit an inhibitory effect on LPS-induced TNF-α production by human macrophages, most likely by a blockade of the binding of LPS aggregates to LBP (Mueller et al., 2005. *J Immunol* 172:1091). However, very few reports have focused on the potential anti-inflammatory roles of surfactant phospholipids on either alveolar or non-alveolar macrophages. Moreover, the relationship between surfactant phospholipids and CD14 or other pattern recognition receptors has not been clearly identified.

Various studies have made connections between surfactant PG content and disease. For example, in idiopathic pulmonary fibrosis patients, some groups reported decreased unsaturated PG in surfactant (Veldhuizen et al., 1998, *Biochem Biophys Acta* 1408:90; Honda et al., 1988, *Lung* 166:293; and Saydain et al., 2002, *Am J Resp Crit Care Med* 166:839). In another disease, ARDS, Schmidt et. al. have reported significant reduction in the unsaturated PG recovered in BALF (Schmidt et al., 2001, *Am J Respir Crit Care Med* 163:95). The issues of cause and effect in the above diseases remain unclear.

LPS is a major cause of acute lung injury (ALI) and acute respiratory distress syndrome (ARDS) (Atabai and Matthay. 2002. *Thorax* 2002; Rubenfeld et al., 2005. *N Engl J Med*

353:1685). ALI/ARDS is a life-threatening condition in which inflammation of the lungs and accumulation of fluid in the alveoli leads to low blood oxygen levels. Over a period of 25 years the annual incidence of ALI/ARDS is 335,000, with 147,000 deaths per year. The most common risk factor for ALI was severe sepsis with a suspected pulmonary source (46%), followed by severe sepsis with a suspected nonpulmonary source (33%).

Given the severity of symptoms associated with many inflammatory conditions, including those affecting the respiratory system, there is a continued need for agents useful in controlling inflammation and thereby preventing and/or treating conditions or diseases associated with inflammation.

SUMMARY OF THE INVENTION

One aspect of the invention relates to a method to inhibit inflammation or pathogen infection, comprising administering to an individual who has, or is at risk of developing said inflammation or pathogen infection, an amount of at least one anionic lipid or related compound, wherein the amount of the anionic lipid or related compound is effective to inhibit said inflammation or pathogen infection, and wherein the anionic lipid has the following characteristics: a hydrophobic portion, a negatively charged portion, and an uncharged, polar portion.

In some embodiments, the anionic lipid or related compound is selected from the group consisting of: unsaturated phosphatidylglycerol, unsaturated phosphatidylinositol, saturated short chain phosphatidylglycerol, saturated short chain phosphatidylinositol, anionic sphingolipid, anionic glycerolipid, unsaturated lyso-phosphatidylglycerol, saturated lyso-phosphatidylglycerol, unsaturated lyso-phosphatidylinositol, and saturated lyso-phosphatidylinositol, or a derivative thereof.

In some embodiments, the anionic lipid is selected from the group consisting of: an unsaturated phosphatidylglycerol, an unsaturated phosphatidylinositol, a saturated short chain phosphatidylglycerol, and a saturated short chain phosphatidylinositol, or a derivative of the anionic lipid.

In some embodiments, the inflammation or pathogen infection is associated with a toll-like receptor (TLR) selected from the group consisting of: TLR1, TLR2, TLR3, TLR4, TLR6, TLR7, TLR8, and TLR10.

In some embodiments, the inflammation or pathogen infection is associated with a toll-like receptor (TLR) selected from the group consisting of: TLR1, TLR2, TLR3, TLR6, TLR7, TLR8, and TLR10.

In some embodiments, the individual has a bacterial infection associated with TLR1.

In some embodiments, the individual has an infection, condition, or disease associated with TLR2 selected from the group consisting of: cytomegalovirus infection, herpes simplex virus infection, measles, a protozoan infection, a fungal infection, and Varicella zoster infection.

In some embodiments, the individual has an infection, condition, or disease associated with TLR3 selected from the group consisting of: a viral infection (such as rhinovirus infection or parainfluenza virus infection) and a cancer.

In some embodiments, the individual has an infection, condition, or disease associated with TLR6 selected from the group consisting of: a bacterial infection, a protozoan infection and a fungal infection.

In some embodiments, the individual has an infection, condition, or disease associated with TLR7 selected from the group consisting of: an autoimmune disease, a cancer, and a viral infection.

In some embodiments, the viral infection is selected from the group consisting of: human immunodeficiency virus infection, rhinovirus infection, parainfluenza virus infection, human parechorvirus infection, influenza infection, papilloma virus infection, and Varicella zoster infection.

In some embodiments, the individual has an infection, condition, or disease associated with TLR8 selected from the group consisting of: autoimmune disease, basal cell carcinoma, Bowen's disease, condyloma, genital warts, human immunodeficiency virus (HIV), rhinovirus, parainfluenza virus, Human parechovirus, melanoma, and mollusca contagiosa.

In some embodiments, the individual has a respiratory disorder. In some embodiments, the respiratory disorder is selected from the group consisting of: adult respiratory distress syndrome (ARDS), acute lung injury (ALI), viral infection associated with asthma, chronic obstructive pulmonary disease (COPD), pneumonia, bronchitis, tuberculosis, reactive airway disease syndrome, interstitial lung disease, rhinitis, and parasitic lung disease.

Another aspect of the invention relates to a method to prevent or inhibit viral infection, comprising administering to an individual who has, or is at risk of developing a viral infection, at least one anionic lipid or related compound, wherein the amount of the anionic lipid or related compound is effective to prevent or inhibit said viral infection, and wherein the anionic lipid has the following characteristics: a hydrophobic portion, a negatively charged portion, and an uncharged, polar portion.

In some embodiments, the anionic lipid or related compound is selected from the group consisting of: unsaturated phosphatidylglycerol, unsaturated phosphatidylinositol, saturated short chain phosphatidylglycerol, saturated short chain phosphatidylinositol, anionic sphingolipid, anionic glycerolipid, unsaturated lyso-phosphatidylglycerol, saturated lyso-phosphatidylglycerol, unsaturated lyso-phosphatidylinositol, and saturated lyso-phosphatidylinositol, or a derivative thereof.

In some embodiments, the anionic lipid is selected from the group consisting of: an unsaturated phosphatidylglycerol, an unsaturated phosphatidylinositol, a saturated short chain phosphatidylglycerol, and a saturated short chain phosphatidylinositol, or a derivative of the anionic lipid.

Another aspect of the invention relates to a method to prevent or inhibit respiratory syncytial virus (RSV) infection, comprising administering to an individual who has, or is at risk of developing a viral infection, at least one anionic lipid or related compound, wherein the amount of the anionic lipid or related compound is effective to prevent or inhibit said RSV infection, and wherein the anionic lipid has the following characteristics: a hydrophobic portion, a negatively charged portion, and an uncharged, polar portion.

In some embodiments, the anionic lipid or related compound is selected from the group consisting of: unsaturated phosphatidylglycerol, unsaturated phosphatidylinositol, saturated short chain phosphatidylglycerol, saturated short chain phosphatidylinositol, anionic sphingolipid, anionic glycerolipid, unsaturated lyso-phosphatidylglycerol, saturated lyso-phosphatidylglycerol, unsaturated lyso-phosphatidylinositol, and saturated lyso-phosphatidylinositol, or a derivative thereof.

In some embodiments, the anionic lipid is selected from the group consisting of: an unsaturated phosphatidylglycerol, an unsaturated phosphatidylinositol, a saturated short chain phosphatidylglycerol, and a saturated short chain phosphatidylinositol, or a derivative of the anionic lipid.

In some embodiments, the individual is a neonatal infant.

In some embodiments, the anionic lipid or related compound is administered to the infant prior to any indication of infection with RSV.

In some embodiments, the anionic lipid or related compound is administered to the infant subsequent to identification of a symptom of or confirmation of infection of the infant with RSV.

In some embodiments, the anionic lipid or related compound is phosphatidylglycerol, or a derivative thereof.

In some embodiments, the anionic lipid or related compound is palmitoyl-oleoyl-phosphatidylglycerol (POPG), or a derivative thereof.

In some embodiments, the anionic lipid or related compound is dimyristoyl-phosphatidylglycerol (DMPG), or a derivative thereof.

In some embodiments, the anionic lipid or related compound is unsaturated phosphatidylinositol, or a derivative thereof.

In some embodiments, the anionic lipid or related compound is an anionic sphingolipid or a derivative thereof.

In some embodiments, the anionic lipid or related compound is an anionic glycerolipid or a derivative thereof.

In some embodiments, the anionic lipid or related compound is an unsaturated or saturated lyso-phosphatidylglycerol, or a derivative thereof.

In some embodiments, the anionic lipid or related compound is an unsaturated or saturated lyso-phosphatidylinositol or a derivative thereof.

In some embodiments, the anionic lipid or related compound is administered as a homogeneous lipid preparation.

In some embodiments, the anionic lipid or related compound is administered as a composition comprising a homogeneous lipid preparation of the anionic lipid or related compound.

In some embodiments, the anionic lipid or related compound is administered as a composition comprising a preparation of randomly mixed surfactant lipids combined with a homogeneous lipid preparation of the anionic lipid or related compound.

In some embodiments, the anionic lipid or related compound is administered as a preparation of randomly mixed surfactant lipids, wherein the anionic lipid or related compound comprises at least about 50% of the total lipids in said randomly mixed surfactant lipids.

In some embodiments, the anionic lipid or related compound is administered to the respiratory tract of the individual.

Another aspect of the invention relates to a method to inhibit inflammation, comprising administering to an individual who has, or is at risk of developing said inflammation, a composition comprising at least one anionic lipid or related compound, wherein the anionic lipid or related compound is effective to inhibit said inflammation, and wherein the anionic lipid has the following characteristics: a hydrophobic portion, a negatively charged portion, and an uncharged, polar portion; and wherein the composition is selected from the group consisting of: a homogeneous lipid preparation consisting of the anionic lipid or related compound; a composition comprising a homogeneous lipid preparation of the anionic lipid or related compound and at least one agent for the treatment of inflammation; a composition comprising a preparation of randomly mixed surfactant lipids combined with a homogeneous lipid preparation of the anionic lipid or related compound; and a preparation of randomly mixed surfactant lipids, wherein the anionic lipid or related compound comprises at least about 50% of the total lipids in said randomly mixed surfactant lipids.

In some embodiments, the anionic lipid or related compound is selected from the group consisting of: unsaturated phosphatidylglycerol, unsaturated phosphatidylinositol, saturated short chain phosphatidylglycerol, saturated short chain phosphatidylinositol, anionic sphingolipid, anionic glycerolipid, unsaturated lyso-phosphatidylglycerol, saturated lyso-phosphatidylglycerol, unsaturated lyso-phosphatidylinositol, and saturated lyso-phosphatidylinositol, or a derivative thereof.

In some embodiments, the anionic lipid is selected from the group consisting of: an unsaturated phosphatidylglycerol, an unsaturated phosphatidylinositol, a saturated short chain phosphatidylglycerol, and a saturated short chain phosphatidylinositol, or a derivative of the anionic lipid.

In some embodiments, the composition is a preparation of randomly mixed surfactant lipids combined with a homogeneous lipid preparation of the anionic lipid or related compound.

In some embodiments, the composition is a homogeneous lipid preparation of the anionic lipid or related compound and at least one additional agent for treating inflammation.

Another aspect of the invention relates to a method to produce a surfactant composition, comprising (a) providing a substantially homogeneous lipid preparation of at least one anionic lipid or related compound, wherein the anionic lipid has the following characteristics: a hydrophobic portion, a negatively charged portion, and an uncharged, polar portion; and (b) adding the preparation of (a) to a preparation of randomly mixed surfactant lipids.

In some embodiments, the preparation of (a) is in aqueous solution.

In some embodiments, the preparation of (b) is in aqueous solution.

In some embodiments, the preparation is gently mixed to avoid significant fusion or intermixing of lipids between lipid bilayers or micelles in (a) and (b).

In some embodiments, the lipids in the preparation of (a) comprise at least 1% of the total lipids in the composition.

In some embodiments, the anionic lipid or related compound is phosphatidylglycerol, or a derivative thereof.

In some embodiments, the anionic lipid or related compound is palmitoyl-oleoyl-phosphatidylglycerol (POPG), or a derivative thereof.

In some embodiments, the anionic lipid or related compound is dimyristoyl-phosphatidylglycerol (DMPG), or a derivative thereof.

In some embodiments, the anionic lipid or related compound is unsaturated phosphatidylinositol, or a derivative thereof.

In some embodiments, the anionic lipid or related compound is an anionic sphingolipid or a derivative thereof.

In some embodiments, the anionic lipid or related compound is an anionic glycerolipid or a derivative thereof.

In some embodiments, the anionic lipid or related compound is an unsaturated or saturated lyso-phosphatidylglycerol, or a derivative thereof.

In some embodiments, the anionic lipid or related compound is an unsaturated or saturated lyso-phosphatidylinositol or a derivative thereof.

Another aspect of the invention relates to a surfactant composition comprising a mixture of (a) a preparation of randomly mixed surfactant lipids and (b) one or more substantially homogeneous lipid preparations of at least one anionic lipid or related compound, wherein the anionic lipid has the following characteristics: a hydrophobic portion, a negatively charged portion, and an uncharged, polar portion; wherein the preparation of (b) is added to the preparation of (a) to form a composition in which there is no significant fusion or intermixing of lipids between lipid bilayers of (a) and (b).

In some embodiments, the lipids in the preparation of (b) comprise at least 1% of the total lipids in the composition.

In some embodiments, the anionic lipid or related compound is phosphatidylglycerol, or a derivative thereof.

In some embodiments, the anionic lipid or related compound is palmitoyl-oleoyl-phosphatidylglycerol (POPG), or a derivative thereof.

In some embodiments, the anionic lipid or related compound is dimyristoyl-phosphatidylglycerol (DMPG), or a derivative thereof. In some embodiments, the anionic lipid or related compound is unsaturated phosphatidylinositol, or a derivative thereof.

In some embodiments, the anionic lipid or related compound is an anionic sphingolipid or a derivative thereof.

In some embodiments, the anionic lipid or related compound is an anionic glycerolipid or a derivative thereof.

In some embodiments, the anionic lipid or related compound is an unsaturated or saturated lyso-phosphatidylglycerol, or a derivative thereof.

In some embodiments, the anionic lipid or related compound is an unsaturated or saturated lyso-phosphatidylinositol or a derivative thereof.

Another aspect of the invention relates to a lipid composition comprising randomly mixed surfactant lipids, wherein at least 50% of the total lipids in the composition is comprised of one or more anionic lipids or related compounds, wherein the anionic lipid has the following characteristics: a hydrophobic portion, a negatively charged portion, and an uncharged, polar portion.

In some embodiments, the anionic lipid or related compound is phosphatidylglycerol, or a derivative thereof.

In some embodiments, the anionic lipid or related compound is palmitoyl-oleoyl-phosphatidylglycerol (POPG), or a derivative thereof.

In some embodiments, the anionic lipid or related compound is dimyristoyl-phosphatidylglycerol (DMPG), or a derivative thereof.

In some embodiments, the anionic lipid or related compound is unsaturated phosphatidylinositol, or a derivative thereof.

In some embodiments, the anionic lipid or related compound is an anionic sphingolipid or a derivative thereof.

In some embodiments, the anionic lipid or related compound is an anionic glycerolipid or a derivative thereof.

In some embodiments, the anionic lipid or related compound is an unsaturated or saturated lyso-phosphatidylglycerol, or a derivative thereof.

In some embodiments, the anionic lipid or related compound is an unsaturated or saturated lyso-phosphatidylinositol or a derivative thereof.

BRIEF DESCRIPTION OF THE FIGURES

FIG. 37 shows that POPG binds RSV with high affinity and specificity, and inhibits IL-8 production from epithelial cells in a concentration-dependent manner.

DESCRIPTION OF THE INVENTION

Figure 1:
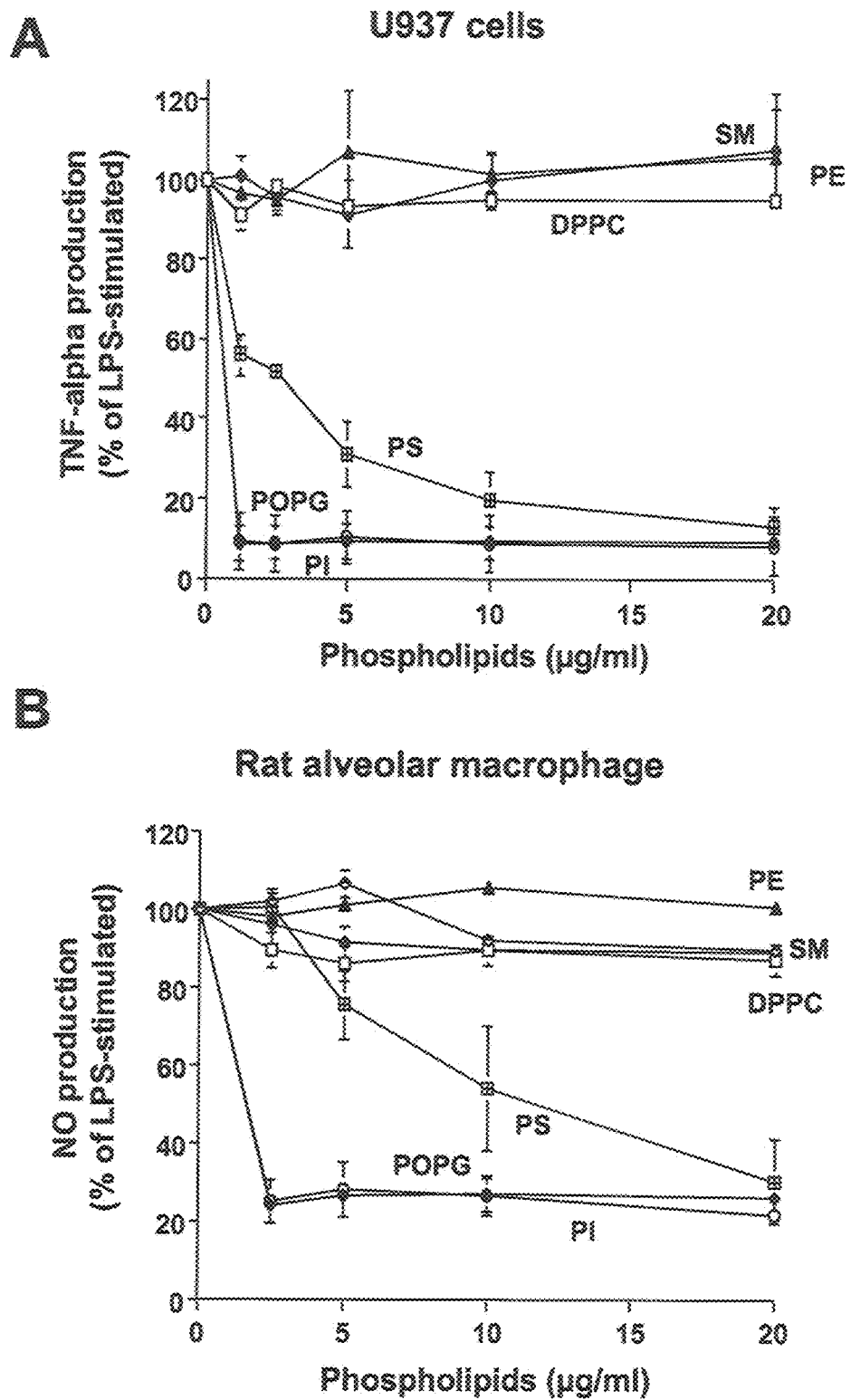
FIG. 1. Anionic phospholipids inhibit inflammatory mediator production induced by LPS. Liposomes composed of sphingomyelin (SM), phosphatidylethanolamine (PE) dipalmitoyl-phosphatidylcholine ((DPPC), phosphatidylserine (PS), palmitoyl-oleoyl-phosphatidylglycerol (POPG) and phosphatidylinositol (PI) were formed by bath-sonication for 30 min at room temperature. LPS (10 ng/ml) and different concentrations of phospholipids were added to monolayer cultures of differentiated U937 cells (A), or primary rat alveolar macrophages (B). At 6 h after stimulation, media were collected and secreted TNF-α levels were determined in U937 cultures. NO production was determined 24 h after stimulating rat alveolar macrophages. LPS stimulation in the absence of phospholipid was set as 100%. The data shown are the means±S.E. from three separate experiments with duplicate samples in each experiment. The average TNF-α production upon LPS stimulation was (8.0±0.54 ng/ml). The average NO production upon LPS stimulation was 12.17±0.27 μM.

The present invention generally relates to the discovery by the present inventor that particular surfactant phospholipids, and particularly, anionic phospholipids, are potent inhibitors of inflammation. Specifically, the inventor has discovered that unsaturated phosphatidylglycerols (PGs or PtdGro), including, but not limited to palmitoyl-oleoyl-phosphatidylglycerol (POPG), unsaturated phosphatidylinositols (PIs or PtdIns), and selected short chain saturated phospholipids, including, but not limited to, short chain saturated PGs (e.g., dimyristoyl-phosphatidylglycerol (DMPG) or 14:0/14:0-PtdGro), are potent inhibitors of inflammation. In addition, the present invention relates to the extension of this discovery to the use of a class of lipids for the prevention or inhibition of inflammation. In particular, in addition to the above-described lipids, the invention relates to the use of any anionic lipid that has the following characteristics: (1) has a hydrophobic portion; (2) has a negatively charged portion; and (3) has an uncharged, polar portion, for the prevention or inhibition of inflammation. Such lipids include, but are not limited to, the above-mentioned phospholipids, anionic sphingolipids, anionic glycerolipids (e.g., anionic diglycerides from plants, such as SQV-diglycerides). In addition, the invention relates to the use of compounds closely related to unsaturated PG and unsaturated PI, and particularly lyso-PG and lyso-PI, including, but not limited to, saturated or unsaturated lyso-PG, and saturated or unsaturated lyso-PI, for the prevention and or inhibition of inflammation.

The inhibitory activity of the lipids and compounds of the invention can be attributed to activation of the specific toll receptors, TLR1, TLR2, TLR3, TLR6, TLR7, and TLR8, as well as TLR4, and in some embodiments, TLR10. Accordingly, the present invention relates to homogeneous preparations of these anionic lipids and related compounds, as well as various compositions comprising these anionic lipids and related compounds, and the use of these anionic lipids and related compounds and/or compositions thereof, for the prevention and/or treatment of inflammation, and particularly inflammation associated with the activation of TLR1, TLR2, TLR3, TLR4, TLR6, TLR7, TLR8, TLR10, and infections, conditions and diseases related to such activation.

The present invention also relates to the use of these anionic lipids and related compounds and/or compositions containing such anionic lipids and related compounds, to prevent and/or treat viral infections, and more particularly, certain respiratory infections, including, but not limited to, respiratory syncytial virus (RSV) infection.

The present invention also relates to special formulations of pulmonary surfactant for the enhancement of anti-inflammatory and anti-viral properties of surfactant, which can be used in any of the methods described herein and in the treatment of any inflammatory condition or disease and/or infection by a pathogen. These formulations are described below.

Unsaturated PtdGro is a normal constituent of human pulmonary surfactant. However, when tested as an isolated lipid preparation, the inventor demonstrates herein that PtdGro lipid suppresses inflammation, which is attributable to activation of TLR1, TLR2, TLR3, TLR4, TLR6, TLR7, and TLR8. The lipid also suppresses viral infection (e.g., RSV) due to TLR4/CD14 ligation and viral inflammation due to TLR3. Without being bound by theory, the inventor also believes that TLR10 may be a target of this inhibitory action.

More specifically, the inventor first examined the anti-inflammatory effect of surfactant phospholipids upon LPS-induced inflammation in macrophages (see Example 1). The purpose of this investigation was to determine 1) if minor surfactant lipids can act as LPS antagonists, 2) the molecular specificity of that antagonism, and 3) the mechanism of surfactant lipid mediated antagonism. In particular, the inventor demonstrated that anionic surfactant lipids play an important role in regulating pulmonary inflammation in response to LPS. The inventor's data provides strong evidence that POPG and PI, which are minor components of pulmonary surfactant, effectively inhibit LPS-induced inflammatory responses by U937 cells, primary rat alveolar macrophages and primary human alveolar macrophages. POPG and PI block LPS-induced phosphorylation of MAPKs and IkBα. These anionic lipids also prevent LPS induced degradation of IkBα, and MKP-1 expression, indicating that LPS signaling is not transmitted from TLR4. Consistent with this latter interpretation is the finding that POPG and PI also inhibit the binding of BODIPY-LPS to RAW264.7 cells. These findings identify an intrinsic system within the lung that suppresses inflammation and protects the delicate alveolar compartment from damage. The action of POPG and PI appears complementary to that of the pulmonary surfactant collectins, SP-A and SP-D, that also function to suppress inflammation within the lung (Wright, J. R. 2005, *Nat Rev Immunol* 5:58). By maintaining a basal suppressive state within the conducting and gas exchange regions of the organ, the lung remains largely unresponsive to low level exposure to airborne particulate matter that contains LPS. This type of suppressive state ensures that the alveolar epithelium at the interface with the external environment is not chronically inflamed, as a consequence of repeated minor exposure to inflammatory stimuli.

The LPS antagonism of POPG and PI demonstrated herein is specific, since other phospholipids such as PC, PE and SM are without effect. In comparison to POPG and PI, another anionic phospholipid, PS, is only a weak antagonist of LPS action. Moreover, even within the class of PGs there is specificity of action. DPPG and DSPG failed to antagonize LPS action upon macrophages, and among shorter chain saturated PGs, only DMPG acted as an effective antagonist. Human surfactant is highly enriched in POPG but contains no DMPG.

The present inventor's findings identify an important role for the minor acidic lipids of pulmonary surfactant in suppressing inflammation within the alveolar compartment of the lung that is induced by activation of TLR4. The site of action of PtdGro and PtdIns appears to be at the cell surface of macrophages, and perhaps other cells where the recognition of LPS by TLR4 is disrupted.

Example 2 provides a demonstration of some of the mechanisms by which the surfactant lipids act. Specifically, the inventor provides evidence herein that two anionic pulmonary surfactant phospholipids (POPG and PI) inhibit LPS-induced inflammatory responses from macrophages. It is demonstrated that POPG and PI bind to CD14 and form stable complexes detectable by ELISA. The interactions between POPG and CD14 disrupt CD14 binding to LPS and LBP. In addition to binding CD14, POPG also binds to MD-2. The POPG binding to MD-2 disrupts the interaction of this protein with TLR4. From these data, it is concluded that CD14 is a common ligand for PI and POPG antagonism of LPS action. In addition, the antagonism of LPS-induced inflammation by POPG is enhanced by interaction of this lipid with MD-2.

The crystal structure of mouse CD14 demonstrates the protein has LPS binding pockets at its N-terminus (Kim et al., 2005, *J Biol Chem* 280:11347). Four LPS binding regions have been identified within the $NH_2$-terminal 65 residues of CD 14 (Cunningham et al., 2000, *J Immunol* 164:3255). Monoclonal antibodies biG14 and MEM-18 bind to regions corresponding to the third and fourth pockets, and block LPS binding. Both POPG and PI strongly bind to CD14 and the monoclonal antibodies biG14 and MEM-18 compete for the binding of CD14 to these lipids. These data demonstrate significant overlap between the LPS and anionic surfactant phospholipid binding sites. From single-residue mutation experiments, charge reversal mutations within binding regions 3 and 4 had the greatest effect on LPS binding (Cunningham et al., supra). Since the hydrophilic portion of LPS is also negatively charged, the anionic phospholipids may compete with LPS by interfering with charge dependent interactions with CD14. Kim et al suggested the hydrophobic portion of LPS binds to the first and second $NH_2$-terminal pockets since these are the only hydrophobic surfaces large enough to accommodate acyl portions of LPS (Kim et al., supra). POPG and DMPG bind to CD14 and antagonize the actions of LPS. In contrast DPPG, dilauroyl-PG and dioctanoyl-PG fail to antagonize LPS action. The molecular species specificity of PG action demonstrate that fatty acid structure is also an important determinant of the interaction of phospholipids with the hydrophobic pockets in CD 14.

Mueller et al. reported that LBP was a target for the inhibitory function of anionic phospholipids including PG, PI and cardiolipin (Mueller et al., 2005, *J Immunol* 172:109). However, the present inventors could only demonstrate that POPG attenuates the binding of LBP to CD14. Furthermore, in serum free media without LBP, anionic phospholipids still inhibit LPS-induced inflammation. Thus, the present inventor's data show that PI and POPG can antagonize LPS action by mechanisms other than interference with LBP-LPS interactions. LPS also binds to MD-2 without a requirement for either LBP or CD14 (Viriyakosol et al., 1995, *J Biol Chem* 270:361). MD-2 binds to the extracellular TLR4 domain and a complex of MD-2 and TLR4, but not TLR4 alone can interact with LPS (Hyakushima et al., 2004, *J Immunol* 173:6949). POPG binds to MD-2 with high affinity. Interestingly, the interaction of POPG with MD-2 inhibits the binding of the protein to TLR4 and subsequently antagonizes LPS action. The interaction between POPG and MD-2 is specific since PI fails to bind the protein. Previous protein sequence analysis has identified MD-2 as a protein related to fungal PG and PI binding and transfer proteins (Inohara et al., 2002, *Trends Biochem Sci* 27:219). According to Gioannini et al, the most efficient response to endotoxin occurs when it is sequentially transferred from LBP to CD14 and finally MD-2 to engage TLR4 dependent intracellular signaling (Gioannini et al., 2004, *Proc Natl Acad Sci USA* 101:4186). PI interferes with the interactions between LPS and CD14 but POPG acts at multiple steps of protein-LPS recognition. Thus, POPG appears more broadly directed at multiple pattern recognition proteins.

Collectively, the inventor's data described herein demonstrate that the anionic pulmonary surfactant lipids play a crucial role in suppressing inflammatory responses in the delicate alveolar compartments of the lung. Unnecessary and persistent inflammation in this region is likely to compromise the efficiency of $O_2/CO_2$ exchange. The lung appears uniquely poised between suppression and activation of inflammatory responses, with the basal homeostatic condition favoring suppression. This suppression depends on the lipids, PG and PI, and the pulmonary collectins, SP-A and SP-D. The presence of multiple surfactant components with these activities, provides a means of expanding the repertoire of pathogen derived pro-inflammatory components that can be antagonized during routine daily exposure. The net result appears to maintain the lung in a quiescent state until a critical threshold is reached that finally allows inflammation to proceed. The loss of control of inflammation can lead to septic shock syndrome, acute lung injury and acute respiratory distress syndrome (ARDS), which remain untreatable diseases (Rubenfeld et al., 2005, *N Engl J Med* 353:1685). The inventor's findings that anionic surfactant phospholipids regulate the innate immune system and directly interact with receptors are important for understanding fundamental mechanisms of host defense in the lung. These current findings cause the inventor to propose herein that exogenous supplementation of the bronchoalveolar compartment of the lung with anionic lipids will provide a means of controlling excessive inflammation within this organ.

The present inventor has also demonstrated that the anionic surfactant phospholipids described herein are capable of inhibiting the activity of other TLRs than TLR4 in a specific manner. In particular, when tested as an isolated lipid preparation, PtdGro lipid suppresses inflammation attributable to activation of TLR1, TLR2, TLR3TLR4, TLR6, TLR7 and TLR8 (see Example 3). Inflammation attributable to activation of other TLRs, including TLR5, TLR9 and TLR11, are apparently not affected by the phospholipids that form the basis of this invention. TLR10 may be included among the list of TLRs which are inhibited by the method of the invention, for the purposes of this disclosure.

Accordingly, methods that target inflammation associated with TLR1, TLR2, TLR3 TLR4, TLR6, TLR7, TLR8, and/or TLR10, and infections, conditions or diseases associated with these TLRs, are embodiments of the invention. These TLRs have been associated, for example, with various bacterial infections, protozoan and fungal infections, viral infections (e.g., Cytomegalovirus infection, Herpes simplex virus infection, measles, Varicella-zoster virus infection, HIV infection, rhinovirus infection, parainfluenza virus infection, Human parechovirus infection, influenza type A viral infection, Papilloma virus infection), cancer (including, but not limited to, melanoma and basal cell carcinoma), autoimmune diseases, Bowen's disease, condyloma, genital warts, and mollusca contagiosa.

The inventor also provides evidence herein that the particular phospholipid preparations of the invention suppress infection by respiratory syncytial virus (RSV), e.g., due to TLR4/CD14 ligation (not associated with LBP), and viral inflammation due to TLR3. The inventor's results in RSV indicate that preparations of the lipids described herein (e.g., any of the anionic lipids and related compounds, including, but not limited to, unsaturated PGs, unsaturated PIs, certain saturated short chain PGs or PIs, anionic sphingolipids, anionic glycerolipids, saturated or unsaturated lyso-PG, and/or saturated or unsaturated lyso-PI, can be used alone or in combination with other lipids or agents, and/or as a supplement to conventional surfactant preparations, to prevent and/or treat RSV infection. In addition, such preparations can be used to prevent and/or treat other inflammatory conditions, including pulmonary infections and disorders, including in infants, children and adults, such conditions including, but not limited to, adult respiratory distress syndrome (ARDS), acute lung injury (ALI), viral infection associated with asthma, chronic obstructive pulmonary disease (COPD), pneumonia, bronchitis, tuberculosis, reactive airway disease syndrome, interstitial lung disease, rhinitis, and parasitic lung disease.

Moreover, the inventor has demonstrated that surface dilution and randomization of POPG within a single vesicle of lipids significantly diminishes the potency of the lipid as an antagonist of LPS action. Specifically, the efficacy of PtdGro as an anti-inflammatory agent was tested after mixture with pulmonary surfactant lipids and hydrophobic proteins. Under conditions where PtdGro is randomly mixed with surfactant lipids, such as it would be provided using most commercially available preparations of surfactant, its effectiveness was greatly reduced. The inventor's data showed that in order to approximate the activity of POPG alone observed in other experiments, randomized POPG (i.e., POPG randomly mixed with surfactant lipids) must constitute nearly 50% of the total lipid present in a surfactant lipid-containing vesicle. In contrast, admixture of pure POPG vesicles and randomized surfactant lipid vesicles had essentially no detrimental effect upon the activity of POPG as an LPS antagonist. This result also indicated that the combination of pure POPG vesicles with surfactant lipid vesicles does not result in significant fusion and intermixing of lipids between vesicle bilayers. This important result indicates that the introduction of POPG vesicles into the surfactant environment of the alveolar compartment of the lung is expected to yield physical forms of the lipid that are capable of potently antagonizing LPS action. Accordingly, the inventor has shown that supplementation of human surfactant lipids with POPG liposomes improves LPS antagonism both in vivo and in vitro. The in vitro experiments demonstrate that segregated populations of POPG liposomes are the most effective antagonists of LPS action. It is not yet known whether POPG can exist in segregated domains within the surfactant monolayer or within the alveolar hypophase present in the lung. However, biophysical studies provide good evidence that DPPC can exist in distinct domains in the surfactant layer and thus it is reasonable to conclude that POPG could also be present in segregated domains (Nag et al., 1998, *Biophys J* 74:2983). The in vivo studies performed with intra-tracheal administration of POPG strongly support the embodiments of the invention related to the provision of supplemental POPG to effectively attenuate lung inflammation in vivo, and are consistent with a model in which the lipid remains in a segregated state.

Indeed, this discovery by the inventor likely accounts for the reason that the presence of PtdGro in commercial surfactant preparations (including those derived from biological sources, such as porcine or bovine surfactant) has not, to the inventor's knowledge, had any demonstrable effect as an anti-inflammatory or anti-viral agent. However, as demonstrated herein, if PtdGro is first prepared as a separate homogeneous liposomal suspension in aqueous solution and is then subsequently added to randomly mixed surfactant phospholipids in aqueous solution, it retains full potency as an anti-inflammatory and probably anti-viral agent.

Therefore, it is an embodiment of the invention to provide a substantially homogeneous preparation of the anionic lipids and/or related compounds of the present invention (described above and in more detail below), which may provided for use in any of the preventative or therapeutic methods described herein alone, or by admixture (combination, directed mixing) with other lipids, including surfactant preparations. It is a further embodiment of the invention to provide randomly mixed surfactant preparations, wherein at least 50% of the total lipids in the preparation is one or more of the particular anionic phospholipids or lipids or related compounds that form the basis of the present invention.

Accordingly, one embodiment of the present invention relates to compositions comprising an effective amount of at least one anionic lipid. According to the present invention, an anionic lipid useful in the present invention has at least the following characteristics: (1) has a hydrophobic portion; (2) has a negatively charged portion; and (3) has an uncharged, polar portion. Reference to an anionic lipid useful in the invention will be understood to refer to lipids with these qualities. Anionic lipids useful in the invention therefore include, but are not limited to, unsaturated phosphatidylglycerol, unsaturated phosphatidylinositol, saturated short chain phosphatidylglycerol, saturated short chain phosphatidylinositol, and derivatives of any of such phospholipids (e.g., polyethylene glycol (PEG) conjugates of these phospholipids), as well as anionic sphingolipids, anionic glycerolipids (anionic diglycerides, such as SQV-diglyceride), and any derivatives of such lipids. Preferred phospholipids include, but are not limited to, unsaturated phosphatidylglycerol, unsaturated phosphatidylinositol, palmitoyl-oleoyl-phosphatidylglycerol (POPG), and dimyristoyl-phosphatidylglycerol (DMPG). In one preferred embodiment, the phospholipids are selected from palmitoyl-oleoyl-phosphatidylglycerol (POPG) and/or phosphatidylinositol (PI) and/or derivatives thereof. The invention also includes the use of compounds closely related to unsaturated PG and unsaturated PI as inhibitors of inflammation, and particularly, antagonists of TLRs, and particularly, lyso-PG and lyso-PI. Because lyso-PG and lyso-PI have much higher water solubility and form micellar rather than bilayer structures, they would have greater access from the bulk solution to the TLRs. Thus, saturated or unsaturated lyso-PG, and saturated or unsaturated lyso-PI are predicted to be useful for the prevention and treatment of inflammation according to the invention, and as antagonists of the activation of TLRs 1,2,3,4,6,7, and 8, and in some embodiments, TLR10. General reference to "related compounds" with respect to the anionic lipids of the invention, refers to these lyso-PG and lyso-PI compounds, or other similar compounds.

Phosphatidylglycerol (PG) is a ubiquitous phospholipid that is a major component of bacterial cell membranes and a lesser component of animal and plant cell membranes. In animal cells, PG may serve primarily as a precursor for diphosphatidylglycerol (cardiolipin). PG is the second most abundant phospholipid in lung surfactant in most animal species. A particularly useful PG in the present invention is palmitoyl-oleoyl-phosphatidylglycerol (POPG).

Phosphatidylinositol (PI) is a key membrane constituent and is a participant in essential metabolic processes in all plants and animals (and in some bacteria (Actinomycetes)), both directly and via a number of metabolites. It is an acidic (anionic) phospholipid that in essence consists of a phosphatidic acid backbone, linked via the phosphate group to inositol (hexahydroxycyclohexane). In most organisms, the stereochemical form of the last is myo-D-inositol (with one axial hydroxyl in position 2 with the remainder equatorial), although other forms (scyllo- and chiro-) have been found on occasion in plants. PI is formed biosynthetically from the precursor CDP-diacylglycerol by reaction with inositol, catalysed by the enzyme CDP-diacylglycerol inositol phosphatidyltransferase.

Unsaturated PGs and PIs are defined herein as any PG or PI with one or more double bonds in the fatty acid chain.

Saturated PGs or PIs are defined herein as any PG or PI without a double bond (i.e., the chains are fully saturated with hydrogens). A saturated short chain PG or PI useful in the present invention includes any saturated 14 carbon or shorter PG or PI with anti-inflammatory properties as described herein. A particularly preferred saturated short chain PG includes, but is not limited to, dimyristoyl-phosphatidylglycerol (DMPG).

According to the present invention, an compositions containing an "effective amount" of an anionic lipid or related compound of the invention contain an amount of the specific anionic lipid or related compound effective to inhibit an inflammatory process in vitro or in vivo, or to inhibit viral infection in vitro or in vivo, as measured by any suitable technique for measuring such activity, several of which are described herein. Effective amounts of anionic lipids or related compounds of the invention to be included in a composition are described in more detail below.

In one aspect of the invention, the anionic lipids or related compounds are provided in a homogeneous lipid preparation comprising, consisting essentially of, or consisting of one or more of the anionic lipids or related compounds described above, and/or derivatives of any of such anionic lipids or related compounds. In one embodiment, any of the above-described lipid preparations further comprise any other lipid or lipid derivative that is useful in a surfactant preparation, useful in a therapeutic preparation, and/or useful for stabilizing the bilayer of lipids in a lipid preparation and/or decreasing leakage of encapsulated material.

In one embodiment, any of the above-described lipid preparation further comprise antioxidants, which are useful for inhibiting oxidation of the lipids in lipid preparation.

According to the invention, a lipid preparation useful in the invention can include any stabilized form of lipid that would be useful in a method of the invention, and particularly, any lipid that is stabilized by protein or another suitable compound. For example, lipid preparations useful in the invention include, but are not limited to, liposomes, and protein-stabilized lipid forms (e.g., non-liposomal lipids stabilized by the use of a lipoprotein, e.g., see Nanodisc™, Nanodisc, Inc.). According to the present invention, a liposome (also referred to as a liposomal preparation or liposomal composition) is a spherical, microscopic artificial membrane vesicle consisting of an aqueous core enclosed in one or more phospholipid layers. Liposomes can also be generally defined as self closed spherical particles with one or several lipid membranes. Liposomes can be composed of naturally-derived phospholipids with mixed fatty acid chains or prepared from synthetic lipids with well-defined lipid chains.

Depending on the number of the membranes and size of the vesicles, liposomes are considered to be large multilamellar vesicles (LMV) with sizes up to 500 nm, small unilamellar vesicles (SUV) with sizes <100 nm, and large unilamellar vesicles (LUV) with sizes >100 nm. Liposomes and liposome preparation methods are well known in the art, and several example of liposomes useful in the present invention, as well as methods of producing such liposomes and compositions comprising such liposomes, is described in the Examples. A stabilized lipid, such as a protein- or lipoprotein-stabilized lipid, can be prepared using any method known in the art.

In one exemplary embodiment, the lipid in the lipid preparation is composed of pure unsaturated PG, pure unsaturated PI, pure saturated short chain PG, pure saturated short chain PI, pure anionic sphingolipid, pure anionic glycerolipid, pure unsaturated lyso-PG, pure saturated lyso-PG, pure unsaturated lyso-PI, pure saturated lyso-PI, or any combinations thereof. In one exemplary embodiment, the lipid in the lipid preparation is composed of pure palmitoyl-oleoyl-phosphatidylglycerol (POPG), dimyristoyl-phosphatidylglycerol (DMPG), pure unsaturated PI, pure unsaturated PG, or any combinations thereof. Similarly, lipid preparations can be composed of any of these anionic lipids or related compounds, in combination with one or more different phospholipids and/or other lipid(s) and/or related compounds.

Preferred compositions for use in the invention provide an amount of the anionic lipids or related compounds described as useful in the present invention to provide a therapeutic or anti-inflammatory or anti-pathogen (e.g., anti-viral) effect when administered to an individual. For example, as discussed above, prior to the present invention, the presence of effective anionic phospholipids of the invention, such as PtdGro, in commercial surfactant preparations (including those derived from biological sources, such as porcine or bovine surfactant) has not, to the inventor's knowledge, had any demonstrable effect as an anti-inflammatory or anti-viral agent. This is because surface dilution and randomization of the effective phospholipids of the invention within a single vesicle of lipids significantly diminishes the potency of the lipid, as demonstrated in the Examples. As the Examples illustrate, in order to approximate the activity of the anionic phospholipid alone, randomized anionic phospholipid of the invention (e.g., POPG randomly mixed with surfactant lipids) must constitute nearly 50% of the total lipid present in a surfactant lipid-containing vesicle. However, if provided as a separate, homogeneous lipid preparation, even when admixed with other lipids after production of the lipid preparation, the anionic phospholipid of the invention can be provided in smaller quantities. This element of the invention can be extended to the other anionic lipids or related compounds of the invention.

Therefore, several different compositions of the anionic lipids or related compounds described herein are envisioned for use in the invention. In one embodiment, the invention provides a homogeneous lipid preparation consisting of the anionic lipid or related compound. As used herein, a "homogeneous" lipid preparation consisting of a specified anionic lipid or related compound or combination of specified anionic lipids or related compounds, means that the lipid preparation (e.g., the lipid vesicles or smaller portions) contains only the specified anionic lipid or related compound or a combination of specified anionic lipids or related compounds (e.g., a pure preparation of the specified phospholipid(s)), and is substantially or completely free of other phospholipids or other lipids. A homogeneous preparation of a specified anionic lipid or related compound can contain other non-lipid agents, if desired, such as antioxidants, a targeting moiety (described below), or another therapeutic agent (e.g., a protein, and antibody, a small molecule or drug). A homogeneous lipid preparation of the invention can be provided alone or with a pharmaceutically acceptable carrier, including an excipient or buffer, or in a composition with other agents or lipid preparations.

It is one embodiment of the invention to administer a homogeneous lipid preparation of an anionic lipid or related compound of the invention in the absence of any other lipids, although in other embodiments, the additive effects of other lipids, such as other lipids contained in surfactant, may be desirable and useful. In these alternate embodiments, the invention provides compositions that allow for the provision of such additional lipids and/or combinations of lipids, without losing the effectiveness of the particular anionic lipids or related compounds described herein. Such compositions are described below. Accordingly, in one aspect of the invention, the composition comprises other lipid preparations.

In one embodiment, the invention provides a composition comprising a homogeneous lipid preparation of the anionic lipid(s) or related compound(s) of the invention and at least one additional agent. The additional agent can include any pharmaceutical carrier, as discussed above, or an additional agent for the treatment of inflammation or pathogen infection (e.g., an anti-viral agent), for example.

Suitable anti-inflammatory agents include, but are not limited to, cytokine inhibitors, chemokine inhibitors, chemoattractant inhibitors, Cox inhibitors, leukotiene receptor antagonists, leukotriene synthesis inhibitors, inhibitors of the p38 MAP kinase pathway, glucocorticoids. More specifically, anti-inflammatory compounds can include, but are not limited to: any inhibitor of eicosanoid synthesis and release, including any Cox-2 inhibitor; Cox-1 inhibitors; inhibitors of some certain prostaglandins (prostaglandin E(2); PGD(2)), inhibitors of certain leukotrienes ($LTB_4$); classes of antibiotics with known direct or indirect anti-inflammatory effects, including macrolides (e.g. azithromycin) and fluoroquinolones (e.g., levofloxacin; moxifloxacin; gatifloxacin); inhibitors of p38 MAP kinase; inhibitors of the function of pro-inflammatory cytokines and chemokines, including antagonists of tumor necrosis factor (TNF), antagonists of interleukin-8 (IL-8); transforming growth factor beta (TGF-beta), β-agonists (long or short acting), antihistamines, phosphodiesterase inhibitors, corticosteroids, and other agents.

According to the present invention, a "pharmaceutically acceptable carrier" includes pharmaceutically acceptable excipients and/or pharmaceutically acceptable delivery vehicles, which are suitable for use in the administration of a preparation, formulation or composition, including a liposomal composition or preparation, to a suitable in vivo site. A suitable in vivo site is preferably any site wherein inflammation or infection by a pathogen, for example, is occurring or is expected to occur. Preferred pharmaceutically acceptable carriers are capable of maintaining a formulation of the invention in a form that, upon arrival of the formulation at the target site in a patient (e.g., the lung tissue), the formulation is capable of acting at the site, preferably resulting in a beneficial or therapeutic benefit to the patient. A delivery vehicle for a protein or agent can include the lipid preparation itself, if another agent is included, although in most embodiments of the invention, the lipid preparation is also a therapeutic agent as described herein (e.g., the lipid preparation can serve one or both functions).

Suitable excipients of the present invention include excipients or formularies that transport or help transport, but do not specifically target, a composition or formulation to a cell or tissue (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Formulations of the present invention can be sterilized by conventional methods and/or lyophilized.

A lipid preparation useful in the present invention can be modified to target to a particular site in a patient, thereby targeting and making use of the anionic lipids or related compounds and any agents carried by the lipid preparation at that site. Suitable modifications include manipulating the chemical formula of the lipid preparation and/or introducing into the lipid preparation a targeting agent capable of specifically targeting the lipid preparation to a preferred site, for example, a preferred cell type. Suitable targeting agents include ligands capable of selectively (i.e., specifically) binding another molecule at a particular site. Examples of such ligands include antibodies, antigens, receptors and receptor ligands.

In one embodiment, a particularly preferred composition suitable for use in the invention comprises a preparation (e.g., a lipid preparation) of randomly mixed anionic lipids or related compounds (any combination), and preferably, randomly mixed surfactant phospholipids or lipids (e.g., any combination of lipids found in surfactant), combined with (added to, mixed gently with, in admixture with) a homogeneous lipid preparation of the anionic lipids or related compounds useful in the present invention. In this embodiment, the combining of the randomly mixed lipids with the homogeneous lipid preparation of the anionic lipids or related compounds is performed in a manner that does not result in significant fusion and/or intermixing of lipids between the vesicle bilayers (e.g., between the randomly mixed lipid preparations and the pure or homogeneous lipid preparation of anionic lipids or related compounds. By producing a homogeneous preparation of the desired anionic lipids or related compounds and then adding it to another preparation of lipids, such as a randomized surfactant preparation, the inventor has discovered that the biological activity of the anionic lipids or related compounds described herein (e.g., anti-inflammatory, anti-pathogen, including anti-viral) is maintained. In this embodiment of the invention, it is preferred that the homogeneous lipid preparations of the anionic lipids or related compounds of the invention comprise at least 1% of the total lipids in the composition (e.g., the total lipids being those present in the homogeneous preparation and the added randomly mixed surfactant preparation), or at least 5%, or at least 10%, or at least 15%, or at least 20%, or at least 25%, or at least 30%, or at least 35%, or at least 40%, or at least 45%, or at least 50%, of the total lipids in the composition.

In another embodiment of the invention, a preparation of randomly mixed lipids is provided, and preferably a preparation of randomly mixed surfactant lipids and phospholipids, wherein the preparation contains one or more anionic lipids or related compounds useful in the present invention as described above. In this embodiment, the anionic lipid(s) or related compounds comprises at least about 30% of the total lipids in the randomly mixed surfactant lipids, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, of the total lipids in the randomly mixed surfactant lipids (or any amount between at least 30% and 100%, in whole number increments, e.g., 30%, 31%, 32%, etc.).

Preparations of randomly mixed lipids, and particularly, randomly mixed surfactant lipids can be made using techniques known in the art and are also available commercially (e.g., see Exosurf® (Wellcome, USA, an artificial surfactant preparation); Alveofact® (Thomae, Germany, prepared from bovine BAL); Curosurf® (Chiesi, Italy, prepared from minced porcine or bovine lung tissue) or Survanta® (Abbott, USA, prepared from minced porcine or bovine lung tissue)). Lung surfactant is a complex mixture of various phospholipids, neutral lipids and apoproteins (Doles, *Ann Rev Med* 1989; 40: 431-446; Jobe, *N Engl J Med* 1993; 328: 861-868; Tegtmeyer et al., *Eur Respir J*, 1996, 9, 752-757). Surfactant replacement therapy has proven to be beneficial for the treatment of the neonatal respiratory distress syndrome (Jobe, supra), and is also considered as a therapeutic option for term infants and adults with acute respiratory failure (Lewis and Jobe, *Am Rev Respir Dis* 1993; 147:216-233). Accordingly, surfactant lipid preparations are widely available and well known to those of skill in the art. It is believed that the addition of the homogeneous lipid preparations of anionic lipids and related compounds described herein to such preparations will significantly enhance the use of such commercial preparations or other surfactant preparations in the prevention and treatment of a variety of conditions, including those described directly above.

The total concentration of lipids to be delivered to an individual (e.g., to the lung) according to the present invention can range from about 5 µmol to about 1 mmol, including any amount between, in increments of 1 µmol. In one aspect, the amount delivered is from about 40 µmol to about 800 µM, although one of skill in the art can readily determine the appropriate amount to be delivered. By way of example, in one embodiment, the lipid preparation comprising a given anionic lipid (e.g., unsaturated PG) is delivered in an amount suitable to replace all resident lung PG). The estimated amount of unsaturated PG in the lung is approximately 400 umole in the entire adult lung residing in the alveolar compartment exclusive of the tissue. If the lipid preparation is to replace all resident lung PG, then 40 umol/ml×10 ml would be sufficient. It is an embodiment of the invention to provide the anionic lipid(s) and/or related compound(s) to the lung in an amount delivered that is equivalent to between about 10% of the total resident amount of the same or similar lipid, to about 200% of the total resident amount. Accordingly, from a lipid preparation that is 40 umol of the lipid or compound of the invention per ml of lipid preparation, the individual would receive between about 1 ml and 20 ml delivered in an aqueous suspension down the trachea, for delivery to the lungs.

In one embodiment, the lipid preparation useful in the present invention is complexed with another agent, such as a protein or a small molecule (drug), wherein the other agent is also useful for inhibiting or preventing inflammation or infection by a pathogen (e.g., a virus) in an individual. Methods of encapsulating or complexing proteins and other agents with lipids such as liposomes and protein-stabilized lipids are known in the art. The encapsulation efficiency of proteins by lipid preparations generally depends on interaction between the protein and the lipid bilayer or micelle. The protein entrapment can be increased by manipulation of the lipid preparation, or by increasing the lipid concentration, in order to favor electrostatic interactions, while monitoring the ionic strength of the protein solution (Colletier et al., *BMC Biotechnology* 2002, 2:9). Preferably, the amount of a protein complexed with lipid preparations will range from about 0.001 mg of protein per 1 ml lipid preparation to about 5 mg of protein per 1 ml lipid preparation.

Another embodiment of the invention relates to a method to produce a surfactant composition. The method includes (a) providing a homogeneous lipid preparation of an anionic lipid(s) and/or related compound(s) as described herein (e.g., an unsaturated phosphatidylglycerol, an unsaturated phosphatidylinositol, a saturated short chain phosphatidylglycerol, a saturated short chain phosphatidylinositol, anionic sphingolipid, anionic glycerolipid, unsaturated lyso-PG, saturated lyso-PG, unsaturated lyso-PI, saturated lyso-PI, or a derivative or combination thereof) and (b) adding the preparation of (a) to a preparation of randomly mixed surfactant lipids. The preparation of randomly mixed surfactant lipids can be produced by any suitable method known in the art or obtained commercially, as discussed above. Preferably, the preparation of (a) and/or (b) are in aqueous solution. Most preferably, the preparation is gently mixed to avoid significant fusion or intermixing of lipids between vesicle bilayers in (a) and (b), also as discussed above. In one aspect, the lipids in the preparation of (a) comprise at least 1% of the total lipids in the composition, or any amount from at least 1% to at least 50% or greater, in 1% increments.

One embodiment of the present invention relates to the use of any of the anionic lipid or related compound formulations described herein, including combinations thereof, to treat or prevent inflammation or a pathogen infection, and particularly a viral infection (e.g., RSV). The preventative and/or therapeutic methods of the invention generally include the administration to an individual (any individual, including infants, children and adults), any one or more preparations of the anionic lipids and/or related compounds described herein, alone or in combination with other lipids or agents, and/or as a supplement to conventional surfactant preparations or other therapies.

In one embodiment, the methods of the invention are useful for preventing or inhibiting inflammation or a pathogen infection associated with particular toll-like receptors, and specifically, TLR1, TLR2, TLR3, TLR4, TLR6, TLR7, TLR8, and/or TLR10. These TLRs have been associated, for example, with various bacterial infections, protozoan and fungal infections, viral infections e.g., Cytomegalovirus infection, Herpes simplex virus infection, measles, Varicella-zoster virus infection, HIV infection, rhinovirus infection, parainfluenza virus infection, Human parechovirus infection, influenza type A viral infection, Papilloma virus infection), cancer (including, but not limited to, melanoma), and autoimmune diseases. Accordingly, it is an embodiment of the invention to treat or inhibit inflammation associated with any of these conditions or to prevent or inhibit infection by a pathogen associated with any of these conditions.

One particular embodiment of the invention relates to a method to prevent or inhibit (suppress, reduce) infection by respiratory syncytial virus (RSV), as well as viral inflammation or infection by other viruses. The method includes the administration of any of the anionic lipid and/or related compound formulations described herein, including combinations thereof, to an individual who has or who is at risk of being infected by a virus, and particularly a virus associated with any of the TLRs discussed above, and more particularly, with RSV. With regard to RSV, the preparation can be administered to newborn infants, including to any newborn infant, regardless of whether the viral infection has been detected in the infant (i.e., the invention is useful as a prophylactic and as a therapeutic approach). Preparations of the anionic lipids and related compounds described herein can be used alone or in combination with other lipids or agents, and/or as a supplement to conventional surfactant preparations, to prevent and/or treat RSV infection.

The method of the invention is also useful for the prevention and/or treatment of other pulmonary infections and disorders, including in infants, children and adults, including, but not limited to, adult respiratory distress syndrome (ARDS), acute lung injury (ALI), viral infection associated with asthma, chronic obstructive pulmonary disease (COPD), pneumonia, bronchitis, tuberculosis, reactive airway disease syndrome, interstitial lung disease, rhinitis, and parasitic lung disease.

In accordance with the present invention, determination of acceptable protocols to administer a composition or formulation, including the route of administration and the effective amount of a composition or formulation to be administered to an individual, can be accomplished by those skilled in the art. An agent of the present invention can be administered in vivo or ex vivo. Suitable in vivo routes of administration can include, but are not limited to, oral, nasal, inhaled, topical, intratracheal, transdermal, rectal, intestinal, intra-luminal, and parenteral routes. Preferred parenteral routes can include, but are not limited to, subcutaneous, intradermal, intravenous, intramuscular, intraarterial, intrathecal and intraperitoneal routes. Preferred topical routes include inhalation by aerosol (i.e., spraying) or topical surface administration to the skin of an animal. Preferably, an agent is administered by nasal, inhaled, intratracheal, topical, or systemic routes (e.g., intraperitoneal, intravenous). Ex vivo refers to performing part of the administration step outside of the patient. Preferred routes of administration for antibodies include parenteral routes and aerosol/nasal/inhaled routes.

Intravenous, intraperitoneal, and intramuscular administrations can be performed using methods standard in the art. Aerosol (inhalation) delivery can be performed using methods standard in the art (see, for example, Stribling et al., Proc. Natl. Acad. Sci. USA 189:11277-11281, 1992, which is incorporated herein by reference in its entirety). Carriers suitable for aerosol delivery are described above. Devices for delivery of aerosolized formulations include, but are not limited to, pressurized metered dose inhalers (MDI), dry powder inhalers (DPI), and metered solution devices (MSI), and include devices that are nebulizers and inhalers. Oral delivery can be performed by complexing a therapeutic composition of the present invention to a carrier capable of withstanding degradation by digestive enzymes in the gut of an individual. Examples of such carriers, include plastic capsules or tablets, such as those known in the art. Administration of a composition locally within the area of a target cell refers to injecting the composition centimeters and preferably, millimeters from the target cell or tissue.

In humans, it known in the art that, using conventional methods for aerosol delivery, only about 10% of the delivered solution typically enters the deep airways, even using an inhaler. If the aerosolized delivery is by direct inhalation, one may assume a dosage of about 10% of that administered by nebulization methods. Finally, one of skill in the art will readily be capable of converting an animal dosage to a human dosage using alometric scaling. For example, essentially, a scale of dosage from mouse to human is based on the clearance ratio of a compound and the body surface of the mouse. The conversion for mg/kg is $\frac{1}{12}$th of the "no observed adverse event level" (NOEL) to obtain the concentration for human dosage. This calculation assumes that the elimination between mouse and human is the same.

Preferred amounts of lipid preparations to be delivered to an individual have been discussed in detail above.

In one embodiment, an effective amount of a preparation of the invention to administer to an individual is an amount that measurably inhibits (or prevents) inflammation or infection by a pathogen in the individual as compared to in the absence of administration of the formulation. A suitable single dose of a formulation to administer to an individual is a dose that is capable of reducing or preventing at least one symptom, type of injury, or resulting damage, from inflammation or pathogen infection in an individual when administered one or more times over a suitable time period. Preferably, a dose is not toxic to the individual.

One of skill in the art will be able to determine that the number of doses of a preparation to be administered to an individual is dependent upon the extent of the inflammatory condition or infection by a pathogen and/or the anticipated or observed physiological damage associated with such inflammation or infection, as well as the response of an individual patient to the treatment. The clinician will be able to determine the appropriate timing for delivery of the formulation in a manner effective to reduce the symptom(s) associated with inflammation or pathogen infection in the individual. Preferably, the agent is delivered within 48 hours, and more preferably 36 hours, and more preferably 24 hours, and more preferably within 12 hours, and more preferably within 6 hours, 5 hours, 4 hours, 3 hours, 2 hours, or 1 hour, or even minutes after the recognition of a condition to be treated by a formulation of the invention; after an event that causes inflammation in an individual or infection of an individual, or that is predicted to cause inflammation in or infection of an individual, which can include administration prior to the development of any symptoms of inflammation or infection in the individual.

Methods and uses directed to therapeutic compositions of the invention are primarily intended for use in the prevention and/or treatment of a disease or condition. The term "protecting" can be generically used to convey prevention and/or treatment. A therapeutic composition of the present invention, when administered to an individual, can: prevent a disease from occurring; cure the disease; delay the onset of the disease; and/or alleviate (reduce, delay, diminish) disease symptoms, signs or causes (e.g., reduce one or more symptoms of the disease; reduce the occurrence of the disease; increase survival of the individual that has or develops the disease; and/or reduce the severity of the disease). As such, the invention includes both preventing disease occurrence (prophylactic treatment) and treating an animal that has a disease or that is experiencing symptoms of a disease (therapeutic treatment).

According to the present invention, the methods of the present invention are suitable for use in an individual that is a member of the Vertebrate class, Mammalia, including, without limitation, primates, livestock and domestic pets (e.g., a companion animal). Most typically, an individual will be a human individual. The term "individual" can be interchanged with the term "subject" or "patient" and refers to the subject of a method according to the invention. Accordingly, an individual can include a healthy, normal (non-diseased) individual, but is most typically an individual who has or is at risk of developing an inflammatory condition or an infection, including a viral infection, or a symptom or indicator thereof as described herein.

The following experimental results are provided for purposes of illustration and are not intended to limit the scope of the invention.

EXAMPLES

Example 1

The following experimental results demonstrate that palmitoyl-oleoyl-phosphatidylglycerol (POPG) and phosphatidylinositol (PI), which are minor components of pulmonary surfactant, regulated the inflammatory response of alveolar macrophages. These results show that POPG and PI significantly inhibited LPS-induced nitric oxide and tumor necrosis factor (TNF)-α production from rat and human alveolar macrophages and a U937 cell line. POPG and PI reduced LPS-elicited phosphorylation of p38MAPK, ERK, and IkB-alpha; and expression of mitogen-activated protein kinase phosphatase (MKP-1). POPG was also effective at attenuating inflammation when administered intratracheally to mice challenged with LPS. Examination of cell surface binding by BODIPY-LPS revealed that POPG and PI inhibit LPS binding to the cell surface in a lipid structure specific manner. These data clearly identify important anti-inflammatory properties of surfactant phospholipids at the environmental interface of the lung.

Experimental Procedures

Cells and Reagents. LPS (0111:B4) purified from *Escherichia coli* was purchased from Sigma-Aldrich (St. Louis, Mo.). BODIPY-LPS (055:B5) purified from *E. coli* was purchased from InVitrogen, (Carlsbad, Calif.). PC, PG, sphingomyelin (SM), phosphatidylethanolamine (PE), phosphatidylserine (PS) and PI were purchased from Avanti Polar Lipids (Alabaster, Ala.). TNFα was from Genzyme (Cambridge, Mass.). Rabbit polyclonal anti-p46 JNK, rabbit polyclonal anti-p38, mouse monoclonal phospho-specific p46-p54 JNK antibodies, and rabbit polyclonal anti-mitogen-activated protein kinase phosphatase (MKP)-1 antibodies were purchased from Santa Cruz Biotechnology (Santa Cruz, Calif.). Rabbit polyclonal phospho-specific p42 ERK, rabbit polyclonal anti-p42 ERK, phospho-specific p38MAPK, rabbit polyclonal anti-IkBα, and phospho-specific IkBα antibodies were obtained from Cell Signaling Technology (Beverly, Mass.). [$^3$H]-Leucine was from Perkin Elmer Life Sciences (Boston, Mass.). The macrophage-like cell line U937 (CRL-1593.2) was obtained from American Type Culture Collection (Manassas, Va.). The cells were maintained in endotoxin-free Roswell Park Memorial Institute (RPMI) 1640 medium from Cambrex (East Rutherford, N.J.) with 10% heat-inactivated bovine growth serum (BGS; Hyclone, Logan, Utah). RAW 264.7 cells were maintained in DMEM with 10% BGS.

Isolation of Rat Alveolar Macrophages. Rat alveolar macrophages were isolated from bronchoalveolar lavage fluid (BALF) of Sprague-Dawley rats. The lungs were lavaged with pyrogen-free saline, and alveolar macrophages were sedimented by centrifugation at 150×g×5 min. Isolated macrophages were plated at 5×10$^5$ cells/well in 24-well plates (Falcon) in RPMI 1640 medium containing 10% BGS. The cells were allowed to adhere for 2 h and then used for the experiments after washing with phosphate-buffered-saline (PBS) to remove the unattached cells.

Isolation of Human Alveolar Macrophages. Human alveolar macrophages were isolated from BALF of healthy volunteers using protocols reviewed and approved by the National Jewish Medical Research Center IRB and the University of Colorado General Clinical Research Center. The lungs were lavaged with pyrogen-free saline, and alveolar macrophages were sedimented by centrifugation at 150×g×5 min. Isolated macrophages were plated at 5×10$^4$ cells/well in 96-well plates (Falcon) in RPMI 1640 medium containing 10% BGS. The cells were allowed to adhere for 48 h and then used for the experiments after washing with PBS to remove the unattached cells.

Induction of TNF-α Secretion. U937 cells were induced to differentiate by treatment with 10 nM phorbol myristate acetate (PMA) for 48 h. The cells (1.3×10$^5$/well) were placed in 96-well plates and further incubated in the absence of PMA for 24 h in RPMI 1640 medium containing 10% BGS. Rat alveolar macrophages (5×10$^5$/well) were incubated in 24-well plates for 2 h after isolation. The indicated concentration of phospholipids was added to the cultures 30 min before adding LPS. After LPS addition cultures were incubated for 6 h at 37° C. at an atmosphere of 95% air and 5% $CO_2$. At the end of the incubation period the medium was collected and assayed for TNF-α concentrations using an ELISA kit.

Preparation of Surfactant Lipids. Surfactant lipids were isolated from the bronchoalveolar lavage of Sprague-Dawley rats, 28 days after intratracheal instillation of 25 mg of silica (~125 mg/kg). Initially, the surfactant was purified by the method of Hawgood et. al. (25) using NaBr density gradient centrifugation. The purified surfactant was extracted with butanol (26) and segregated into butanol-soluble and -insoluble material. The butanol-soluble surfactant lipids were recovered by drying under vacuum and resuspending in chloroform. The phospholipid content was determined by the method of Rouser et al (27), and the mixture was stored at −20° C. Prior to use, an aliquot of surfactant lipids was initially dried under nitrogen, and subsequently hydrated in 20 mM Tris (pH 7.4), 150 mM NaCl buffer at 37° C. for 1 h. Finally the surfactant lipids were probe-sonicated in 5-30 s bursts with 1 min cooling between bursts, to make a vesicle preparation for use in experiments.

Analysis of Nitric Oxide Accumulation. Nitric oxide (NO) accumulation in the supernatant was determined as previously reported (28). Briefly, rat alveolar macrophages were stimulated with LPS (10 ng/ml) or LPS plus phospholipids for 24 h. Culture supernatants (usually 100 µl) were combined with an equal volume of Greiss reagent, and the samples were incubated at room temperature for 10 min before the absorbance was quantified at 550 nm. With the use of a standard curve, the nmol of NO produced were determined and normalized to total cell number in each sample.

Analysis of Cytokine Production. Human and mouse TNF-α ELISA kits were purchased from BioSource (Camarillo, Calif.). Mouse KC and MIP-2 Quantikine kits were purchased from R&D System. Measurements of these cytokines were according to the manufacturers' protocols.

Measurement of MARK, IkBα and MKP-1. Monolayers of unstimulated or stimulated macrophages were lysed on ice with 250 µl of ice-cold lysis buffer [50 mM Tris.HCl, pH 8.0, containing 137 mM NaCl, 10% (vol/vol) glycerol, 1% (vol/vol) Nonidet P-40, 1 mM NaF, 10 µg/ml leupeptin, 10 µg/ml aprotinin, 2 mM $Na_3VO_4$, and 1 mM phenylmethylsulfonyl fluoride (29). Insoluble nuclear material was pelleted by centrifugation at 14,000×g for 10 min at 4° C. and the supernatants were collected. 15 µg of protein from lysates was separated by SDS-PAGE and transferred onto nitrocellulose membranes (30). The blots were then washed in Tris-Tween-buffered saline [TTBS, 20 mM Tris-HCl buffer, pH 7.6, containing 137 mM NaCl and 0.05% (vol/vol) Tween 20], blocked with 5% (wt/vol) nonfat dry milk for 1 hour, and probed according to the method described by Towbin et. al. (30) with phospho-specific antibodies to p46-p54 JNK, p42/p44 ERK, and p38MAPK, or IkBα or with a polyclonal MKP-1 or IkBα antibodies in 5% (wt/vol) BSA dissolved in TTBS. With the use of horseradish peroxidase-conjugated secondary anti-rabbit or anti-mouse antibody, bound antibodies were detected by enhanced chemiluminescence (ECL plus, Amersham Biosciences, Piscataway, N.J.). To determine loading of proteins between samples, the membranes were probed with rabbit polyclonal p46 JNK, p42/p44 ERK, and p38MAPK antibodies.

Administration of LPS and Phospholipids In Vivo. Female BALB/c mice from 6 to 8 weeks of age were obtained from Jackson Laboratories (Bar Harbor, Me.). Experiments were conducted under a protocol approved by the Institutional Animal Care and Use Committee of the National Jewish Medical and Research Center. Liposomes were formed using a Liposofast™ (Avestin; Ottawa, Canada), which makes unilamellar liposomes of 100 nm of diameter, and then mixed with an aqueous solution containing LPS. The mixture of LPS and phospholipids was sprayed into murine trachea using a MicroSprayer™ aerosolizer (PennCentury, Philadelphia, Pa.) under isoflurene anesthesia. Delivery by MicroSprayer™ has been shown to result in lung deposition fractions of more than 93% in primates (31). After stimulation, lungs were lavaged via the trachea with 1 ml of Hank's balanced salt solution (Invitrogen Corporation, Carlsbad, Calif.). The volume of collected BALF was measured in each sample and the number of leukocytes was counted (Coulter Counter; Coulter Corporation, Hialeah, Fla.). Differential cell counts were determined from at least 300 cells on cytocentrifuged preparations (Cytospin; Shandon Ltd., Runcorn, Cheshire, UK). Slides were stained with modified Wright-Giemsa (Hema; Protocol, Swedesboro, N.J.) and the cell populations differentiated by standard hematologic procedures. Cytokine levels in the BALF or in the supernatants of cultured airway macrophages were measured using ELISA kits.

Binding of Phospholipids to RAW264.7 Macrophages. RAW264.7 cells ($10^6$) were incubated with BODIPY-LPS (1 µg/ml) either with or without phospholipid liposomes (200 µg/ml) at 4° C. for 4 h. When liposomes were added, a 1 h preincubation preceded the addition of fluorescent LPS. After the cells were washed with PBS by centrifugation, cell adherent fluorescence was determined using FACScan. Macrophages were counted for 20,000 cells and the graph was made by CellQuest software.

Statistical Analysis. All results were expressed as mean±S.E. ANOVA was used to determine the levels of difference between all groups. Groups were compared by unpaired two-tailed t-test. The p-value for significance was set at 0.05.

Results

POPG and PI Inhibit LPS-Induced Production of Proinflammatory Cytokines.

Figure 2:
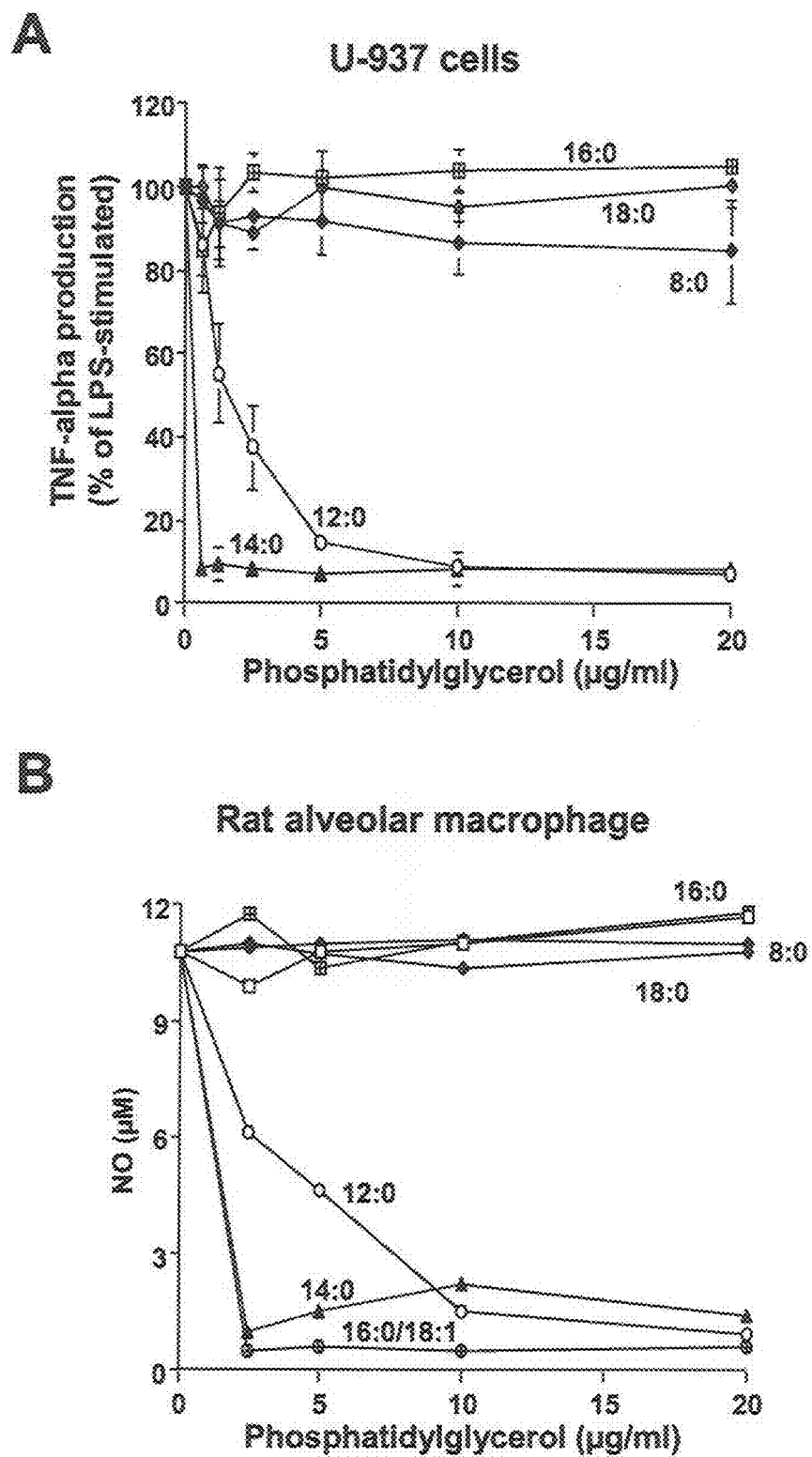
FIG. 2. The inhibitory effect of phosphatidylglycerols on LPS-induced inflammatory mediator production is molecular species specific. PG liposomes were formed by bath-sonication for 30 min at room temperature. LPS (10 ng/ml) and different concentrations of PG were added to monolayer cultures of differentiated U937 cells (A) or rat alveolar macrophages (B). Media TNF-α measurements were performed 6 h after stimulation. Media NO measurements were performed 24 h after stimulation. LPS stimulation without PG was set at 100%. The molecular species of PG shown on the graph are 8:0; dioctanoyl-phosphatidylglycerol, 12:0; dilauroyl-phosphatidylglycerol (DLPG), 14:0; dimyristoyl-phosphatidylglycerol (DMPG), 16:0; dipalmitoyl-phosphatidylglycerol (DPPG), 18:0; distearoyl-phosphatidylglycerol, 16:0/18:1; palmitoyl-oleoyl-phosphatidylglycerol (POPG). The data shown are the means±S.E. from three separate experiments with duplicate samples in each experiment. The average TNF-α production upon LPS stimulation was 11.3±0.7 ng/ml. The average NO production upon LPS stimulation was 10.1±0.6 μM.

In the initial studies, the inventors investigated the ability of purified lipids normally present as minor components of pulmonary surfactant to modulate LPS-induced cytokine secretion. Macrophages were stimulated with LPS in the presence or absence of purified phospholipids (FIG. 1). Culture supernatants were collected and TNF-α production by U937 cells and NO production by rat alveolar macrophages was determined POPG and PI significantly attenuated TNF-α and NO production in a concentration dependent manner with the maximal inhibitory effect ≤2.5 µg phospholipids/ml. Another anionic phospholipid, PS, was less effective than PI and POPG. In contrast, the aminophospholipids and sphingolipids DPPC, PE and SM had no significant effect on TNF-α or NO production. The major molecular species of PG in humans is POPG, whereas rodent surfactant contains a mixture of disaturated and unsaturated PG. The inventors next examined the effect of saturation and acyl chain length of PGs on the inhibition of LPS induced inflammation. As shown in FIG. 2, disaturated PGs containing two palmitic (16:0), stearic (18:0), or octanoic (8:0) fatty acids failed to antagonize LPS induced TNF-α or NO production. However, PGs with two myristic (14:0) fatty acids were as potent as POPG as antagonists of LPS. PGs with two lauric (12:0) fatty acids were also modest antagonists of LPS induced cytokine production. Although the reagents were not available to compare different molecular species of PI for LPS antagonism, the PIs that were used were unsaturated with the major form containing 16:0 and 18:2 fatty acids. From the above findings, it was concluded that unsaturated PGs and PIs and selected saturated PGs act as potent antagonists of LPS action upon macrophages.

POPG Antagonism of LPS Induced Inflammation Occurs in the Context of Surfactant Phospholipids.

Figure 3:
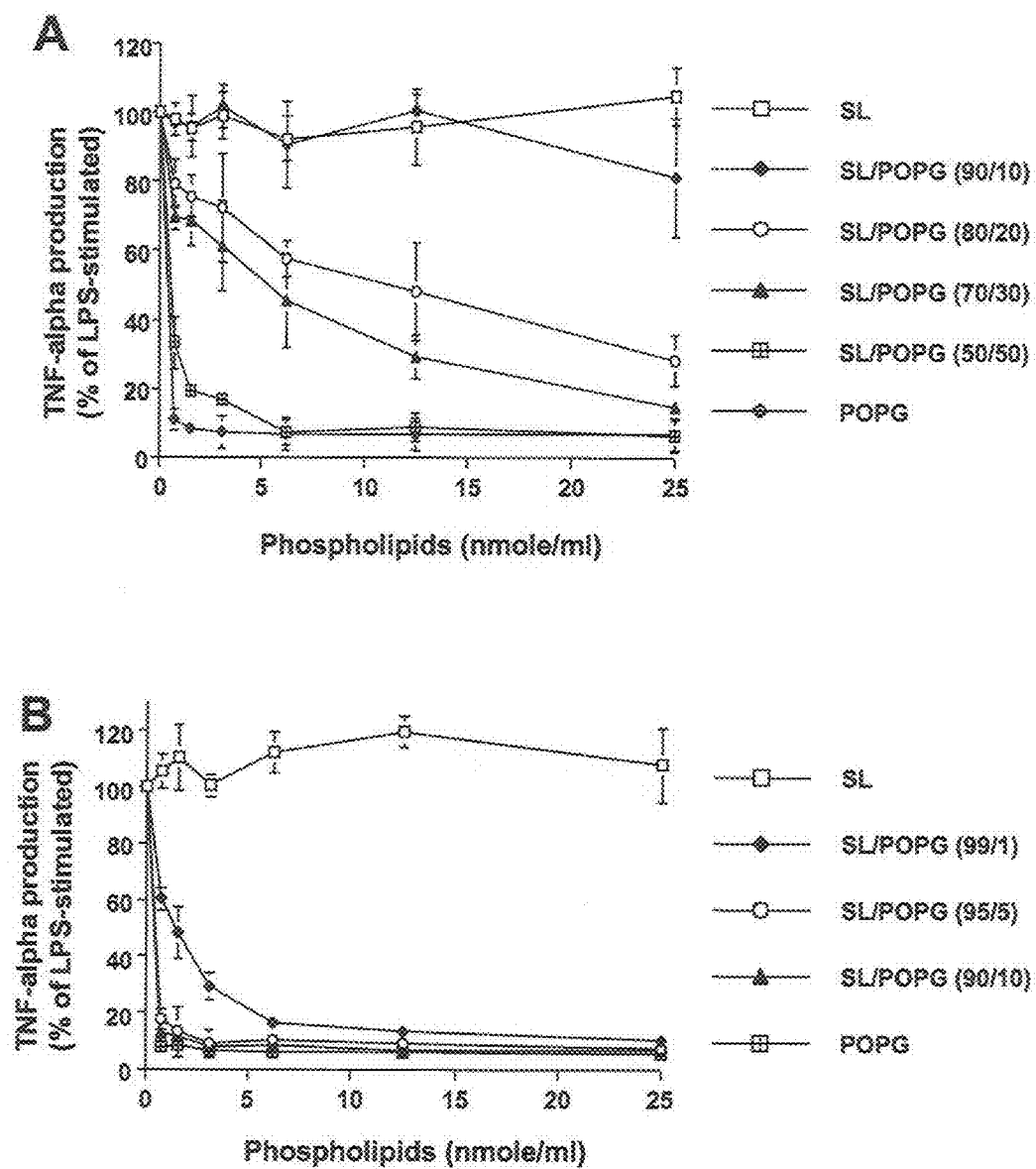
FIG. 3. Homotypic PG containing liposomes are most effective in antagonizing LPS action in the presence of surfactant lipids. Surfactant lipid (SL) and POPG were dried under nitrogen, and hydrated at 37° C. for 1 h. (A) SL and POPG were mixed in organic solvents prior to drying and hydrating and subsequently liposomes were produced. (B) SL and POPG were made as independent populations of liposomes that were subsequently mixed prior to macrophage treatment. 10 ng/ml of LPS and different concentrations of liposome mixtures were added to monolayer cultures of differentiated U937 cells. 6 h after stimulation, media were collected and TNF-α production was determined LPS stimulation without phospholipid was set as 100%. The data shown are the means±S.E. from three separate experiments with duplicate samples in each experiment. The average TNF-α production upon LPS stimulation was 7.0±0.2 ng/ml.

The POPG present in the alveolar compartment is in a lipid rich environment with concentrations of total phospholipids of 10-15 mg/ml (32), and the inventors examined whether these other lipids can interfere with LPS antagonism. Two types of experiments were performed. In one set of experiments, POPG was added to organic solvent extracts of surfactant using a method that ensured ideal mixing of all components. In this first procedure, the POPG and all other lipids were randomly mixed in each lipid extract and then liposomes were prepared by sonication. In a second set of experiments, vesicles composed of surfactant lipids and vesicles composed of POPG were prepared separately and then combined. In this latter situation there will be two populations of vesicles, one containing randomly mixed surfactant lipids and a second containing pure POPG. The results presented in FIG. 3A reveal that surface dilution and randomization of POPG within a single vesicle significantly diminishes the potency of the lipid as an antagonist of LPS action. In order to approximate the activity of POPG alone, the randomized POPG must now constitute nearly 50% of the total lipid present in a surfactant lipid-containing vesicle. In contrast to the results in FIG. 3A, the data presented in FIG. 3B demonstrate that admixture of pure POPG vesicles and randomized surfactant lipid vesicles has essentially no effect upon the activity of POPG as an LPS antagonist, measured by TNF-α production. This result also indicates that the combination of pure POPG vesicles with surfactant lipid vesicles does not result in significant fusion and intermixing of lipids between vesicle bilayers. This important result suggests that the introduction of POPG vesicles into the surfactant environment of the alveolar compartment of the lung may yield physical forms of the lipid capable of potently antagonizing LPS action.

POPG Inhibits the Phosphorylation of MARK and IkBα and Expression of MKP-1.

Figure 4:
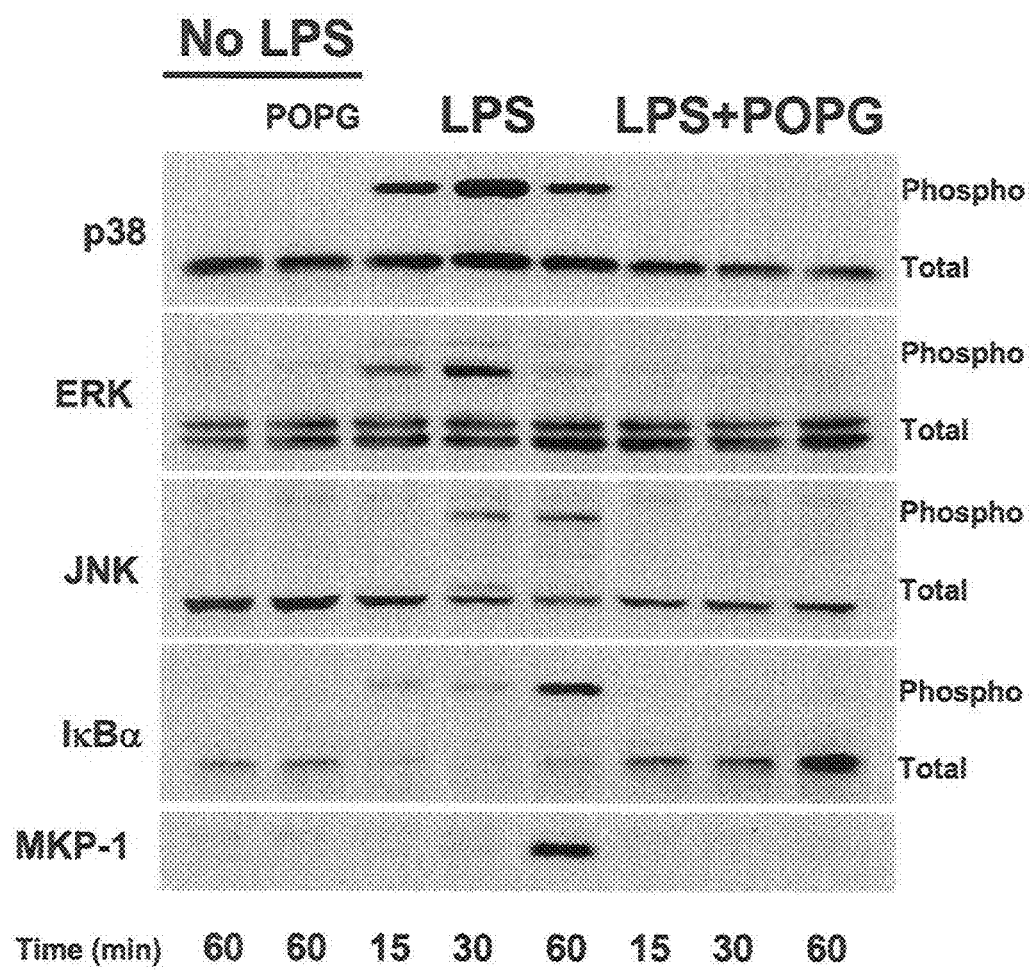
FIG. 4. POPG inhibits LPS induced MAPK and IkBα phosphorylation and MKP-1 expression. POPG liposomes (200 μg/ml) were added to monolayer cultures of differentiated U937 cells that received either no treatment or 10 ng/ml LPS. After incubating for the indicated time, cells were lysed using lysis buffer containing detergent, protease inhibitors and phosphatase inhibitors. Aliquots with 15 μg of protein from lysates were separated by SDS-PAGE and transferred onto nitrocellulose membranes. The amount of phosphorylation was detected using phospho-specific antibodies to p38MAPK, p42/p44 ERK, p46-p54 JNK and phosphorylated IkBα. To determine equal loading of proteins between samples, the membranes were probed with rabbit polyclonal p46 JNK, p42/p44 ERK, p38MAPK and IkBα antibodies. The expression of MKP-1 was detected with a polyclonal MKP-1 antibody.

The inventors next investigated the influence of phospholipids upon the intracellular signaling pathways of LPS-induced TNF-α secretion. Host cells recognize many specific microbial components through toll-like receptors that mediate immune responses. On alveolar macrophages, LPS binds to membrane CD14 and a TLR4-MD2 complex. The signals from TLR4 are transmitted through MyD88 and TRAF6 (33) to IkBα or mitogen activated protein kinases (MAPKs) such as ERK, JNK and p38. These signals regulate transcription factors and induce proinflammatory cytokine production. In experiments summarized in FIG. 4, differentiated U937 cells were stimulated with LPS in the absence or presence of POPG and cell lysates were electrophoresed and immunoblotted (FIG. 4). Significant increases in phosphorylated forms of p38, p42ERK and JNK, as well as IkBα were detected between 15 and 60 mins after LPS treatment. LPS treatment also reduced the steady state levels of IkBα due to protein degradation. Treatment of cells with POPG in addition to LPS eliminated the phosphorylation of p38, p42ERK, JNK and IkBα and also abrogated the reduction in the steady state levels of IkBα. In addition to inducing phosphorylation of MAPKs and IkBα, LPS induces synthesis of MKP-1 that functions to turn off MAPKs signaling (34, 35). The POPG treatment blocked the synthesis of new MKP-1, indicating that the lipid is likely to act upstream of MAPK activation rather than downstream of the process by induction of MKP-1.

Figure 5:
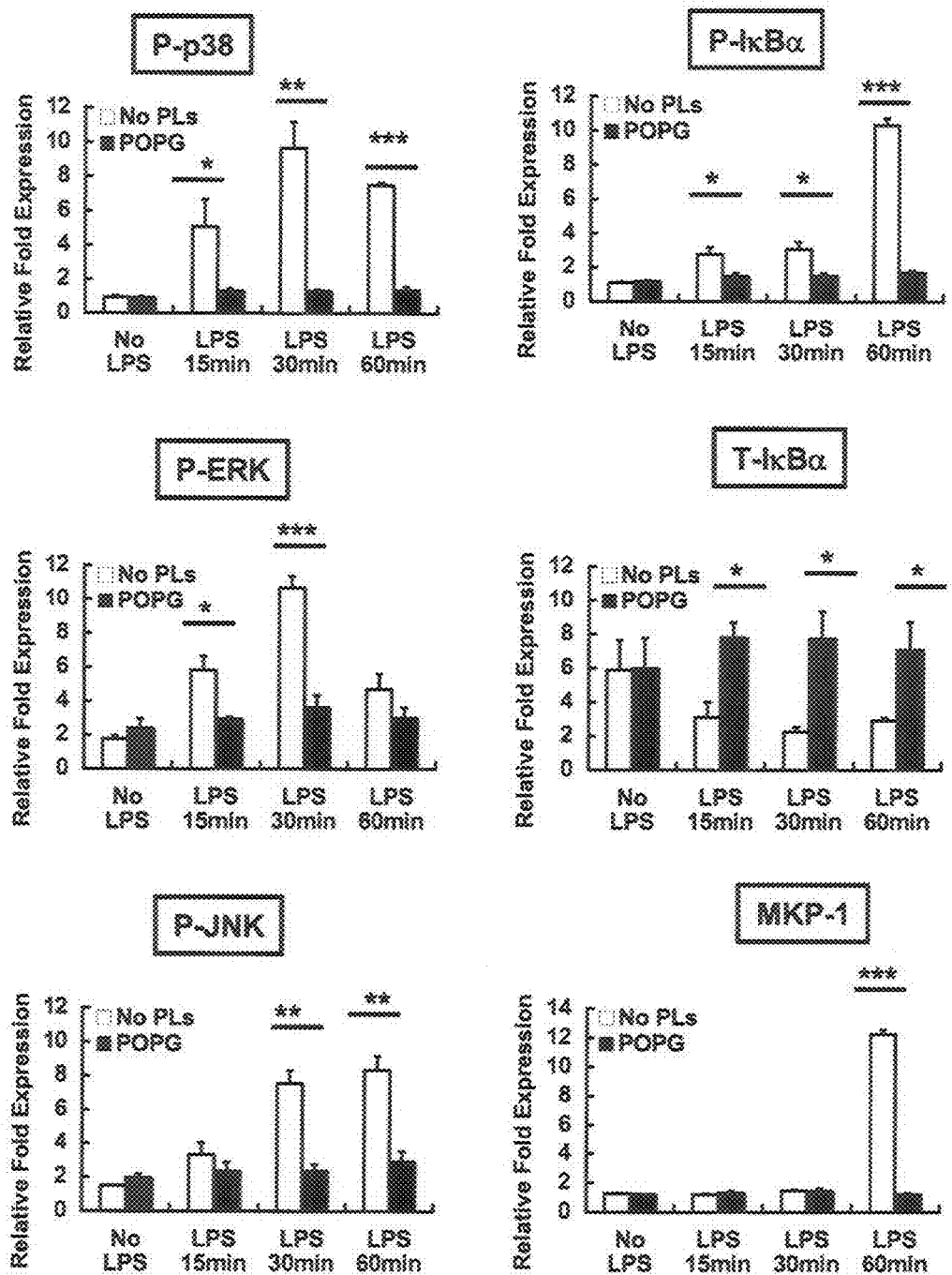
FIG. 5. Quantification of POPG inhibition of LPS induced signaling. Western blot analysis as described in FIG. 4 was performed three or four times on separate samples and the intensity of phospho-p38, phospho-IkBα, phosphoERK, phospho JNK, phospho IkBα, total IkBα and MKP-1 was calculated using NIH Image J1.34 software. Significance—*: p<0.05, **: p<0.01, when compared between LPS and LPS with POPG stimulation.

The quantification of western blotting results from multiple experiments performed as shown in FIG. 4 is presented in FIG. 5. The POPG treatment significantly reduces p38, ERK, JNK and IkBα phosphorylation in LPS stimulated cells to values nearly equivalent to untreated cells. The expression of MKP1 was also reduced to control levels by POPG treatment. In addition, the total amount of IkBα present in the cells remained constant when LPS treated cells were also given POPG. This latter result demonstrates that POPG prevents degradation of IkBα that occurs subsequent to LPS treatment alone.

Figure 6:
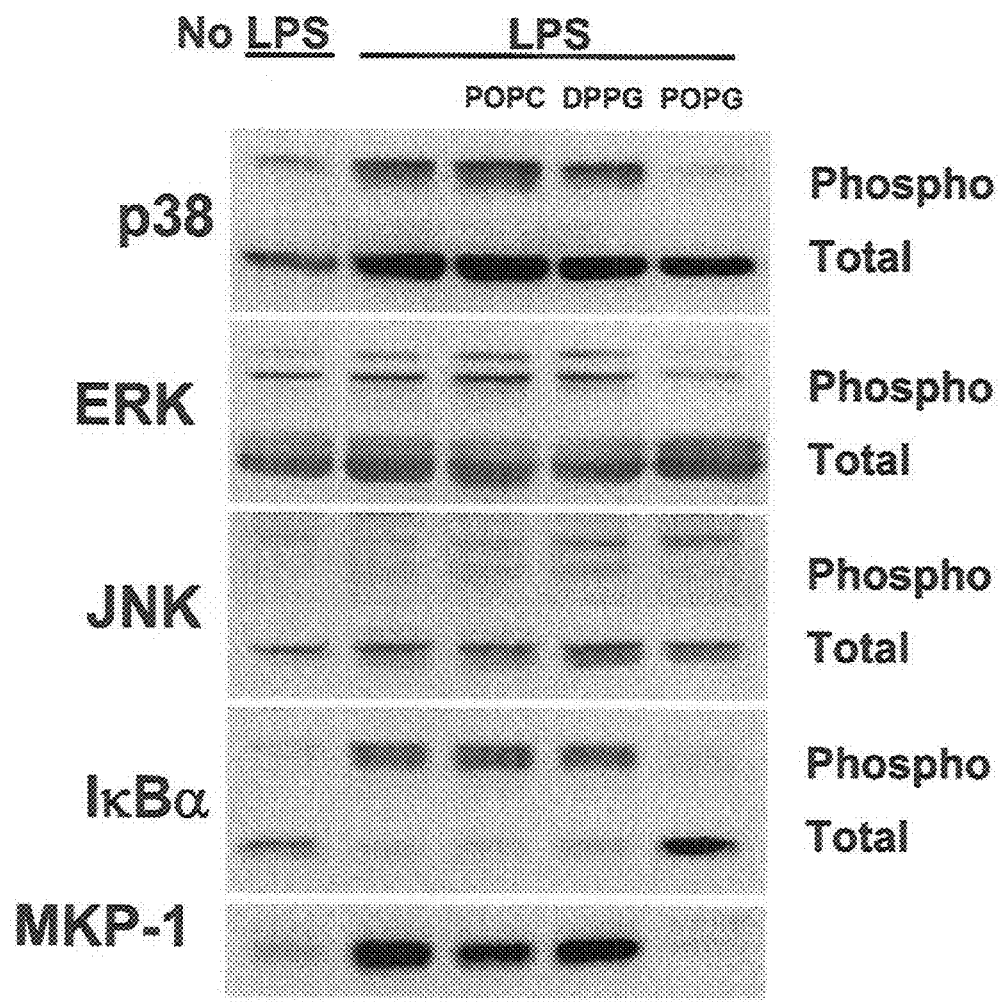
FIG. 6. Molecular specificity in POPG action. Liposomes composed of POPC, DPPG or POPG were added to monolayer cultures of differentiated U937 cells that received either no treatment or 10 ng/ml LPS, as indicated. After 30 or 60 min cells were lysed and 15 μg of cellular protein from cultures was separated by SDS-PAGE and transferred onto nitrocellulose membranes. Phosphorylated and nonphosphorylated proteins were detected as described in FIG. 4.
Figure 7:
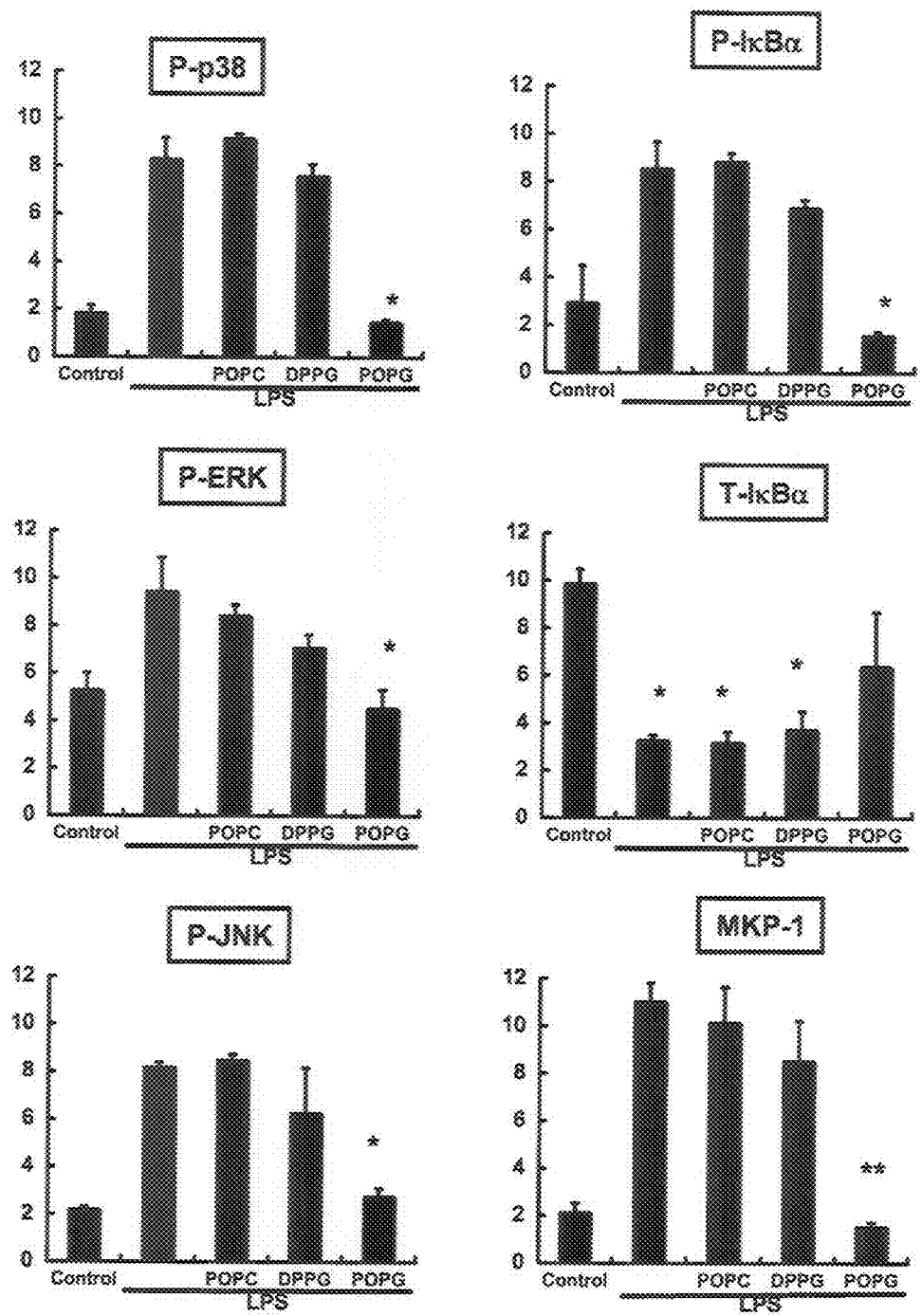
FIG. 7. Comparative quantification of lipid dependent antagonism of LPS signaling. Western blot analysis was performed as described in FIG. 6 in three independent experiments. The intensity of the phosphorylated (p38, ERK, JNK and IkBα) and nonphosphorylated (total IkBα and MKP-1) proteins of interest was measured using NIH Image J1.34 software. Significance—*p<0.05, **p<0.01.

The molecular specificity of the POPG action upon MAPKs, IkBα and MKP-1 was also examined as shown in FIG. 6. In these experiments POPG was compared to POPC and DPPG. The results clearly demonstrate the importance of the contributions from the polar headgroup and the fatty acid substituents of the phospholipid. Whereas POPG potently inhibited p38, ERK, JNK, and IkBα phosphorylation and MKP-1 protein expression, neither POPC nor DPPG exerted a significant effect on these parameters. The quantification of the data in FIG. 6 is given in FIG. 7, which summarizes results from three independent experiments.

The inventors also conducted control experiments to test whether POPG treatment had a general toxic effect upon U937 cells. Protein synthesis was measured by determining [$^3$H]-Leucine incorporation into trichloroacetic acid precipitable material in the presence and absence of 200 μg/ml POPG. No changes in protein synthesis occurred over a 6 hr period in POPG treated U937 cells compared to untreated cells in 3 independent experiments. Additional studies were performed to examine whether POPG pleiotropically inhibited signaling by macrophages. In these studies, macrophages were treated with TNF-α (10 ng/ml) and the degradation of IkBα was measured. POPG treatment of TNF-α stimulated macrophages failed to alter IkBα degradation when compared to stimulated cells without POPG treatment. Collectively, these studies indicate that the actions of the anionic lipids upon LPS signaling are specific.

Anionic Phospholipids Antagonize LPS Activation of Human Alveolar Macrophages.

Figure 8:
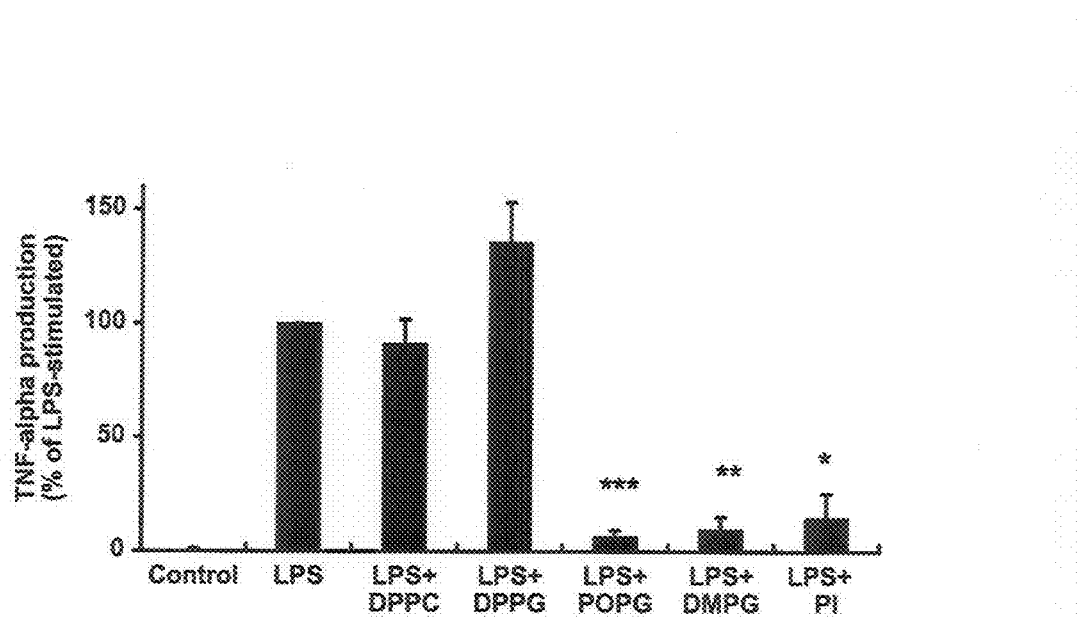
FIG. 8. POPG, DMPG and PI antagonize the effects of LPS on primary human alveolar macrophages. Human alveolar macrophages were isolated from healthy volunteer BALF and plated onto a 96-well plate. Two days after plating, 10 ng/ml of LPS and 20 μg/ml of phospholipids were added to monolayer cultures of human alveolar macrophages. 6 h after stimulation, media were collected and TNF-α production was determined by ELISA. LPS stimulation without phospholipid was set at 100%. The data shown are the means±S.E. from three separate experiments with duplicate samples in each experiment. The average TNF-α secretion after LPS stimulation was 30.7±15.1 ng/ml. Significance—**: p<0.01, when compared with LPS stimulation in the absence of POPG.

The inventors next examined whether the findings obtained with human tissue culture macrophages and rat alveolar macrophages were also relevant to human alveolar macrophages in primary culture. The human macrophages were isolated by bronchoalveolar lavage and challenged with 10 ng/ml LPS for 6 hr. The inflammatory response was assessed by measuring TNF-α production. The results presented in FIG. 8 demonstrate that POPG, dimyristoyl PG or PI markedly attenuate the inflammatory response of freshly isolated human alveolar macrophages to LPS. In contrast, DPPG and DPPC had no significant effect upon the human alveolar macrophage response to LPS. These results demonstrate that human macrophages residing in the alveolar compartment are susceptible to having their inflammatory response to LPS greatly attenuated by anionic surfactant phospholipids and the synthetic lipid DMPG.

POPG Inhibits LPS-Induced Proinflammatory Cytokine Production In Vivo.

Figure 9:
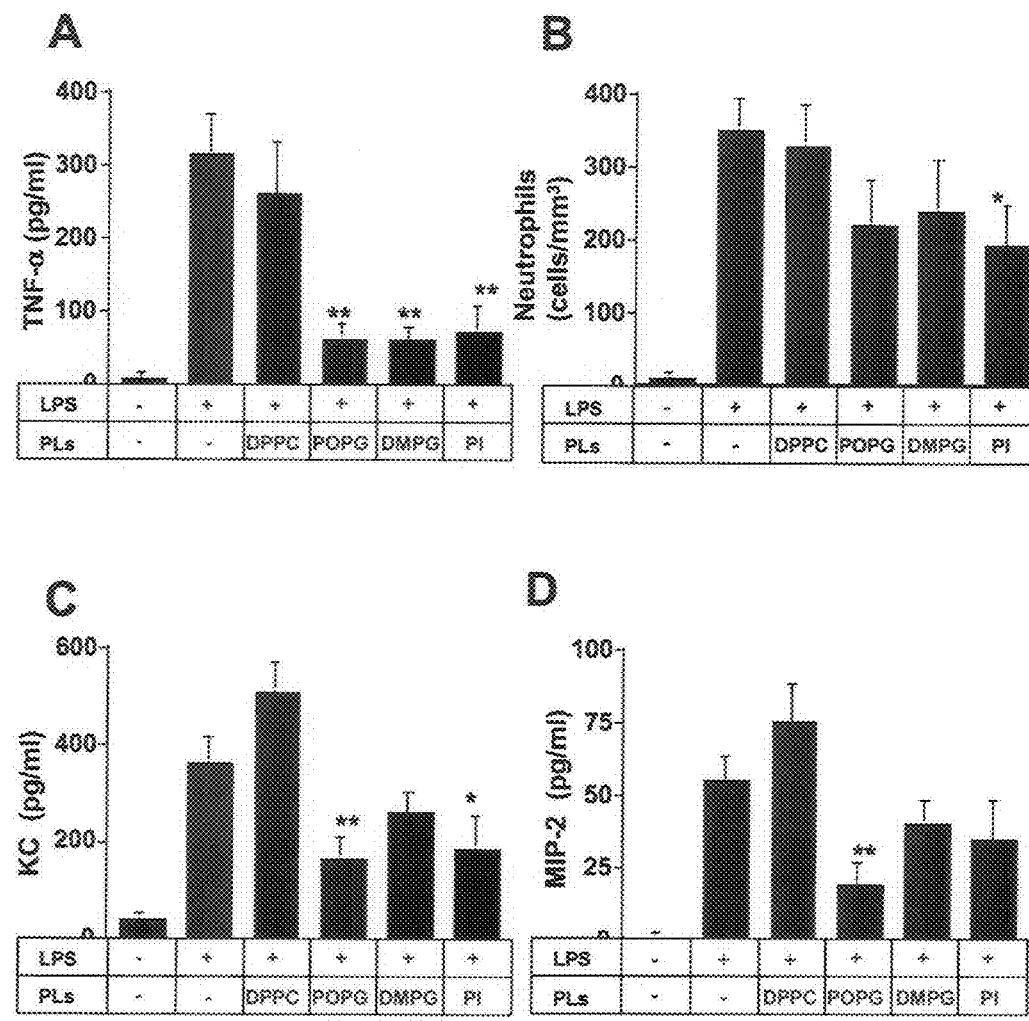
FIG. 9. Anionic phospholipids modulate lung inflammation induced by intratrachealy administered LPS. A mixture of LPS (1 μg) and phospholipids (30 μg) in 20 μl of PBS was sprayed into murine trachea using a MicroSprayer™ aerosolizer. At 18 h after stimulation, lungs were lavaged via the trachea. TNF-α production (A) was determined by ELISA. The number of leukocytes was counted and differential cell counts (B) were determined from at least 300 cells on cytocentrifuged preparations. Mouse KC (C) and MIP-2 (D) secretion were determined using Quantikine kits (R&D System). The data shown are the means±S.E. from six to eight mice. Significance—*: p<0.05, **: p<0.01, when compared between LPS and LPS plus POPG.

Since POPG was a strong inhibitor of TNF-α and NO production in vitro, the inventors examined if this lipid can inhibit inflammation in vivo. Phospholipid liposomes were formed using a Liposofast™ apparatus. Mixtures of LPS and phospholipids were sprayed into the trachea of mice using a MicroSprayer™ positioned at the vocal cords. At 18 h after stimulation, the lungs of mice were lavaged (FIG. 9) and TNF-α, neutrophil infiltration, and interleukin (IL)-8 equivalents (KC and MIP-2) were measured in the recovered lavage fluid. These three inflammatory indicators are important prognostic determinants of ALI/ARDS (36). LPS-induced TNF-α was approximately 300 μg/ml and was unaffected by DPPC instillation. In contrast, POPG, DMPG and PI significantly attenuated the TNF-α secretion in the lung. These results clearly indicate that the intratrachealy administered POPG and PI can reduce the inflammation in the lung in vivo. These results correlate well with in vitro results. LPS stimulation also induced the infiltration of neutrophils. POPG, DMPG and PI, but not DPPC, modestly attenuated the LPS-induced neutrophil infiltration. Since IL-8 has not been identified in mice, the inventors measured KC and MIP-2 as the functional homologues of IL-8 (37). DMPG, PI and especially POPG attenuated the KC and MIP-2 secretion in BALF. These findings suggest that the antagonistic phospholipids will inhibit the secretion of IL-8 from human alveolar macrophages in vivo. These results reveal a high potential for POPG or PI to be used as chemotherapeutic agents for LPS-elicited disorders in human lung.

Figure 10:
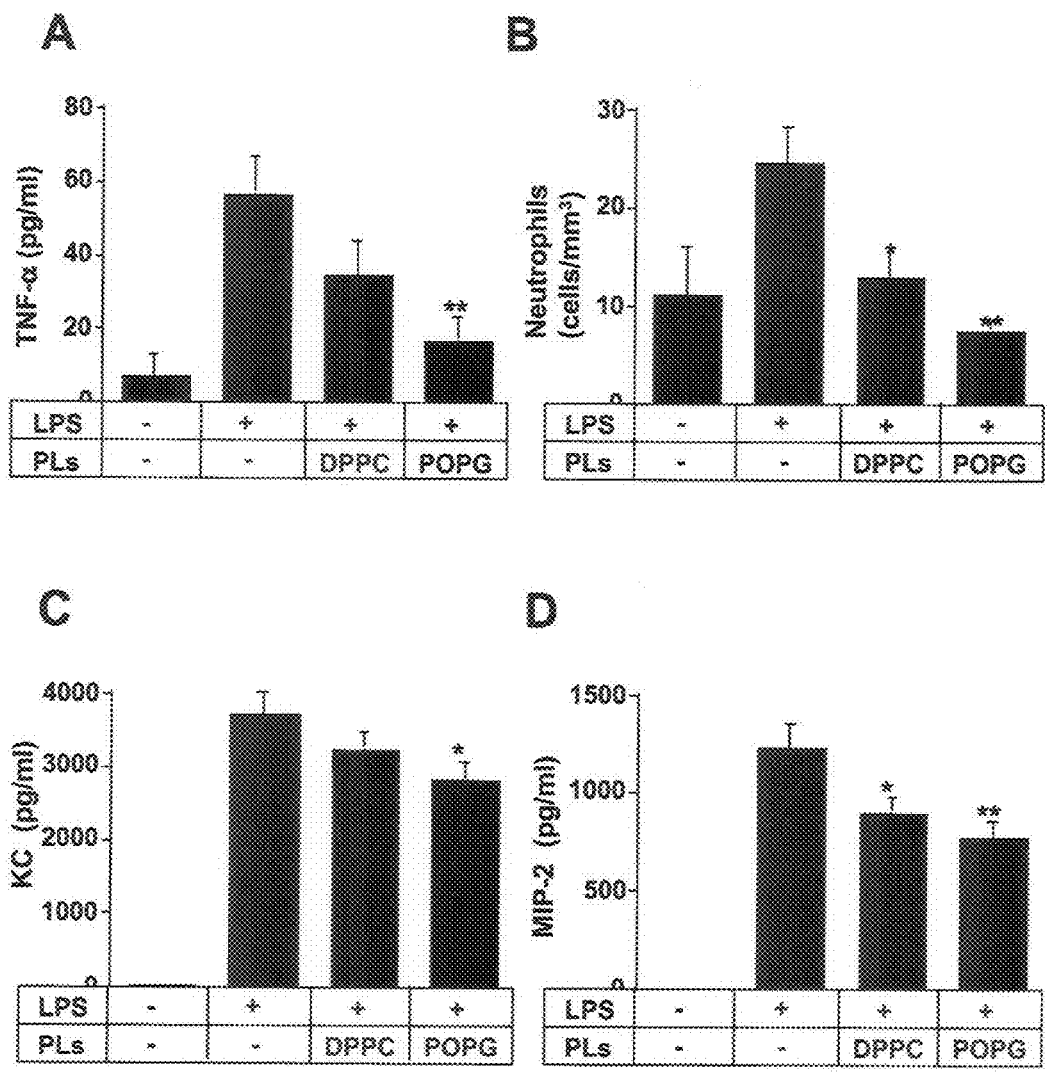
FIG. 10. Anionic phospholipids modulate lung inflammation induced by intravenously administered LPS. Phospholipids were dried under nitrogen and hydrated, and liposomes were formed using a Liposofast™. The phospholipids (50 μg) in 20 μl of PBS were sprayed into murine trachea using a MicroSprayer™ aerosolizer. At the same time, LPS (50 μg) in 200 μl of PBS was intravenously administered to mice. 3 h after stimulation, lungs were lavaged via the trachea. TNF-α production (A) was determined by ELISA. The number of leukocytes was counted and differential cell counts (B) were determined from at least 300 cells on cytocentrifuged preparations. Mouse KC (C) and MIP-2 (D) levels were determined using Quantikine kits (R&D System). The data shown are the means±S.E. for six to eight mice. Significance—*: p<0.05, **: p<0.01, when compared between LPS and LPS plus POPG.

Next, the effect of phospholipids were examined in a sepsis model in mice. LPS (50 μG/200 μl) was intravenously administered to mice via the tail vein and phospholipids were administered intratrachealy at the same time. Three hours after stimulation, BALF was collected (FIG. 10). Intratrachealy administered POPG, but not DPPC, significantly inhibited the TNF-A secretion in BALF, indicating this anionic lipid has an anti-inflammatory effect for sepsis originating outside the lung. POPG administered via the trachea, effectively inhibited the infiltration of neutrophils in BALF compared to DPPC. POPG also significantly attenuated the KC and MIP-2 levels in BALF although the magnitude of this effect was not very large. These results further indicate that POPG may be useful for treating disorders such as ALI and ARDS in the lung caused by sepsis.

POPG Blocks the Binding of BODIPY-LPS to Macrophages

Figure 11:
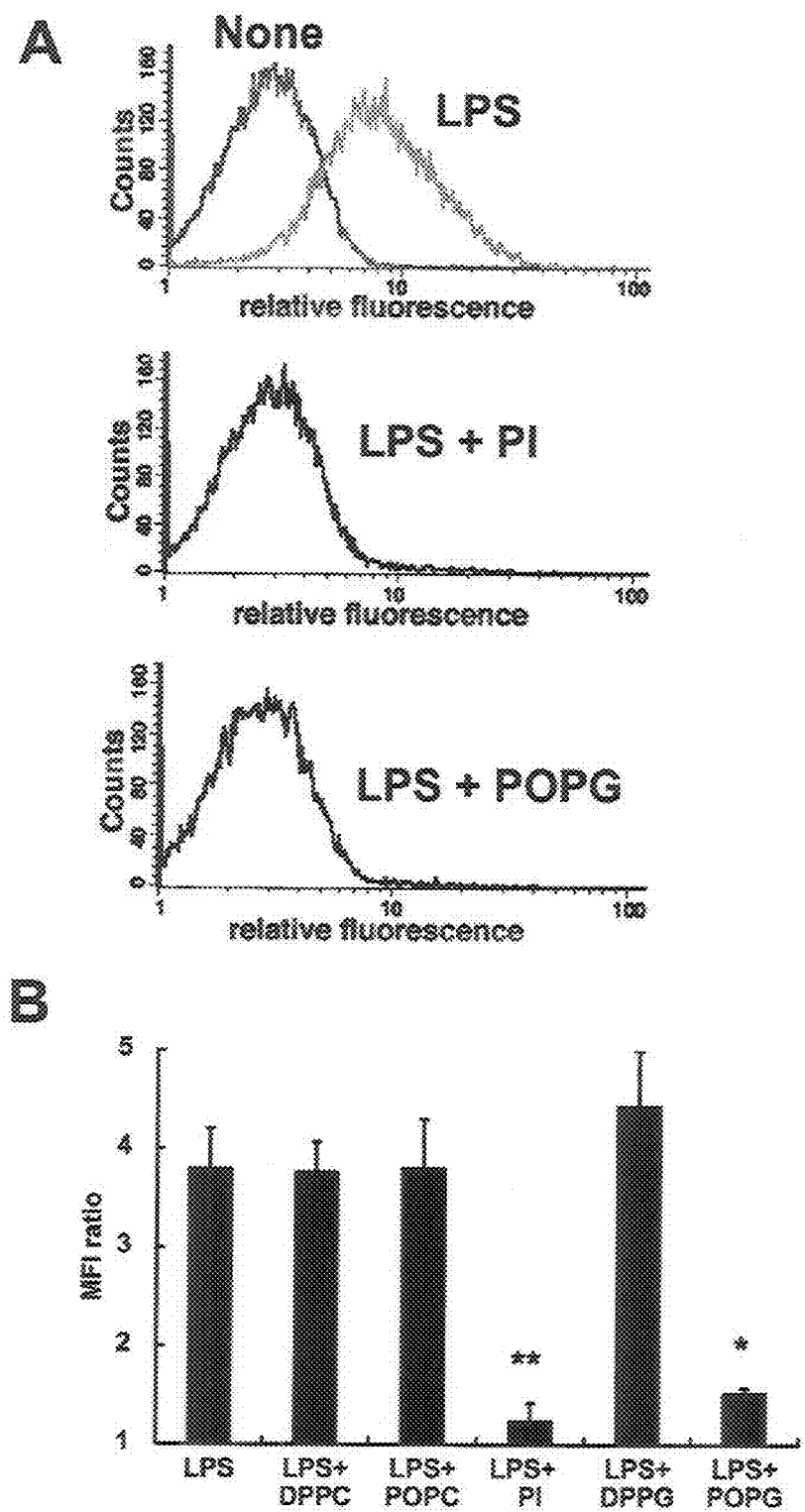
FIG. 11. Anionic phospholipids block BODIPY-LPS association with RAW264.7 macrophages. Liposomes were prepared by bath-sonication at room temperature for 30 min. RAW264.7 cells ($10^6$/tube) were incubated either without or with 1 μg/ml BODIPY-LPS in the presence or absence of liposomes (200 μg/ml) at 4° C. for 4 h. Subsequently the cells were washed by centrifugation and the cell associated fluorescence was quantified by FACScan. Panel A shows the primary data for incubation of cells without or with LPS and incubation with LPS in the presence of either PI or POPG. In panel B the mean fluorescence intensity (MFI) ratio of cells plus LPS/cells without LPS is plotted against different phospholipid treatments. Values shown in B are means±SE for three independent experiments with duplicate determinations in each experiment. Significance—*p<0.05, **p<0.01

The results described earlier in this Example in FIGS. 4 and 5 demonstrated that the antagonistic phospholipids acted upstream of kinases involved in LPS signaling. One possible site of action for the phospholipids is at the cell surface. In the experiments shown in FIG. 11A, RAW264.7 cells were incubated with fluorescent LPS at 0° C. and quantified the binding by flow cytometry. Untreated macrophages give an autofluorescent profile with a mean fluorescence intensity (MFI) of 3. Incubation of macrophages with BODIPY-LPS produces a shift in MFI to 9, indicating binding of the fluorescent ligand to the cells. Treatment of the cells with PI or POPG blocks the binding of BODIPY-LPS to the surface of the macrophages resulting in almost no increase in MFI. A summary of the findings with other phospholipids is given in FIG. 9B. The data are expressed as the MFI ratio (treated:untreated control). The results show the inhibition of BODIPY-LPS binding to the RAW cells is both phospholipid headgroup and fatty acid specific. Thus, unsaturated PI and PG antagonize LPS binding to macrophages whereas long chain saturated PG and either saturated or unsaturated species of PC are without effect.

REFERENCES FOR EXAMPLE 1

1. O'Brien, A. D., Rosenstreich, D. L., Scher, I., Campbell, G. H., MacDermott, R. P., Formal, S. B. 1980. Genetic control of susceptibility to Salmonella typhimurium in mice: role of the LPS gene. J Immunol 124:20.

2. Ulevitch, R. J., Tobias, P. S. 1995. Receptor-dependent mechanisms of cell stimulation by bacterial endotoxin. Annu Rev Immunol 13:437.

3. Wright, S. D., Ramos, R. A., Tobias, P. S., Ulevitch, R. J., Mathison, J. C. 1990. CD14, a receptor for complexes of lipopolysaccharide (LPS) and LPS binding protein. Science 249:1431.

4. Nagai, Y., Akashi, S., Nagafuku, M., Ogata, M., Iwakura, Y., Akira, S., Kitamura, T., Kosugi, A., Kimoto, M., Miyake, K. 2002. Essential role of MD-2 in LPS responsiveness and TLR4 distribution. Nat Immunol 3:667.

5. Poltorak A., H. X., Smirnova I., Liu M. Y., Van Huffel C., Du X., Birdwell D., Alejos E., Silva M., Galanos C., Freudenberg M., Ricciardi-Castagnoli P., Layton B., Beutler B. 1998. Defective LPS signaling in C3H/HeJ and C57BL/10ScCr mice: mutations in Tlr4 gene. Science 282:2085.

6. Takeda, K., Kaisho, T., Akira, S. 2003. Toll-like receptors. Annu Rev Immunol 21:335.

7. Medzhitov, R. 2001. Toll-like receptors and innate immunity. Nat Rev Immunol 1:135.

8. Barton, G. M., Medzhitov, R. 2003. Toll-like receptor signaling pathways. Science 300:1524.

9. Pattle, R. E. 1955. Properties, function and origin of the alveolar lining layer. Nature 175:1125.

10. Clements, J. A. 1957. Surface tension of lung extracts. Proc Soc Exp Biol Med 95:170.

11. King, R. J., D. J. Klass, E. G. Gikas, and J. A. Clements. 1973. Isolation of apoproteins from canine surface active material. Am J Physiol 224:788.

12. Kuroki, Y., and D. R. Voelker. 1994. Pulmonary surfactant proteins. J. Biol. Chem. 269:25943.

13. Sano, H., Kuroki, Y. 2005. The lung collectins, SP-A and SP-D, modulate pulmonary innate immunity. Mol Immunol 42:279.

14. Lawson, P. R., Reid, K. B. 2000. The roles of surfactant proteins A and D in innate immunity. Immunol Rev 173:66.

15. Sano, K., H. Sohma, T. Muta, S.-I. Nomwra, D. R. Voelker, and Y. Kuroki. 1999. Pulmonary surfactant protein A modulates the cellular response to smooth and rough lipopolysaccharide by interaction with CD14. J. Immunol. 163:387.

16. Veldhuizen, R., Nag, K., Orgeig, S., Possmayer, F. 1998. The role of lipids in pulmonary surfactant. Biochem Biophys Acta 1408:90.

17. Schmidt, R., Meier, U., Markart, P., Grimminger, F., Velcovsky, H. G., Morr, H., Seeger, W., Gunther, A. 2002. Altered fatty acid composition of lung surfactant phospholipids in interstitial lung disease. Am J Physiol Lung Cell Mol Physiol 283:1079.

18. Wright SM, H. P., Enhorning, G, Strong P, Reid K B, Holgate S T, Djukanovic R, Postle A D. 2000. Altered airway surfactant phospholipid composition and reduced lung function in asthma. J Appl Physiol 89:1283.

19. Bochkov, V. N., Kadl, A., Huber, J., Gruber, F., Binder, B. R., Leitinger, N. 2002. Protective role of phospholipid oxidation products in endotoxin-induced tissue damage. Nature 419:77.

20. Wu, Y. Z., Medjane, S., Chabot, S., Kubrusly, F. S., Raw, I., Chignard, M., Touqui, L. 2003. Surfactant protein-A and phosphatidylglycerol suppress type IIA phospholipase A2 synthesis via nuclear factor-kappaB. Am J Respir Crit Care Med 168:692.

21. Hashimoto, M., Asai, Y., Ogawa, T. 2003. Treponemal phospholipids inhibit innate immune responses induced by pathogen-associated molecular patterns. J Biol Chem 278: 44205.

22. Mueller, M., Brandenburg, K., Dedrick, R., Schromm, A. B., Seydel, U. 2005. Phospholipids inhibit lipopolysaccharide (LPS)-induced cell activation: a role for LPS-binding protein. J Immunol 172: 1091.

23. Atabai, K., Matthay, M. A. 2002. The pulmonary physician in critical care. 5: Acute lung injury and the acute respiratory distress syndrome: definitions and epidemiology. Thorax 2002.

24. Rubenfeld, G. D., Caldwell, E., Peabody, E., Weaver, J., Martin, D. P, Neff, M., Stern, E. J., Hudson, L. D. 2005. Incidence and outcomes of acute lung injury. N Engl J Med 353:1685.

25. Hawgood, S., B. J. Benson, and R. L. Hamilton, Jr. 1985. Effects of a surfactant-associated protein and calcium ions on the structure and surface activity of lung surfactant lipids. Biochemistry 24:184.

26. Kuroki, Y., R. J. Mason, and D. R. Voelker. 1988. Pulmonary surfactant apoprotein A structure and modulation of surfactant secretion by rat alveolar type II cells. J. Biol. Chem. 263:3388.

27. Rouser, G., A. N. Siakatos, and S. Fleischer. 1966. Quantitative analysis of phospholipids by thin layer chromatography and phosphorous analysis of spots. Lipids 1:85.

28. Ding, A. H., Nathan, C. F., Stuehr, D. J. 1988. Release of reactive nitrogen intermediates and reactive oxygen intermediates from mouse peritoneal macrophages. Comparison of activating cytokines and evidence for independent production. J Immunol 141:2407.

29. Hibi, M., Lin, A., Smeal, T., Minden, A., Karin, M. 1993. Identification of an oncoprotein- and UV-responsive protein kinase that binds and potentiates the c-Jun activation domain. Genes Dev 7:2135.

30. Towbin, H., T. Staehelin, and J. Gordon. 1979. Electrophoretic transfer of proteins from polyacrylamide gels to nitrocellulose sheet: Procedures and some applications. Proc Natl Acad Sci USA 76:4350.

31. Flotte, T. R., Laube, B. L. 2001. Gene therapy in cystic fibrosis. Chest 120(3 Suppl): 124S.

32. Lewis, J. F., and A. H. Jobe. 1993. Surfactant and the adult respiratory distress syndrome. Am Rev Respir Dis 147:218.

33. Akira, S., Takeda, K. 2004. Toll-like receptor signalling. Nat Rev Immunol 4:499.

34. Chen, P., Li, J., Barnes, J., Kokkonen, G. C., Lee, J. C., Liu, Y. 2002. Restraint of proinflammatory cytokine biosynthesis by mitogen-activated protein kinase phosphatase-1 in lipopolysaccharide-stimulated macrophages. J Immunol 169:6408.

35. Zhao, Q., Shepherd, E. G., Manson, M.E., Nelin, L. D., Sorokin, A., Liu, Y. 2005. The role of mitogen-activated protein kinase phosphatase-1 in the response of alveolar macrophages to lipopolysaccharide: attenuation of proinflammatory cytokine biosynthesis via feedback control of p38. J Biol Chem 280:8101.

36. Meduri, G., U, Kohler, G., Headley, S., Tolley, E., Stentz, F., Postlethwaite, A. 1995. Inflammatory cytokines in the BAL of patients with ARDS. Persistent elevation over time predicts poor outcome. *Chest* 108:1303.

37. Wuyts, A., Haelens, A., Proost, P., Lenaerts, J. P., Conings, R., Opdenakker, G., Van Damme, J. 1996. Identification of mouse granulocyte chemotactic protein-2 from fibroblasts and epithelial cells. Functional comparison with natural KC and macrophage inflammatory protein-2. *J Immunol* 157: 1736.

38. Wright, J. R. 2005. Immunoregulatory functions of surfactant proteins. *Nat Rev Immunol* 5:58.

39. Nag, K., J. Perez-Gil, M. L. Ruano, L. A. Worthman, J. Stewart, C. Casals, and K. M. Keough. 1998. Phase transitions in films of lung surfactant at the air-water interface. *Biophys J* 74:2983.

40. Honda, Y., Tsunematsu, K., Suzuki, A., Akino, T. 1988. Changes in phospholipids in bronchoalveolar lavage fluid of patients with interstitial lung diseases. *Lung* 166: 293.

41. Saydain, G., Islam, A., Afessa, B., Ryu, J. H., Scott, J. P, Peters, S. G. 2002. Outcome of patients with idiopathic pulmonary fibrosis admitted to the intensive care unit. *Am J Resp Crit. Care Med* 166:839.

42. Schmidt, R., Meier, U., Yabut-Perez, M., Walmrath, D., Grimminger, F., Seeger, W., Gunther, A. 2001. Alteration of fatty acid profiles in different pulmonary surfactant phospholipids in acute respiratory distress syndrome and severe pneumonia. *Am J Respir Crit Care Med* 163:95.

Example 2

The following experimental results describe the mechanistic basis of the surfactant lipid antagonism of LPS action. In particular, this example shows that CD14 binds POPG and PI with high affinity. The binding of POPG to CD14 almost completely inhibits the interaction of the protein with LPS. Monoclonal antibodies known to occlude the CD14 binding pocket for LPS also block the interactions of POPG and PI with CD14. In addition to binding CD14, POPG also partially inhibits the interactions between LBP and CD14. The TLR4 associated protein MD-2, which binds LPS, also binds POPG with high affinity. The phospholipid binding by MD-2 inhibits its interaction with TLR4. Although the actions of PI are similar to POPG, the principal mode of action by PI appears to be by interference in CD14 function. By comparison, POPG acts at the level of LBP, CD14 and MD-2 to suppress TLR4 signaling. These findings demonstrate a major role for POPG in human and other mammalian pulmonary surfactants as a suppressor of unwanted inflammatory events in the alveolar compartment of the lung.

Experimental Procedures

Cells and Reagents. LPS (0111:B4) purified from *Escherichia coli* was purchased from Sigma-Aldrich (St. Louis, Mo.). Phosphatidylcholine (PC), phosphatidylglycerol (PG), and phosphatidylinositol (PI) in chloroform, were purchased from Avanti Polar Lipids (Alabaster, Ala.). Recombinant human CD14, and mouse anti-CD14 monoclonal antibodies, biG2 and biG14, were purchased from Cell Sciences Inc. (Canton, Mass.). Mouse anti-CD14 monoclonal antibody MEM-18 was purchased from Exbio (Czech Republic). Mouse anti-H is antibody and HRP-conjugated mouse anti-V5 antibody were obtained from Invitrogen Life Technologies (Carlsbad, Calif.). Mouse IgG$_1$ isotype control, mouse monoclonal anti-human CD14 antibody, sheep anti-human CD14 polyclonal antibody, recombinant human LBP and goat anti-human LBP antibody were purchased from R&D systems (Minneapolis, Minn.). The macrophage-like cell line U937 (CRL-1593.2) was obtained from American Type Culture Collection (Manassas, Va.). The cells were maintained in endotoxin-free Roswell Park Memorial Institute (RPMI) 1640 medium from Cambrex (East Rutherford, N.J.) with 10% heat-inactivated bovine growth serum (BGS; Hyclone, Logan, Utah).

Soluble Extracellular Domain of TLR4 and MD-2. A soluble form of the extracellular domain of TLR4 (sTLR4) consists of the putative extracellular sequence (Met$^1$-Lys$^{631}$) and a 6 His epitope tag at its C-terminal end. sTLR4 and MD-2 cDNAs were described previously (10). sTLR4-His was subcloned into pcDNA3.1(+) (Invitrogen Life Technologies). MD-2-V5-His that contains the C-terminal fusion V5 epitope tag and 6 H is epitope tag was generated by using PCR, and subcloned into pcDNA3.1D/V5-His-TOPO (Invitrogen Life Technologies). A control protein, yeast PstB2-V5-His that contains the C-terminal fusion V5 tag epitope and 6 His tag epitope was generated by using PCR and subcloned into the baculovirus vector pVL1392 (16). The epitope tagged cDNA constructs for sTLR4 and MD-2 were subcloned into PVL1392 and in addition to PstB2 were independently expressed using a baculovirus-insect cell expression system according to the methods described by O'Reilly et al (17). The sTLR4 protein and the MD-2 protein were purified using a column of nickel-nitrilotriacetic acid beads (Qiagen, Valencia, Calif.) by the method described previously (12).

Induction of TNF-α Secretion. U937 cells were induced to differentiate by incubation in medium containing 10 nM of phorbol myristate acetate (PMA) for 48 h. The cells (1.3×10$^5$/well) were placed on 96-well plates and further incubated in the absence of PMA for 24 h in RPMI 1640 medium containing 10% BGS. After the cells were washed with PBS, the indicated concentration of phospholipids was preincubated with the cells in RPMI without serum for 30 min before adding LPS. The indicated amount of LPS was then added into the well and incubated for 6 h at 37° C. with 5% $CO_2$. The culture medium was collected and assayed for TNF-α secretion using an ELISA kit (Invitrogen).

Binding of CD14 and MD-2 to Phospholipids. Phospholipids (1.25 nmole) in 20 µl aliquots of ethanol were pipeted onto 96-well half-area plates (Corning Inc., Corning, N.Y.), and the solvent evaporated using a warm air blower. After nonspecific binding was blocked with 20 mM Tris buffer (pH 7.4) containing 0.15 M NaCl, 5 mM $CaCl_2$ or 2 mM EGTA, and 5% (wt/vol) BSA (buffer A), various concentrations of human CD14 or MD-2 in 25 µl of buffer A were added and incubated at 37° C. for 1 h. The wells were then washed with 20 mM Tris buffer (pH 7.4) containing 0.15 M NaCl and 5 mM $CaCl_2$ or 2 mM EGTA (buffer B), and 1 µg/ml anti-human CD14 IgG or anti-His antibody (50 µl/well) in buffer A was added and incubated overnight at 4° C., followed by the incubation with horseradish peroxidase (HRP)-labeled anti-mouse IgG (1:5000) for 1 h. After washing the wells with buffer B, the peroxidase reaction was finally performed using o-phenylenediamine as a substrate. The binding of CD14 or MD-2 to phospholipids was detected by measuring absorbance at 490 nm.

Binding of LPS to CD14. LPS (2 µg) in 20 µl aliquots of ethanol was pipeted onto a 96-well plate, and the solvent evaporated using a warm air dryer. After the nonspecific binding was blocked with buffer A, mixtures of CD14 (1 µg/ml) and phospholipid liposomes (20 µg/ml) in buffer A, which were preincubated at 37° C. for 1 h, were added and further incubated at 37° C. for 1 h. The amount of bound CD14 was detected using the method described above.

Phospholipid Competition for LBP-CD14 Binding and MD-2-sTLR4 Binding. CD14 (2 µg) or sTLR4 (100 ng) in aliquots of 20 µl of buffer B were pipeted onto a 96-well plate, and the solvent evaporated using a warm air dryer. After the nonspecific binding was blocked with buffer A, the mixtures of LBP and phospholipid liposomes or the mixture of MD-2 (1 µg/ml) and phospholipid liposomes in buffer A were added and incubated at 37° C. for 1 h. The amount of bound LBP or MD-2 was detected using specific antibodies.

Statistical Analysis. All results were expressed as mean±S.E. ANOVA was used to determine the levels of difference between all groups. Groups were compared by unpaired two-tailed t-test. The p-value for significance was set at 0.05.

Results

CD14 Binds POPG and PI in a Concentration Dependent Manner.

Figure 12:
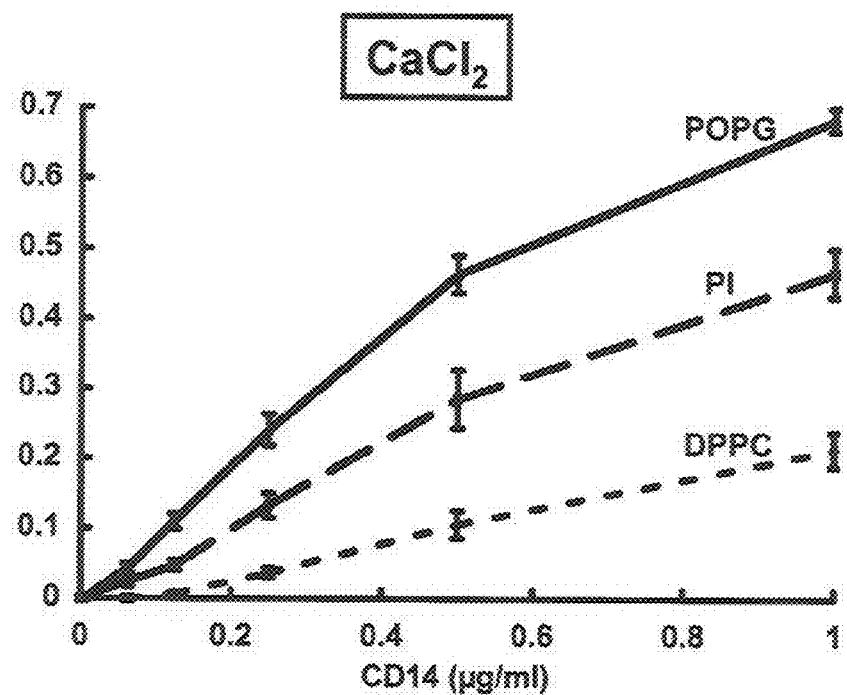
FIG. 12. CD14 binds to solid phase lipids. Phospholipids (1.25 nmole) in 20 μl of ethanol were placed onto microtiter wells and the solvent was evaporated. Nonspecific binding was blocked with 20 mM Tris buffer (pH 7.4) containing 0.15 M NaCl, 5 mM $CaCl_2$ (in the upper panel) or 2 mM EGTA (in the lower panel), and 5% (wt/vol) BSA (buffer A). Varying concentrations of human CD14 in buffer A were added and incubated at 37° C. for 1 h. The binding of CD14 to phospholipids was detected using anti-CD14 monoclonal antibody as described under "Experimental Procedures." The data shown are the means±S.E. from three separate experiments with duplicate samples in each experiment.
Figure 12:
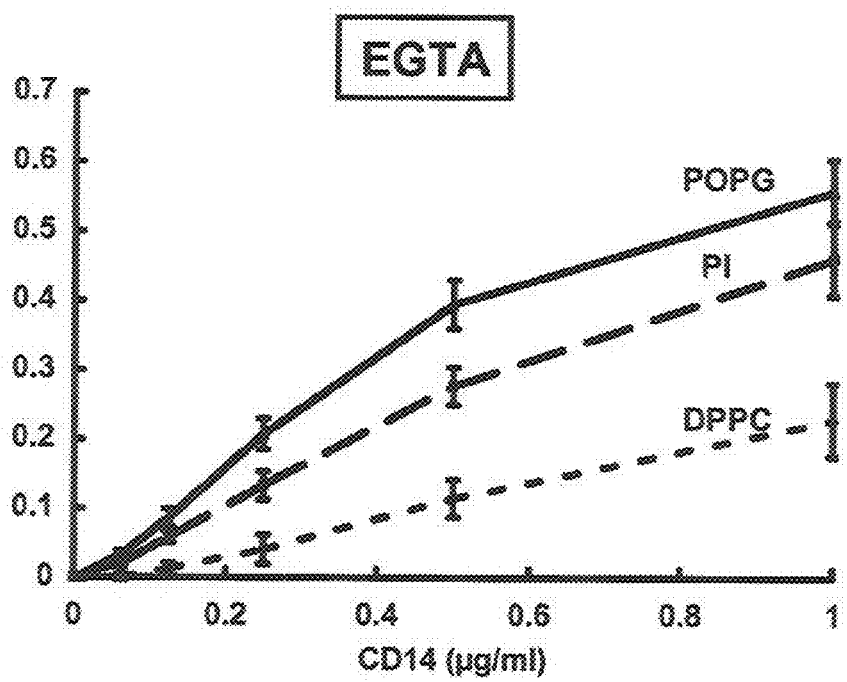
Figure 13:
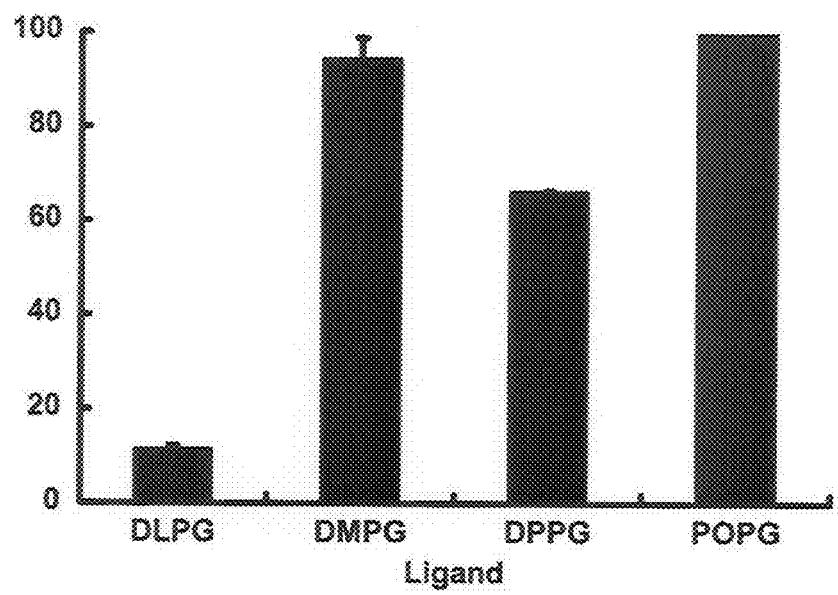
FIG. 13. PG Inhibits CD14 binding to solid phase LPS. (A) Various types of PG were coated onto microtiter plates, and incubated with CD14 (1 μg/ml) at 37° C. for 1 h. The binding of CD14 to PG was detected using anti-CD14 monoclonal antibody, and the ELISA based absorbance of CD14 bound to POPG was defined as 100%. Types of PG shown on the graph are: dilauroylphosphatidylglycerol (DLPG), dimyristoyl-phosphatidylglycerol (DMPG), dipalmitoylphosphatidylglycerol (DPPG), and 16:0/18:1; palmitoyl-oleoyl-phosphatidylglycerol (POPG). (B) LPS (2 μg) in 20 μl of ethanol was placed onto microtiter wells and the solvent was evaporated. After blocking the nonspecific binding with buffer A, the mixture of CD14 (1 μg/ml) and phospholipid liposomes (20 μg/ml) in buffer A, which were preincubated at 37° C. for 1 h, were added and incubated at 37° C. for 1 h. The binding of CD14 to LPS was detected using anti-CD14 monoclonal antibody. The ELISA based absorbance of CD14 bound to LPS was defined as 100%. The data shown are the means±S.E. from three separate experiments with duplicate samples in each experiment. *: p<0.05, **: p<0.01, when compared with LPS-CD14 binding in the absence of phospholipids.
Figure 13:
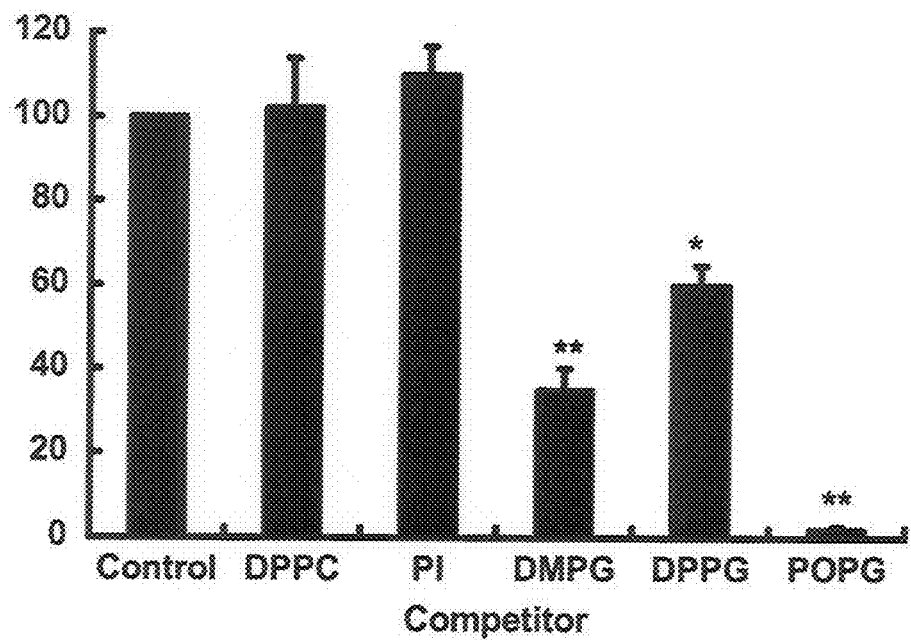

LPS mainly binds to CD14 on cell surfaces, and is subsequently transferred to an MD-2/TLR4 complex on the same membrane to initiate signaling. We investigated whether CD14 is a target for phospholipid interaction that antagonizes LPS action. The anionic surfactant lipids POPG and PI, adsorbed as a solid phase to microtiter wells, strongly bound to CD14 in a concentration dependent manner (FIG. 12). The binding of CD14 to the zwitterionic surfactant lipid, DPPC, was significantly less (approximately 30%) than the levels of POPG binding. These interactions were not attenuated by EGTA indicating that $CaCl_2$ was not required for the binding. These results demonstrate that POPG and PI can directly bind CD14 and these interactions are of higher affinity that those with DPPC. These binding interactions for the anionic phospholipids are consistent with the effect of these same lipids upon inflammatory mediator production, and fluorescent LPS binding to macrophages, described in the accompanying paper. The molecular species of PG were also evaluated for their direct binding interactions with CD14. POPG and DMPG exhibited the strongest direct binding interactions with CD14. However, CD14 also bound to DPPG to nearly the same extent as POPG and DMPG (FIG. 13A). These results clearly indicate that anti-inflammatory anionic phospholipids can bind strongly to CD 14. However, some lipids without demonstrable anti-inflammatory effect also will directly bind CD14.

POPG Blocks the Interaction of CD14 with LPS

Another method to evaluate CD14-lipid interaction is to perform competition experiments in which CD14 binding to LPS is subjected to competition using phospholipids. This series of experiments is described in FIG. 13B. Two lipids that function as potent LPS antagonists in vitro and vivo, DMPG and POPG, are the most effective inhibitors of CD14 binding to solid phase LPS. DPPG, which is inactive as an LPS antagonist, weakly competes for CD14 binding to LPS. These latter findings are consistent with earlier findings about PG antagonism of LPS activation of macrophages. Paradoxically, PI, which is a potent LPS antagonist fails to compete for CD14 binding to solid phase LPS. These latter results strongly suggest that PI and POPG do not act by identical mechanisms in producing LPS antagonism.

POPG and PI Bind to CD14 at the LPS Binding Site.

CD14 has four LPS binding sites located at the N-terminus of the protein (18). Monoclonal antibodies biG14 and MEM-18 recognize aa39-44 and aa57-64, respectively, that constitute part of the LPS binding site. The biG14 and MEM-18 antibodies are also proven inhibitors of LPS-binding to CD14. Another antibody, biG2, recognizes aa147-152, which is not part of the LPS binding site, and biG2 ligation does not inhibit LPS-binding to CD14. The epitope for another antibody, RDIg, has not been determined, but appears to recognize a site distinct from that used for LPS binding. Recent solution of the crystal structure of mouse CD14 at a resolution of 2.5 Å provides evidence that LPS binds a defined pocket in the protein (19). The biG14 and MEM-18 binding sites are close to the pocket and predicted to stearically occlude LPS binding. In contrast, the biG2 site when ligated by antibody should not interfere with LPS binding. The inventors examined the action of the above-described monoclonal antibodies to determine the relationship between the LPS binding site and the anionic phospholipid binding site on CD 14.

Figure 14:
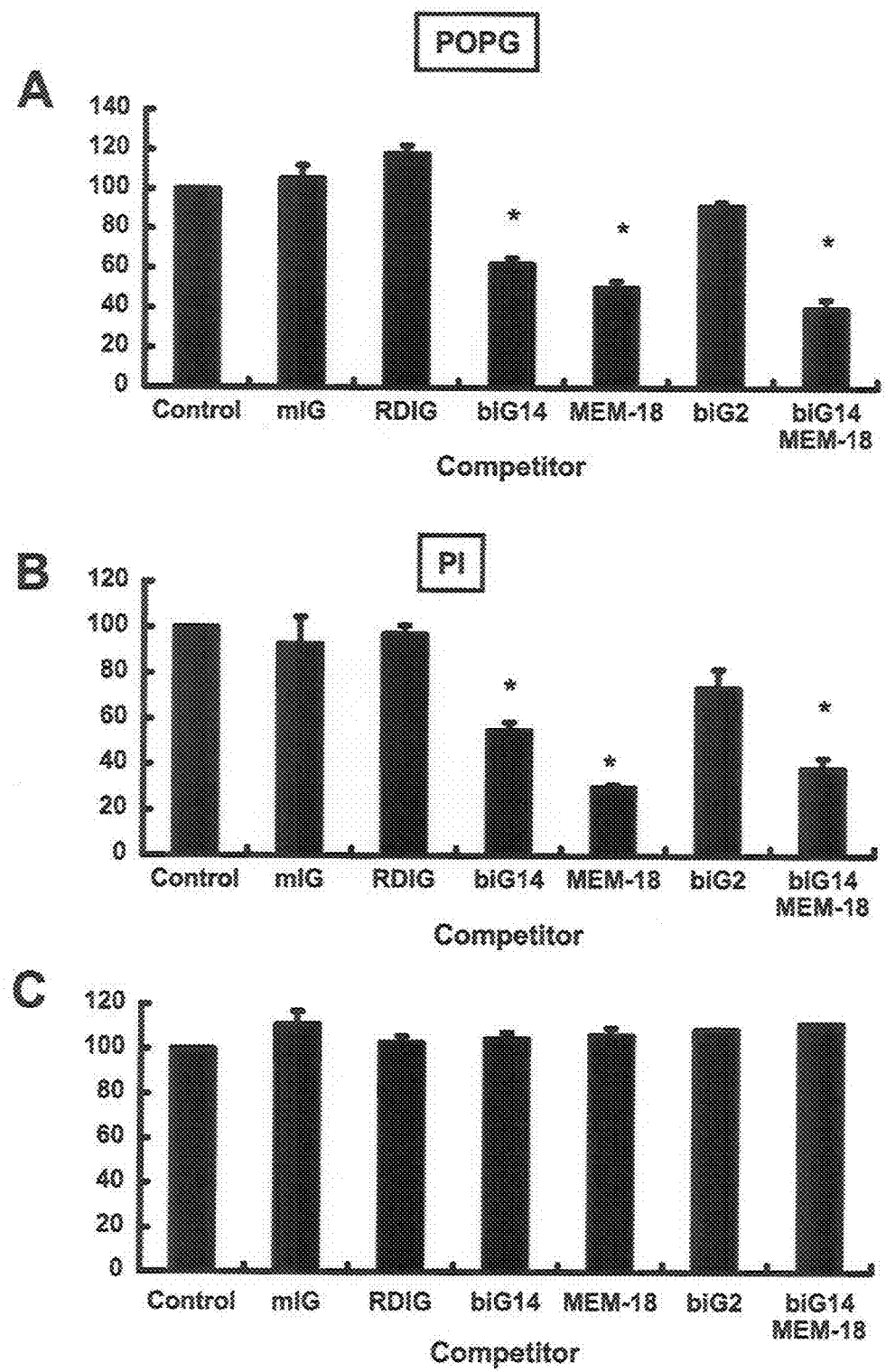
FIG. 14. Monoclonal antibodies specific for the LPS binding site inhibit CD14 interaction with POPG and PI. POPG (A) or PI (B) were coated onto microtiter plates. After blocking the nonspecific binding with buffer A, the mixture of CD14 (1 μg/ml) and monoclonal antibodies or isotype control IgG (50 μg/ml) in buffer A, which were preincubated at 37° C. for 1 h, were added and incubated at 37° C. for 1 h. The binding of CD14 to phospholipids was detected using sheep anti-CD14 polyclonal antibody, and the ELISA based absorbance of CD14 bound to phospholipid was defined as 100%. The data shown are the means±S.E. from three separate experiments with duplicate samples in each experiment. *: p<0.05, when compared with CD14-binding in the absence of monoclonal antibody. (C) CD14 (2 μg) was coated onto microtiter plates and nonspecific binding was blocked with buffer A. Monoclonal antibodies or isotype control IgG (50 μg/ml) in buffer A were added and incubated at 37° C. for 1 h. The CD14 was detected using sheep anti-CD14 polyclonal antibody, and the ELISA based absorbance of solid phase CD14 alone was defined as 100%.

In these experiments, the CD14 was preincubated with specific monoclonal antibodies and the effect of this interaction upon the recognition of solid phase phospholipid by CD14 was measured. The CD14 bound to the solid phase was detected using anti-CD14 polyclonal antibody. As shown in FIG. 14A, the monoclonal antibodies biG14 and MEM-18 significantly reduced the CD14 binding to solid phase POPG by 40-60%, whereas other antibodies that did not recognize the LPS binding site (mouse IG, RDIg and biG2), failed to significantly alter CD14 recognition of POPG. The addition of biG14 and MEM-18 antibodies together gave slightly higher inhibition of CD14 binding to lipid than either antibody alone. Nearly identical results were obtained when PI was used as the solid phase ligand as shown in FIG. 14B, with the monoclonal antibodies inhibiting the binding reaction by 40-70%. Interestingly, none of the antibodies tested inhibited the binding of CD14 to DPPG (data not shown). Thus, the site of interaction between CD14 and POPG and PI, is different from the site of interaction with DPPG. In FIG. 14C the inventors conducted control experiments with solid phase CD14 to show that ligation of the protein by RDIg, biG14, MEM-18 and biG2 does not attenuate the binding of anti-CD14 polyclonal antibody. Thus the loss of polyclonal antibody detection of CD 14 reflects a reduction in interaction of the protein with phospholipids, and is not due to monoclonal antibody interference with polyclonal antibody recognition.

Anionic Surfactant Phospholipids Inhibit LPS-Induced TNF-α Production in the Absence of LBP.

Figure 15:
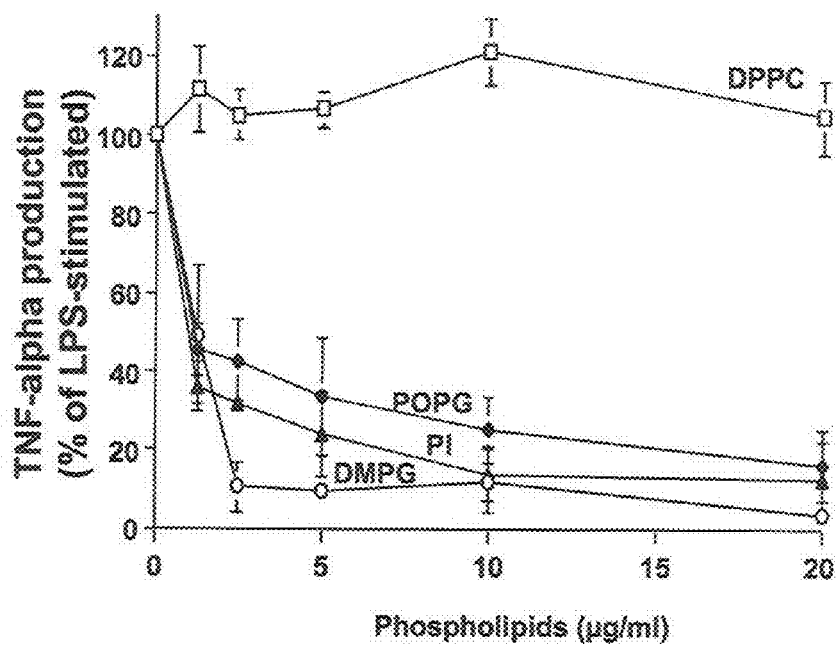
FIG. 15. Anionic phospholipid antagonism of LPS action does not require LBP. (A) 10 ng/ml of LPS and different concentrations of liposomes were added to monolayer cultures of differentiated U937 cells in RPMI without serum. After 6 h of stimulation, media were collected and TNF-α production was determined by ELISA. LPS stimulation without phospholipid was defined as 100%. (B) CD14 (2 µg) was adsorbed onto microtiter wells. After blocking nonspecific binding with buffer A, the mixture of LBP (1 µg/ml) and phospholipid liposomes (20 µg/ml) in buffer A, which were preincubated at 37° C. for 1 h, was added and further incubated at 37° C. for 1 h. The binding of LBP to CD14 was detected using anti-LBP polyclonal antibody. The ELISA based absorbance of LBP bound to CD14 was defined as 100%. The data shown are the means±S.E. from three separate experiments with duplicate samples in each experiment. *: $p<0.05$, when compared with CD14-LBP binding in the absence of phospholipids.
Figure 15:
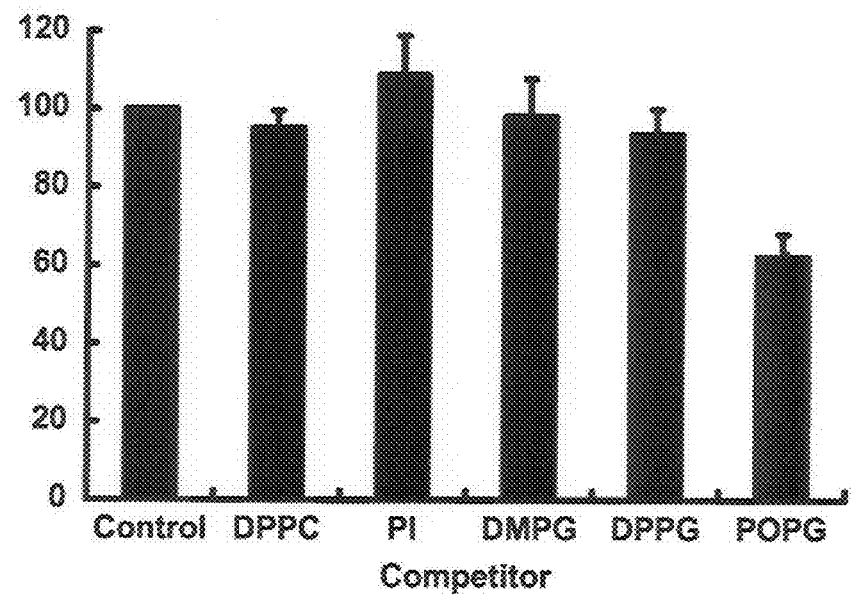

LBP is a serum LPS binding protein that facilitates the interaction of LPS with CD14. As a component situated upstream of TLR4 signal transduction, LBP constitutes another potential target for anionic lipids. The inventors next investigated whether surfactant phospholipids were associated with LBP action. When U937 macrophages were stimulated with LPS in serum free media, LPS-induced synthesis and secretion of TNF-α was still inhibited by POPG, DMPG, and PI (FIG. 15A). These results demonstrate that anionic phospholipids can work as LPS antagonists in the absence of LBP. In situations without LBP, the potency of POPG and PI is modestly diminished, but the potency of DMPG as an LPS antagonist continues to remain high. Although these experiments demonstrate that LBP is not required for lipid antagonism of LPS action, they do not address the question of whether direct interactions between LBP and CD14 can be disrupted by anionic lipids. To investigate this latter issue, solid phase CD 14 were prepared and the activity of anionic lipids as competitors for LBP binding was examined. The findings presented in FIG. 15B demonstrate that POPG can significantly reduce the interaction of LBP with CD14 by approximately 40%. This inhibitory action of POPG was not exhibited by any other molecular species of PG tested or PI or DPPC. These findings show that POPG acts at more than one step in altering host recognition of LPS and distinguishes the action of this lipid from the other antagonistic lipids.

POPG Binds to MD-2 and Blocks the Interaction of MD-2 with sTLR4.

Figure 16:
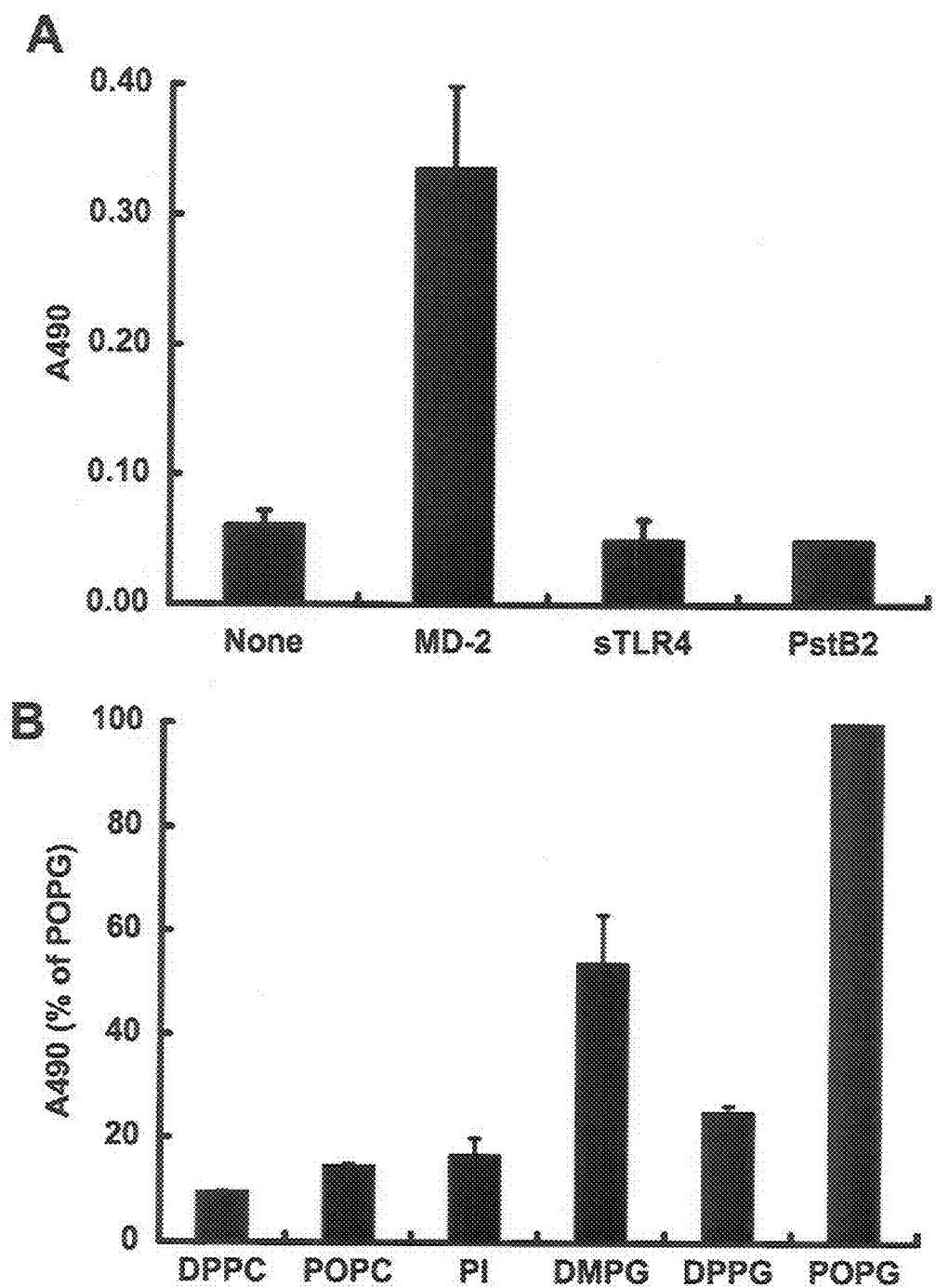
FIG. 16. MD-2 preferentially binds POPG. (A) POPG (1.25 nmole) was placed onto microtiter wells and the solvent evaporated. After blocking nonspecific binding with buffer A, MD-2, sTLR4 and PstB2 (1 µg/ml) in buffer A were added and incubated at 37° C. for 1 h. The binding of recombinant proteins to POPG was detected using anti-His antibody. (B) Phospholipids (1.25 nmole) were placed onto microtiter wells and the solvent evaporated. After blocking, MD-2 (1 µg/ml) in buffer A was added and incubated at 37° C. for 1 h. The binding of MD-2 to phospholipids was detected using anti-His antibody. The ELISA based absorbance of MD-2 bound to POPG was defined as 100%. The data shown are the means±S.E. from three separate experiments each with duplicate determinations.

TLR4 requires MD-2 for CD14-dependent cellular response to LPS. It is known that LPS binds to CD14 and MD-2, but not TLR4. Next, the inventors examined whether phospholipids directly interact with MD-2 or TLR4. Recombinant MD-2, sTLR4 and the yeast protein PstB2, all with a (His)$_6$ epitope tag, were expressed using the baculovirus-insect cell expression system. Solid phase POPG, strongly bound to MD-2, but not sTLR4 or the control epitope tagged protein PstB2 (FIG. 16A). The lipid recognition specificity of MD-2 was evaluated using PI, two molecular species of PC and three molecular species of PG (FIG. 16B). Relative to POPG, only DMPG showed significant binding (ca 50% of the POPG value) to MD-2. Neither saturated nor unsaturated PC, nor unsaturated PI, nor DPPG showed any significant binding to MD-2.

Figure 17:
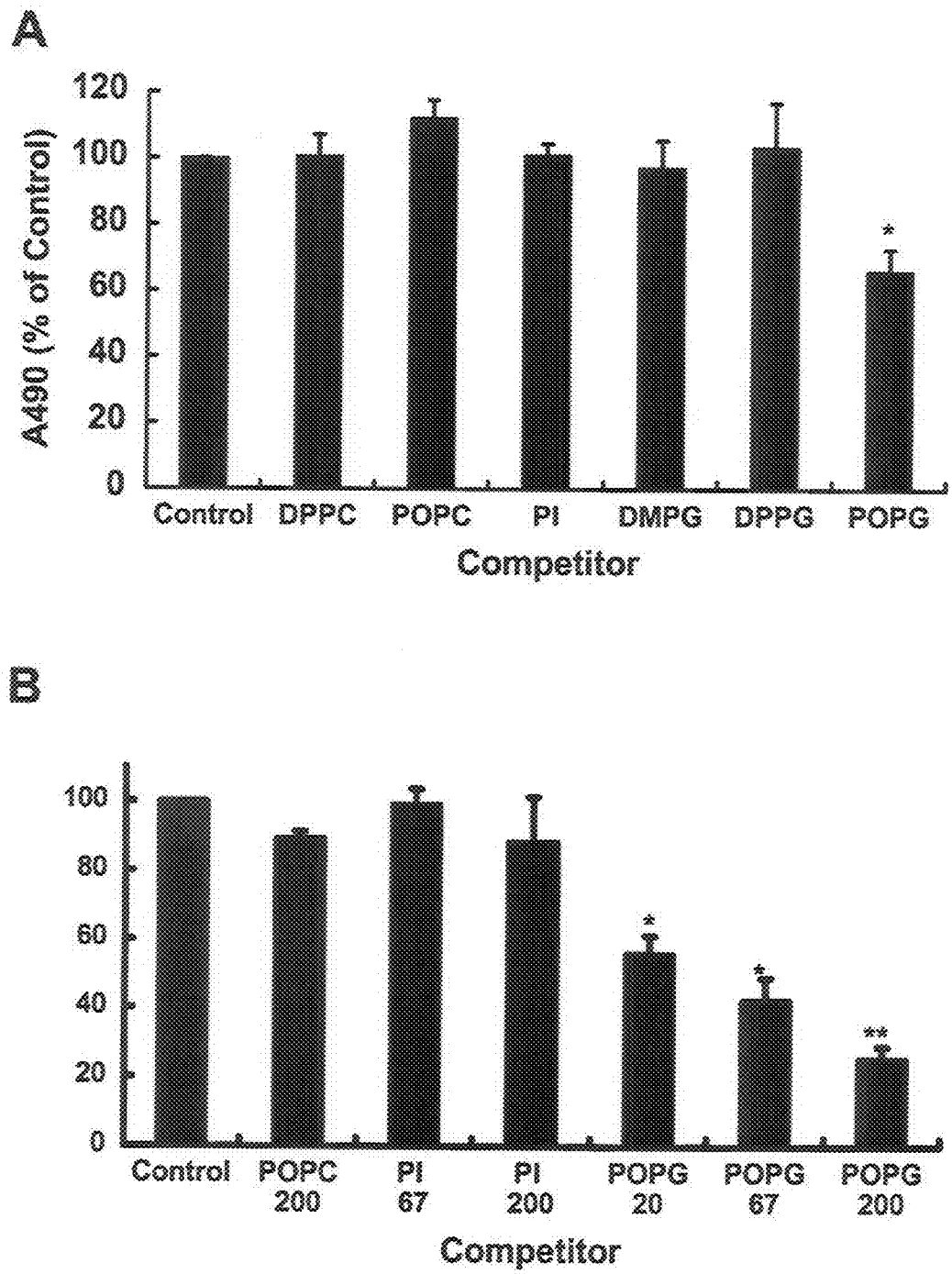
FIG. 17. POPG disrupts MD-2 interaction with TLR4. sTLR4 (100 ng) was adsorbed onto microtiter wells. After blocking nonspecific binding with buffer A, the mixture of MD-2 (1 µg/ml) and phospholipid liposomes (20 µg/ml) (A) or different concentrations of phospholipids (B) in buffer A, which were preincubated at 37° C. for 1 h, was added and incubated at 37° C. for 2 h. The binding of MD-2 to sTLR4 was detected using HRP-conjugated anti-V5 monoclonal antibody. The ELISA based absorbance of MD-2 binding without phospholipids was defined as 100%. The data shown are the means+S.E. from three separate experiments each with duplicate determinations. *: $p<0.05$, **: $p<0.01$, when compared with MD-2-sTLR4 binding in the absence of phospholipids.

The inventors next probed the influence of lipids upon the interactions between MD-2 and TLR4. The extracellular domain of TLR4 was adsorbed onto microtiter wells, and the direct binding of MD-2 was measured by ELISA, using a monoclonal antibody directed against a V5 epitope on the protein. At low levels of lipid competitor, only POPG interfered with the MD-2/TLR4 interaction (FIG. 17A) producing 40% inhibition. In FIG. 17B the concentration of lipid competitors was varied up to 200 µg/ml and only POPG showed any significant inhibition (approximately 75%) of the MD-2/TLR4 interaction. The action of POPG as an inhibitor increased with increasing concentration of the lipid between 20-200 µg/ml. These results clearly demonstrate that another site of action of POPG occurs between MD-2 and TLR4. These results further indicate that PI and POPG have non-identical mechanisms of interaction with the innate immune system that result in suppression of inflammation.

REFERENCES FOR EXAMPLE 2

1. O'Brien, A. D., Rosenstreich, D. L., Scher, I., Campbell, G. H., MacDermott, R. P., Formal, S. B. 1980. Genetic control of susceptibility to *Salmonella typhimurium* in mice: role of the LPS gene. *J Immunol* 124:20.
2. Ulevitch, R. J., Tobias, P. S. 1995. Receptor-dependent mechanisms of cell stimulation by bacterial endotoxin. *Annu Rev Immunol* 13:437.
3. Miller, S. I., R. K. Ernst, and M. W. Bader. 2005. LPS, TLR4 and infectious disease diversity. *Nat Rev Microbiol* 3:36.
4. Clements, J. A. 1957. Surface tension of lung extracts. *Proc Soc Exp Biol Med* 95:170.
5. Wright, S. D., Ramos, R. A., Tobias, P. S., Ulevitch, R. J., Mathison, J. C. 1990. CD14, a receptor for complexes of lipopolysaccharide (LPS) and LPS binding protein. *Science* 249:1431.
6. Poltorak A., H. X., Smirnova I., Liu M. Y., Van Huffel C., Du X., Birdwell D., Alejos E., Silva M., Galanos C., Freudenberg M., Ricciardi-Castagnoli P., Layton B., Beutler B. 1998. Defective LPS signaling in C3H/HeJ and C57BL/10ScCr mice: mutations in Tlr4 gene. *Science* 282:2085.
7. Nagai, Y., Akashi, S., Nagafuku, M., Ogata, M., Iwakura, Y., Akira, S., Kitamura, T., Kosugi, A., Kimoto, M., Miyake, K. 2002. Essential role of MD-2 in LPS responsiveness and TLR4 distribution. *Nat Immunol* 3:667.
8. Shimazu, R., S. Akashi, H. Ogata, Y. Nagai, K. Fukudome, K. Miyake, and M. Kimoto. 1999. MD-2, a molecule that confers lipopolysaccharide responsiveness on Toll-like receptor 4. *J Exp Med* 189:1777.
9. Viriyakosol, S., P. S. Tobias, R. L. Kitchens, and T. N. Kirkland. 2001. MD-2 binds to bacterial lipopolysaccharide. *J Biol Chem* 276:38044.
10. Hyakushima, N., H. Mitsuzawa, C. Nishitani, H. Sano, K. Kuronuma, M. Konishi, T. Himi, K. Miyake, and Y. Kuroki. 2004. Interaction of soluble form of recombinant extracellular TLR4 domain with MD-2 enables lipopolysaccharide binding and attenuates TLR4-mediated signaling. *J Immunol* 173:6949.
11. Gioannini, T. L., A. Teghanemt, D. Zhang, N. P. Coussens, W. Dockstader, S. Ramaswamy, and J. P. Weiss. 2004. Isolation of an endotoxin-MD-2 complex that produces Toll-like receptor 4-dependent cell activation at picomolar concentrations. *Proc Natl Acad Sci USA* 101:4186.
12. Sano, H., H. Chiba, D. Iwaki, H. Sohma, D. R. Voelker, and Y. Kuroki. 2000. Surfactant proteins A and D bind CD14 by different mechanisms. *J Biol Chem* 275:22442.
13. Sano, K., H. Sohma, T. Muta, S.-I. Nomwra, D. R. Voelker, and Y. Kuroki. 1999. Pulmonary surfactant protein A modulates the cellular response to smooth and rough lipopolysaccharide by interaction with CD14. *J. Immunol.* 163:387.
14. Shepherd, V. L. 2002. Distinct roles for lung collectins in pulmonary host defense. *Am J Respir Cell Mol Biol* 26:257.
15. Hashimoto, M., Asai, Y., Ogawa, T. 2003. Treponemal phospholipids inhibit innate immune responses induced by pathogen-associated molecular patterns. *J Biol Chem* 278:44205.
16. Wu, W. I., S. Routt, V. A. Bankaitis, and D. R. Voelker. 2000. A new gene involved in the transport-dependent metabolism of phosphatidylserine, PSTB2/PDR17, shares sequence similarity with the gene encoding the phosphatidylinositol/phosphatidylcholine transfer protein, SEC14. *J. Biol. Chem.* 275:14446.
17. O'Reilly, D. R., L. K. Miller, and V. A. Luckow. 1992. In *Baculovirus Expression Vectors. A Laboratory Manual.* W.H. Freeman and Company, New York, p. 109.
18. Viriyakosol, S., Kirkland, T. N. 1995. A region of human CD14 required for lipopolysaccharide binding. *J Biol Chem* 270:361.
19. Kim, J. I., Lee, C. J., Jin, M. S. Lee, C. H., Paik, S. G., Lee, H., Lee, J. O. 2005. Crystal structure of CD14 and its implications for lipopolysaccharide signaling. *J Biol Chem* 280:11347.
20. Cunningham, M. D., R. A. Shapiro, C. Seachord, K. Ratcliffe, L. Cassiano, and R. P. Darveau. 2000. CD14 employs hydrophilic regions to "capture" lipopolysaccharides. *J Immunol* 164:3255.
21. Mueller, M., Brandenburg, K., Dedrick, R., Schromm, A. B., Seydel, U. 2005. Phospholipids inhibit lipopolysaccharide (LPS)-induced cell activation: a role for LPS-binding protein. *J Immunol* 172: 1091.
22. Inohara, N., and G. Nunez. 2002. ML—a conserved domain involved in innate immunity and lipid metabolism. *Trends Biochem Sci* 27:219.
23. Rubenfeld, G. D., Caldwell, E., Peabody, E., Weaver, J., Martin, D. P, Neff, M., Stern, E. J., Hudson, L. D. 2005. Incidence and outcomes of acute lung injury. *N Engl J Med* 353: 1685.

Example 3

This example demonstrates that various anionic surfactant lipids inhibit the activity of toll-like receptors.

Figure 18:
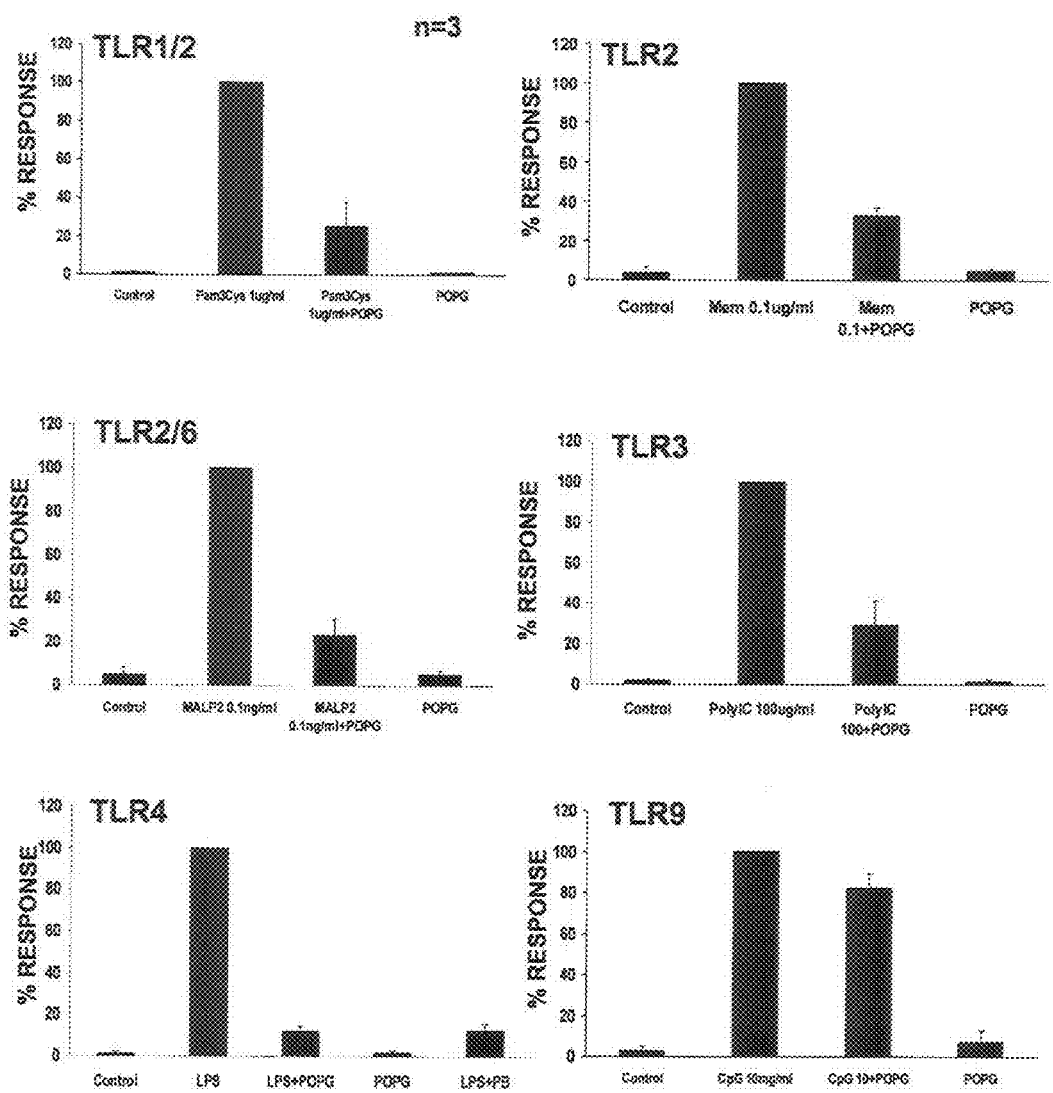
FIG. 18 is a graph showing TNFα production with TLR agonists and POPG antagonism in RAW264.7 at 24 hr.

FIG. 18 illustrates the results described below, and demonstrates that unsaturated phosphatidylglycerol (POPG) antagonizes the activation of multiple Toll-like receptors (TLRs) in RAW 264.7 cells. In this experiment, multiple TLRs were stimulated with defined TLR agonists for 24 h and the TNFα production was measured. In each case, the maximal stimulation by agonist is set at 100% and the antagonism by POPG is expressed as the relative % response. The Controls consist of no treatment, or treatment with POPG in the absence of agonist as indicated. The agonists for the TLRs consist of Pam3Cys for TLR½, *Mycoplasma pneumoniae* membranes as an agonist for TLR2, mycoplasma derived MALP2 as an agonist for TLR ⅔, double stranded RNA (poly IC) for TLR3, Gram-negative lipopolysaccharide for TLR4, and CpG rich DNA as an agonist for TLR9. The TLR4 panel also contains the antagonist polymyxin B (PB) for comparison with POPG. The TLR9 agonist serves as a negative control to show that the action of POPG is not non-specific for antagonism of all TLR signaling. As shown in FIG. 18, POPG inhibits the activity of TLR1, TLR2, TLR3, TLR4, and TLR6, but not TLR9.

Figure 19:
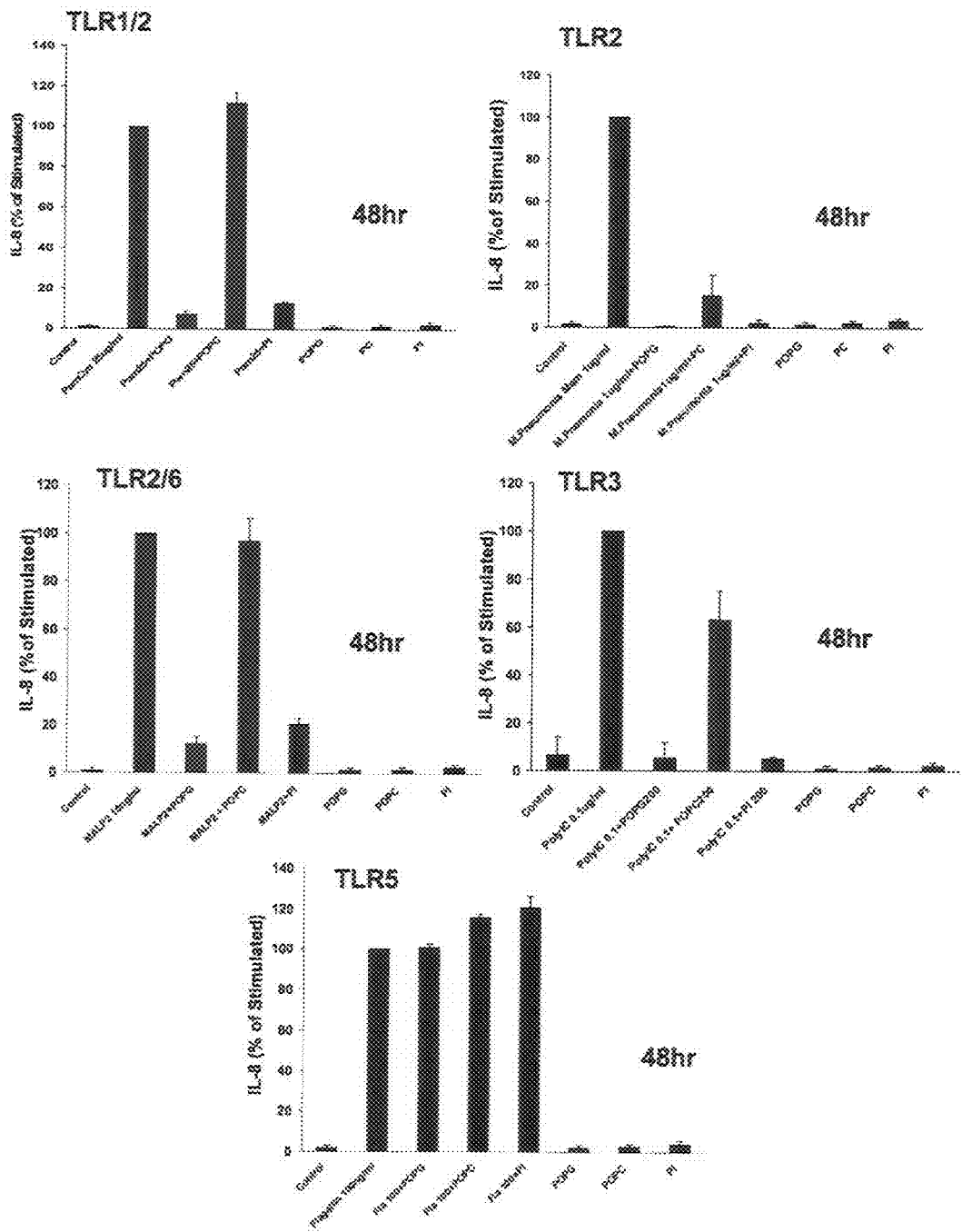
FIG. 19 is a graph showing IL-8 production with TLR agonists and POPG antagonism in Beas2B epithelial cells.

FIG. 19 illustrates the results of the experiment described below, and demonstrates that unsaturated phosphatidylglycerol (POPG) and phosphatidylinositol (PI) antagonize the action of multiple Toll-like receptors (TLRs) on BEAS2B epithelial cells. In this experiment, multiple TLRs were stimulated with defined TLR agonists for 48 h, and the IL-8 production was measured. In each case, the maximal stimulation by agonist is set at 100% and the antagonism by POPG or PI is expressed as the relative % response. The Controls consist of no treatment, or treatment with POPG, or phosphatidylcholine (POPC), or phosphatidylinositol (PI), in the absence of agonist as indicated. The agonists for the TLRs consist of Pam3Cys for TLR½, *Mycoplasma pneumoniae* membranes as an agonist for TLR2, *Mycoplasma fermentans* derived MALP2 as an agonist for TLR ⅔, double stranded RNA (poly IC) for TLR3, and bacterial flagellin (Fla) as an agonist for TLR5. The TLR5 agonist serves as a negative control to show that the action of POPG is not non-specific for antagonism of all TLR signaling. As shown in FIG. 19, POPG and PI inhibit the activity of TLR1, TLR2, TLR3, and TLR6, but not TLR5.

Figure 20:
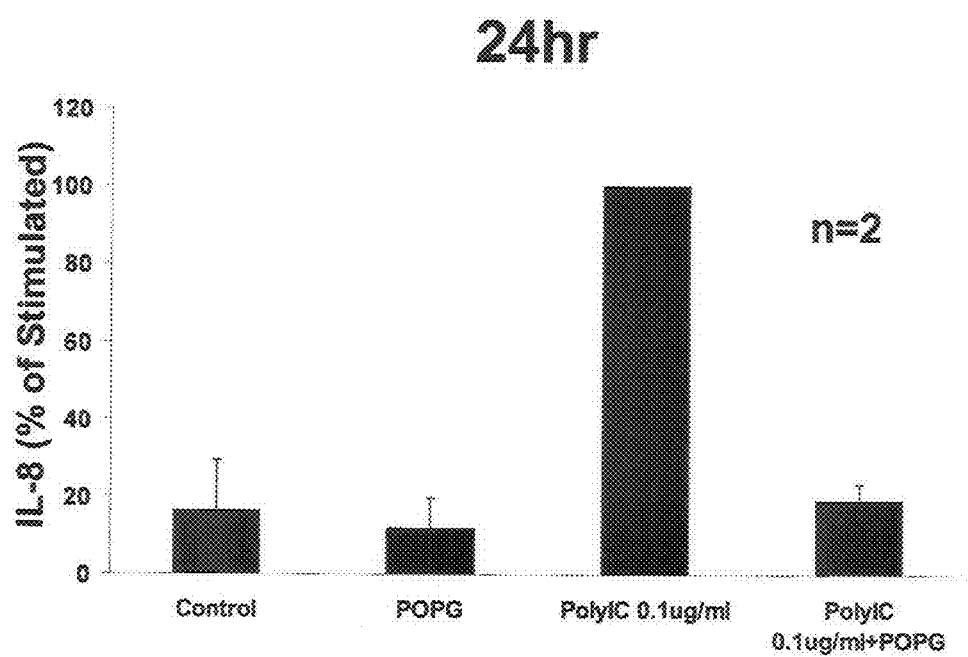
FIG. 20 is a graph showing IL-8 production in NHBE with polyIC and POPG.

FIG. 20 illustrates the results of the experiment described below, and shows that unsaturated phosphatidylglycerol (POPG) antagonizes the action of Toll-like receptor 3 on primary normal human bronchial epithelial (NHBE) cells. In this experiment, NHBE cells were stimulated with double stranded RNA (polyIC) and the IL-8 production was measured after an interval of 24 hr. The maximal stimulation by agonist is set at 100% and the antagonism by POPG is expressed as the relative % response. The Controls consist of no treatment, or treatment with POPG, in the absence of agonist as indicated. As shown in FIG. 20, POPG inhibits the activity of TLR3.

Figure 21:
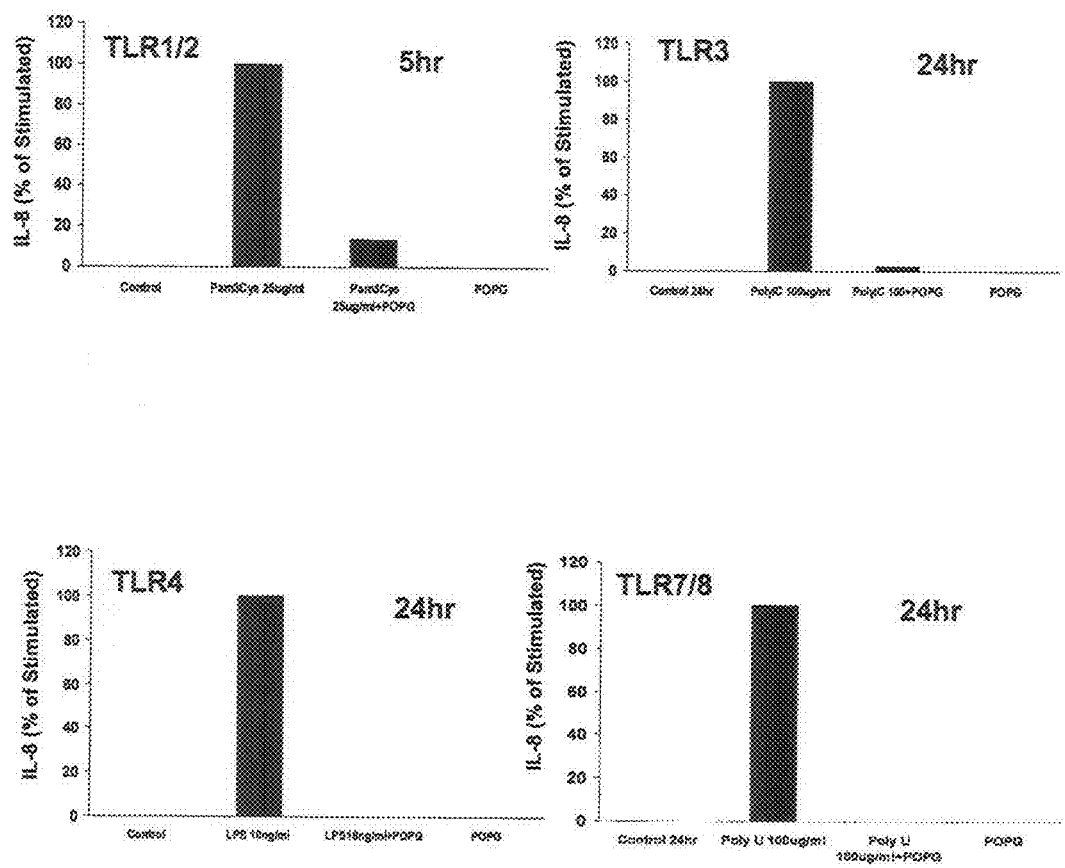
FIG. 21 is a graph showing IL-8 production in human neutrophils and its antagonism by POPG.

FIG. 21 illustrates the results of the experiment described below, and demonstrates that unsaturated phosphatidylglycerol (POPG) antagonizes the action of multiple Toll-like receptors (TLRs) on primary human neutrophils. In this experiment, multiple TLRs were stimulated with defined TLR agonists for 5-24 h as indicated, and the IL-8 production was measured. In each case the maximal stimulation by agonist is set at 100% and the antagonism by POPG is expressed as the relative % response. The Controls consist of no treatment, or treatment with POPG, in the absence of agonist as indicated. The agonists for the TLRs consist of Pam3Cys for TLR½, double stranded RNA (poly IC) for TLR3, Gram-negative lipopolysaccharide (LPS) for TLR4, and single stranded RNA (polyU) for TLR⅞. As shown in FIG. 21, POPG inhibits the activity of TLR1, TLR2, TLR3, TLR4, TLR7 and TLR8.

Example 4

This example demonstrates that unsaturated phosphatidyl glycerol (PG), such as POPG, inhibit respiratory syncytial virus (RSV) infection.

Figure 22:
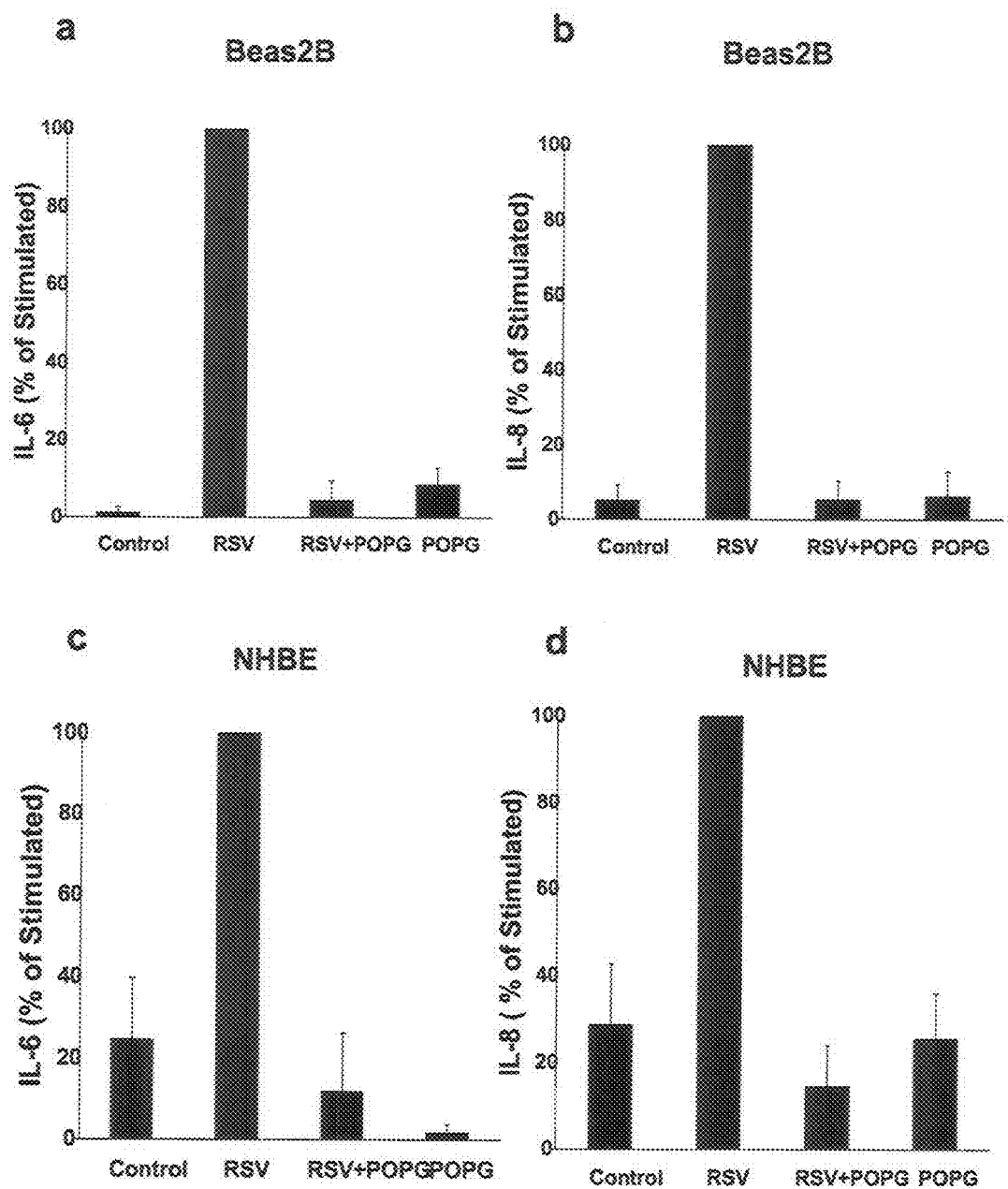
FIG. 22 is a graph showing that unsaturated phosphatidylglycerol (POPG) inhibits IL-6 and IL-8 production by BEAS2B and normal human bronchial epithelial (NHBE) challenged by infection with Respiratory Syncytial Virus (RSV).

Referring to FIG. 22, this experiment demonstrates that unsaturated phosphatidylglycerol (POPG) inhibits IL-6 and IL-8 production by BEAS2B and normal human bronchial epithelial (NHBE) challenged by infection with Respiratory Syncytial Virus (RSV). Monolayers of BEAS2B and NHBE cells were infected with RSV at a multiplicity of 3 for 48 h. Infections were performed on cells in either the absence or the presence of POPG (200 ug/ml). Media were harvested 48 h after viral challenge and assayed for the presence of IL-6 and IL-8 by ELISA. Controls consisted of no viral challenge in either the presence or absence of POPG as indicated.

Figure 23:
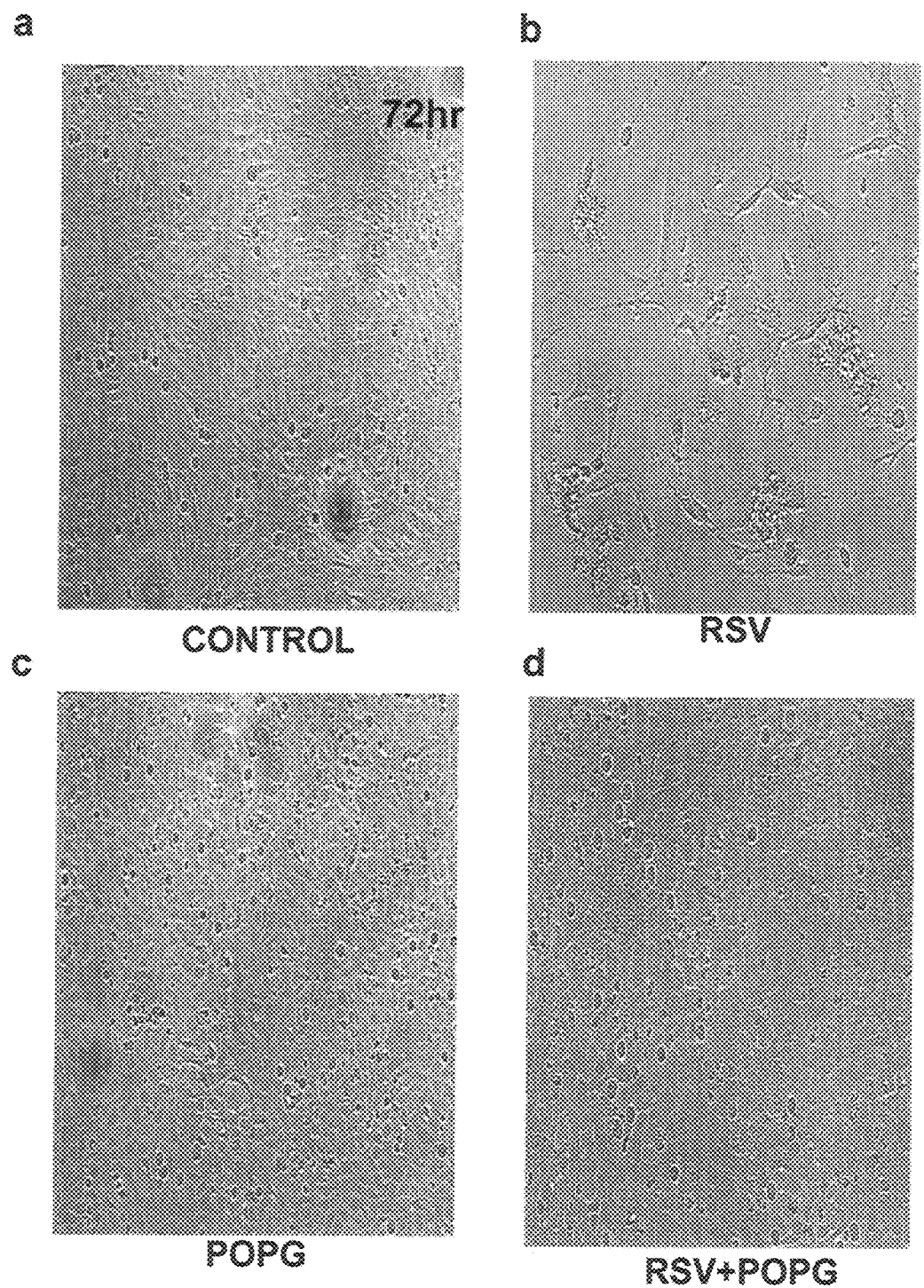
FIG. 23 is a digital image showing that unsaturated phosphatidylglycerol (POPG) prevents the cytopathic effects of RSV upon BEAS2B cells.

Referring to FIG. 23, this experiment shows that unsaturated phosphatidylglycerol (POPG) prevents the cytopathic effects of RSV upon BEAS2B cells. Monolayers of BEAS2B cells were infected with RSV at a multiplicity of 3 for 72 h. Infections were performed on cells in either the absence or the presence of POPG (200 ug/ml). The cell monolayers were photographed at a magnification of 200×. Controls consisted of no viral challenge in either the presence or absence of POPG as indicated.

Figure 24:
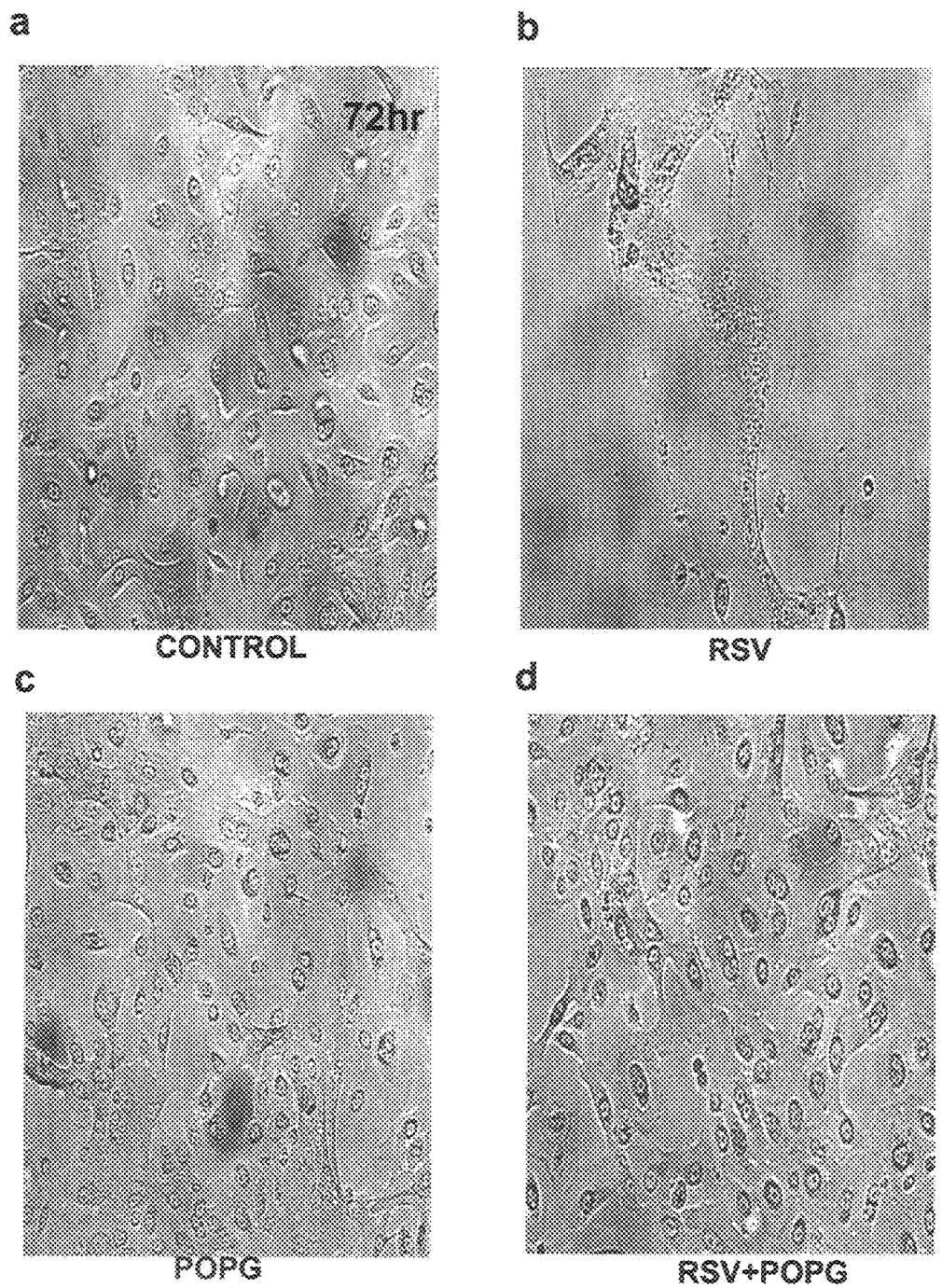
FIG. 24 is a digital image showing that unsaturated phosphatidylglycerol (POPG) prevents the cytopathic effects of RSV upon NHBE cells.

Referring to FIG. 24, this experiment shows that unsaturated phosphatidylglycerol (POPG) prevents the cytopathic effects of RSV upon NHBE cells. Monolayers of NHBE cells were infected with RSV at a multiplicity of 3 for 72 h. Infections were performed on cells in either the absence or the presence of POPG (200 ug/ml). The cell monolayers were photographed at a magnification of 200×. Controls consisted of no viral challenge in either the presence or absence of POPG as indicated.

Figure 25:
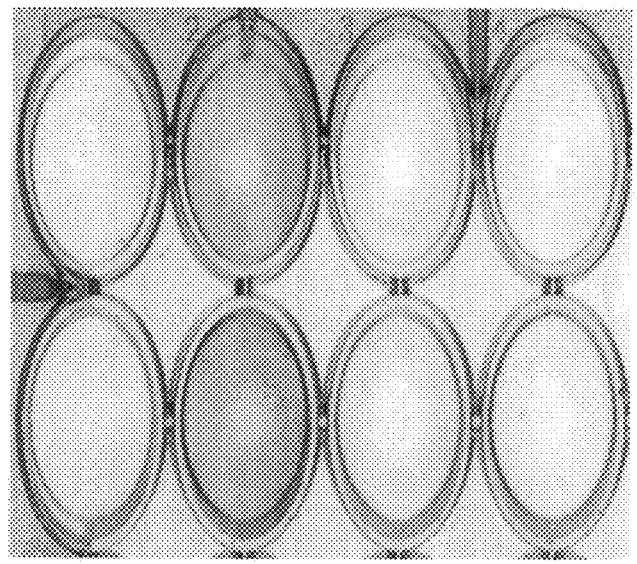
FIG. 25 is a digital image showing that unsaturated phosphatidylglycerol (POPG) prevents viral replication in BEAS2B and NHBE cells.
Figure 25:
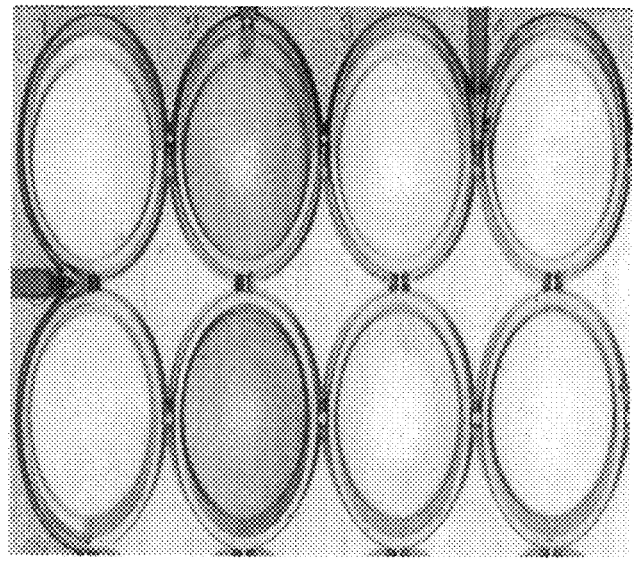

Referring to FIG. 25, this experiment shows that unsaturated phosphatidylglycerol (POPG) prevents viral replication in BEAS2B and NHBE cells. Monolayers of BEAS2B and NHBE cells were infected with RSV at a multiplicity of 3 for 72 h. Infections were performed on cells in either the absence or the presence of POPG (200 ug/ml). The cell monolayers were fixed and stained with goat anti-human RSV antibody conjugated with horseradish peroxidase. The presence of the antibody was detected with diaminobenzamidine. Controls consisted of cell layers not exposed to the virus or exposed to POPG in the absence of virus as indicated.

Figure 26:
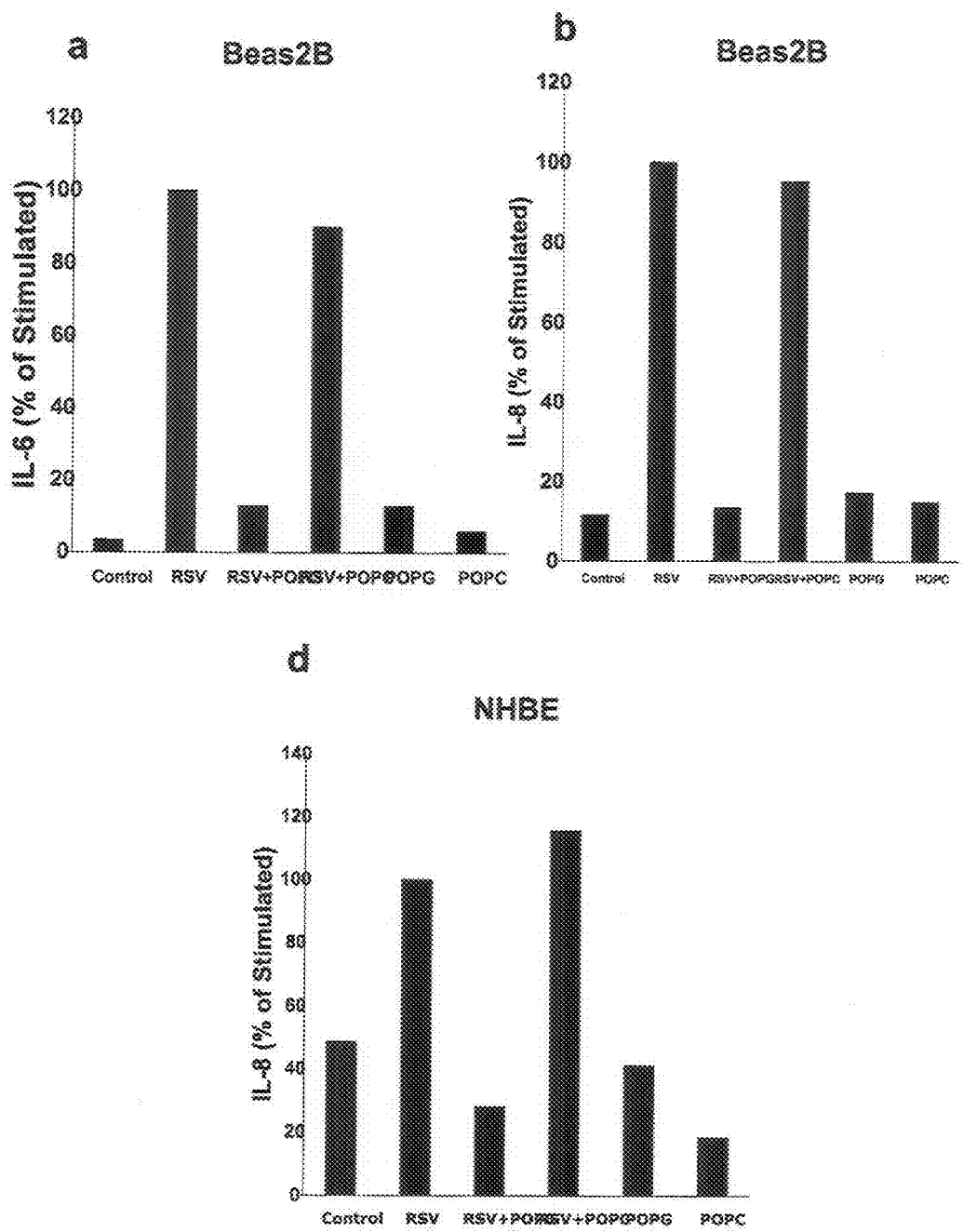
FIG. 26 is a graph showing that unsaturated phosphatidylglycerol (POPG), but not unsaturated phosphatidylcholine (POPC) inhibits cytokine production in BEAS2B and NHBE cells challenged with RSV.

Referring to FIG. 26, this experiment demonstrates that unsaturated phosphatidylglycerol (POPG), but not unsaturated phosphatidylcholine (POPC) inhibits cytokine production in BEAS2B and NHBE cells challenged with RSV. Monolayers of BEAS2B and NHBE cells were infected with RSV at a multiplicity of 3 for 48 h. Infections were performed on cells in either the absence or the presence of POPG (200 ug/ml) and POPC (200 ug/ml). Media were harvested 48 h after viral challenge and assayed for the presence of IL-6 and IL-8 by ELISA. Controls consisted of no viral challenge in either the presence or absence of POPG; or the presence or absence of POPC, as indicated.

Figure 27:
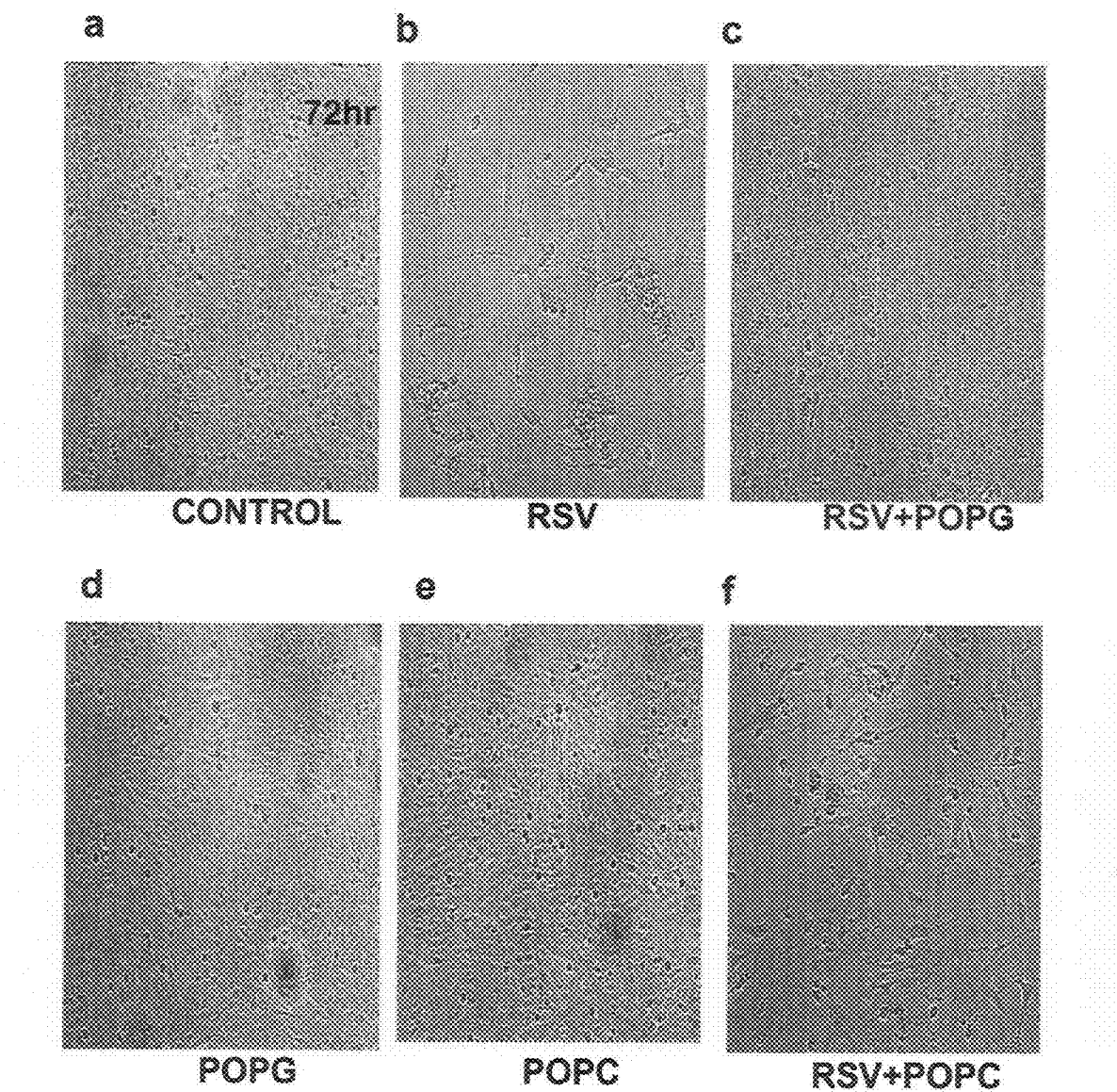
FIG. 27 is a digital image showing that unsaturated phosphatidylglycerol (POPG), but not unsaturated phosphatidylcholine (POPC) prevents the cytopathic effects of RSV upon BEAS2B cells.

Referring to FIG. 27, this experiment shows that unsaturated phosphatidylglycerol (POPG), but not unsaturated phosphatidylcholine (POPC), prevents the cytopathic effects of RSV upon BEAS2B cells. Monolayers of BEAS2B cells were infected with RSV at a multiplicity of 3 for 72 h. Infections were performed on cells in either the absence (b) or the presence (c,f) of POPG (200 ug/ml) and POPC (200 ug/ml) as indicated. Cells were photographed at a magnification of 200×. Controls (a,d,e) consisted of cell layers either not exposed to virus or exposed to POPG, and POPC in the absence of virus as indicated.

Figure 28:
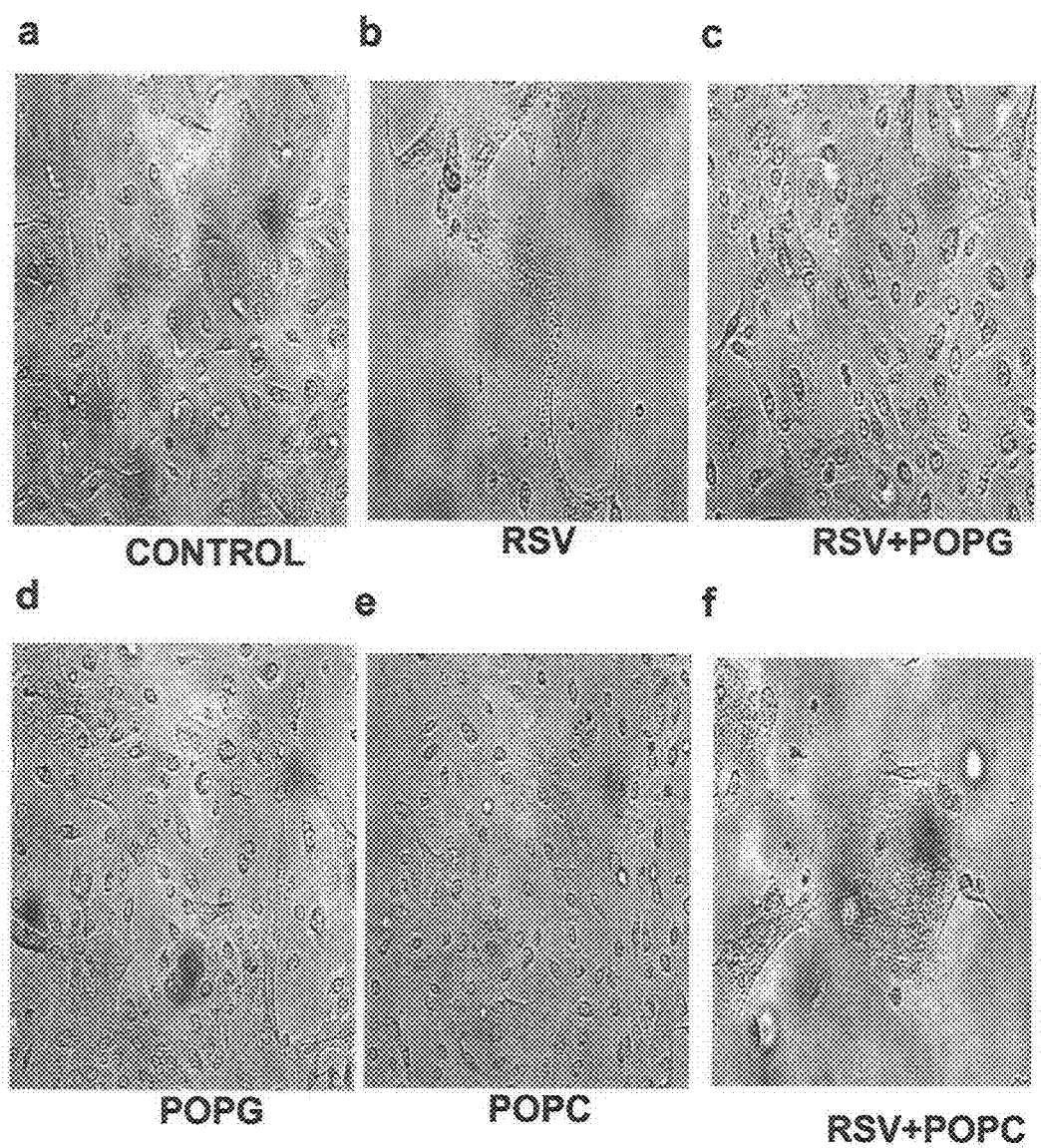
FIG. 28 is a digital image showing that unsaturated phosphatidylglycerol (POPG), but not unsaturated phosphatidylcholine (POPC), prevents the cytopathic effects of RSV upon NHBE cells.

Referring to FIG. 28, this experiment shows that unsaturated phosphatidylglycerol (POPG), but not unsaturated phosphatidylcholine (POPC), prevents the cytopathic effects of RSV upon NHBE cells. Monolayers of NHBE cells were infected with RSV at a multiplicity of 3 for 72 h. Infections were performed on cells in either the absence (b) or the presence (c,f) of POPG (200 ug/ml) and POPC (200 ug/ml) as indicated. Cells were photographed at a magnification of 200×. Controls (a,d,e) consisted of cell layers either not exposed to virus or exposed to POPG, and POPC in the absence of virus as indicated.

Example 5

Figure 29:
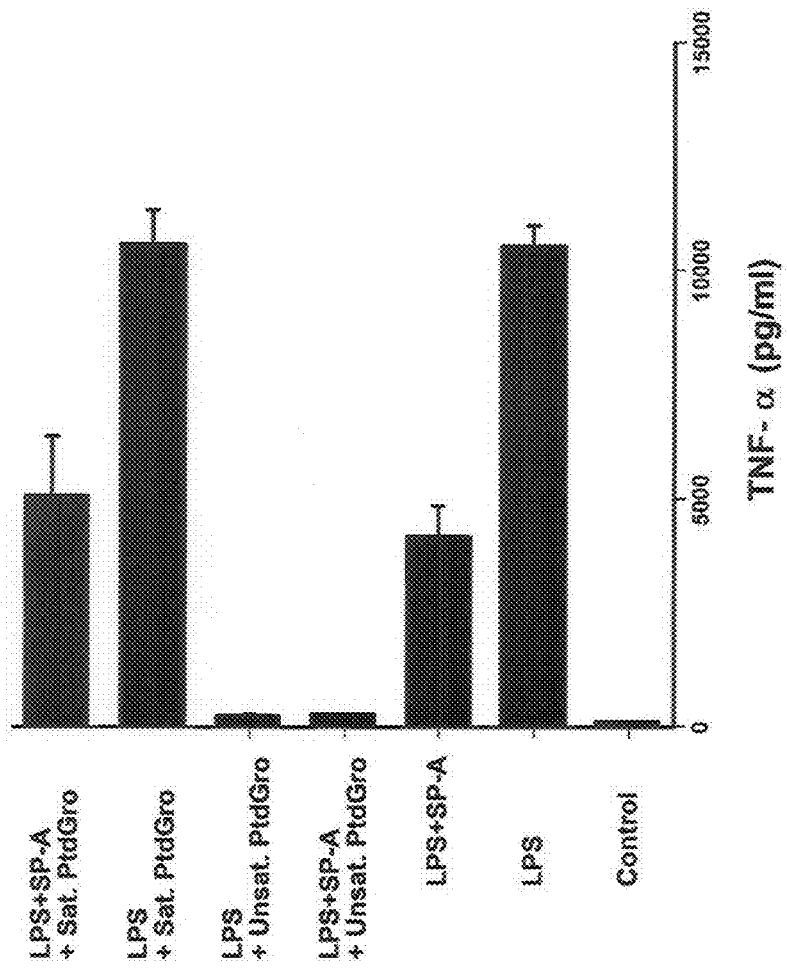
FIG. 29 shows that saturated PtdGro does not block the anti-inflammatory effects of SP-A upon macrophages stimulated with LPS, and unsaturated-PtdGro exerts potent anti-inflammatory effects on these macrophages.

This example demonstrates that saturated PtdGro does not block the anti-inflammatory effects of SP-A upon macrophages stimulated with LPS, and unsaturated-PtdGro exerts potent anti-inflammatory effects on these macrophages. U937 macrophages were stimulated with 100 ng/ml smooth LPS for 6 hours. The culture medium was harvested and assayed for the presence of TNFα by ELISA. Control cultures received no additions. SP-A was added as indicated at 10 μg/ml. Saturated-(16:0/16:0)-PtdGro was added at 20 μg/ml. Unsaturated-(18:1/18:1)-PtdGro was added at 20 μg/ml. FIG. 29 shows the TNFα levels.

Example 6

This example demonstrates that the inhibitory effect of phosphatidylglycerols on LPS-induced inflammatory mediator production is molecular species specific.

Figure 30:
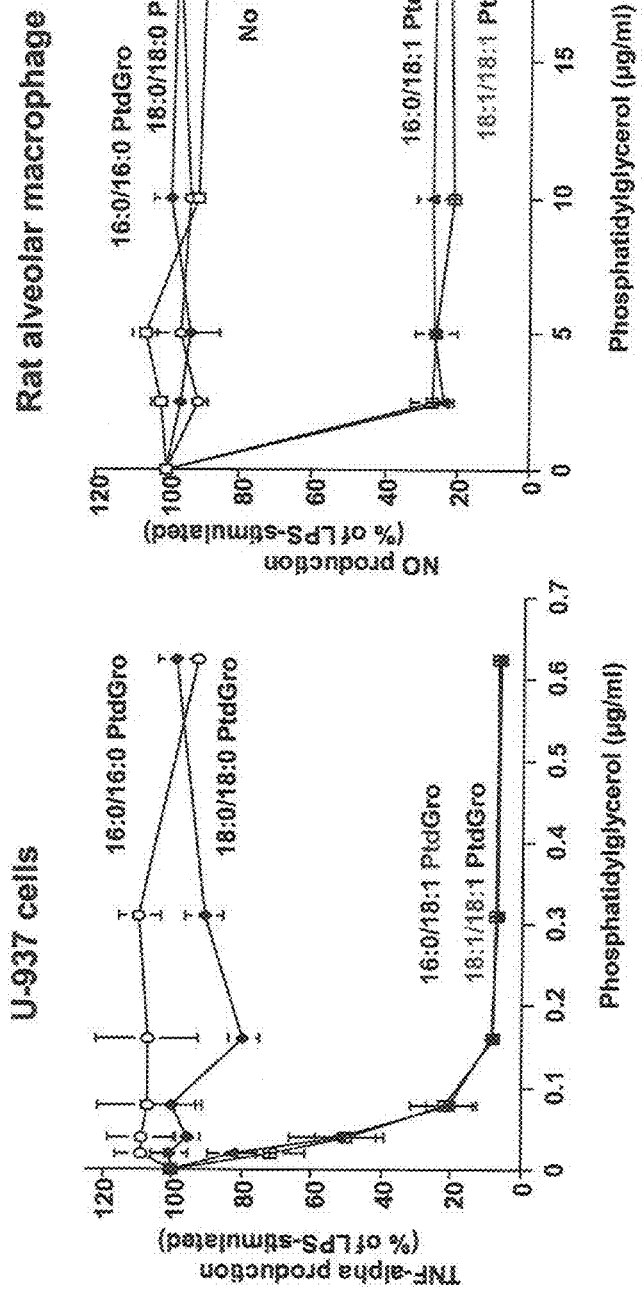
FIG. 30 shows that the inhibitory effect of phosphatidylglycerols on LPS-induced inflammatory mediator production is molecular species specific.

PG liposomes were formed by bath-sonication for 30 minutes at room temperature. LPS (10 ng/ml) and different concentrations of PG were added to monolayer cultures of differentiated U937 cells (left panel) or rat alveolar macrophages (right panel). Media TNF-α measurements were performed 6 hours after stimulation. Media NO measurements were performed 24 h after stimulation. LPS stimulation without PG was set at 100%. The molecular species of PG shown on the graph are: 16:0/16:0, dipalmitoyl-phosphatidylglycerol; 18:0/18:0, distearoyl-phosphatidylglycerol, 16:0/18:1, palmitoyl-oleoyl-phosphatidylglycerol (POPG); and 18:1/18:1, dioleoyl-phosphatidylglycerol. The data shown are the means±S.E. from three separate experiments with duplicate samples in each experiment. The results are presented in FIG. 30.

Example 7

This example demonstrates that POPG, DMPG and PI antagonize the effects of LPS on primary human alveolar macrophages.

Figure 31:
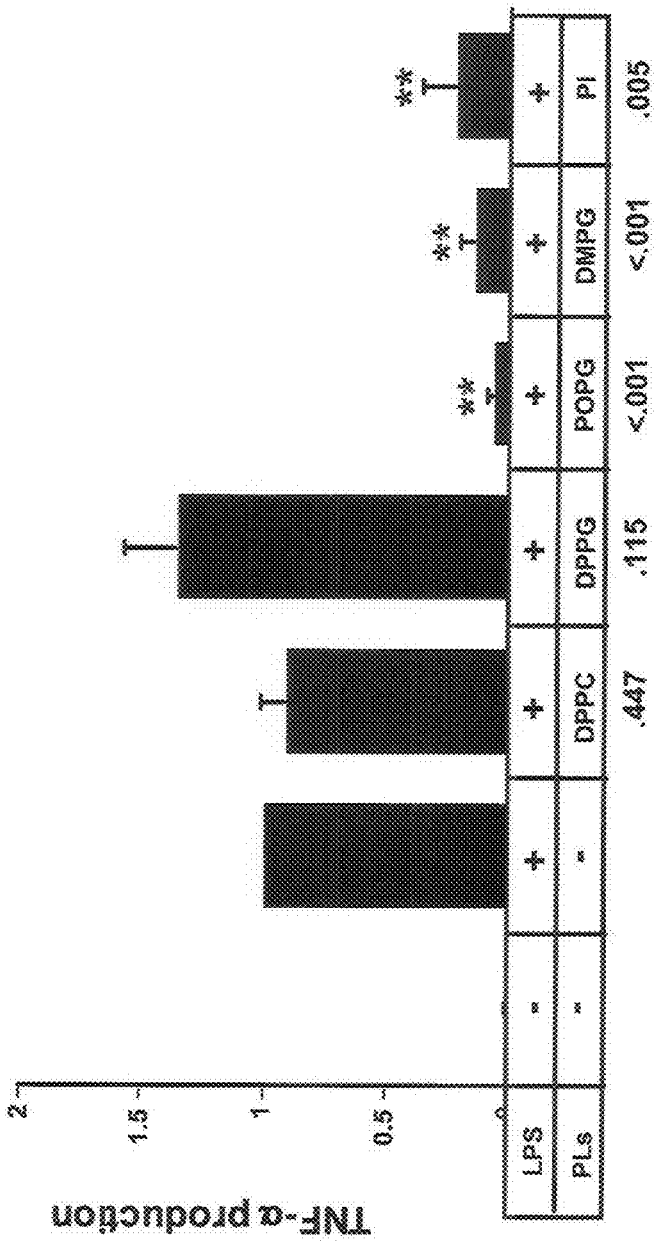
FIG. 31 shows that POPG, DMPG and PI antagonize the effects of LPS on primary human alveolar macrophages.

Human alveolar macrophages were isolated from healthy volunteer BALF and plated onto a 96-well plate. Two days after plating, 10 ng/ml of LPS and 20 μg/ml of phospholipids (POPG, DMPG and PI) were added to monolayer cultures of human alveolar macrophages. 6 h after stimulation, media were collected and TNF-α production was determined by ELISA. LPS stimulation without phospholipid was set at 100%. The data shown in FIG. 31 are the means±S.E. from three separate experiments with duplicate samples in each experiment. The average TNF-α secretion after LPS stimulation was 30.7+15.1 ng/ml. Significance—**:p<0.01, when compared with LPS stimulation in the absence of POPG.

Example 8

This example demonstrates that POPG inhibits activation of RAW 264.7 macrophages by multiple TLRs.

Figure 32:
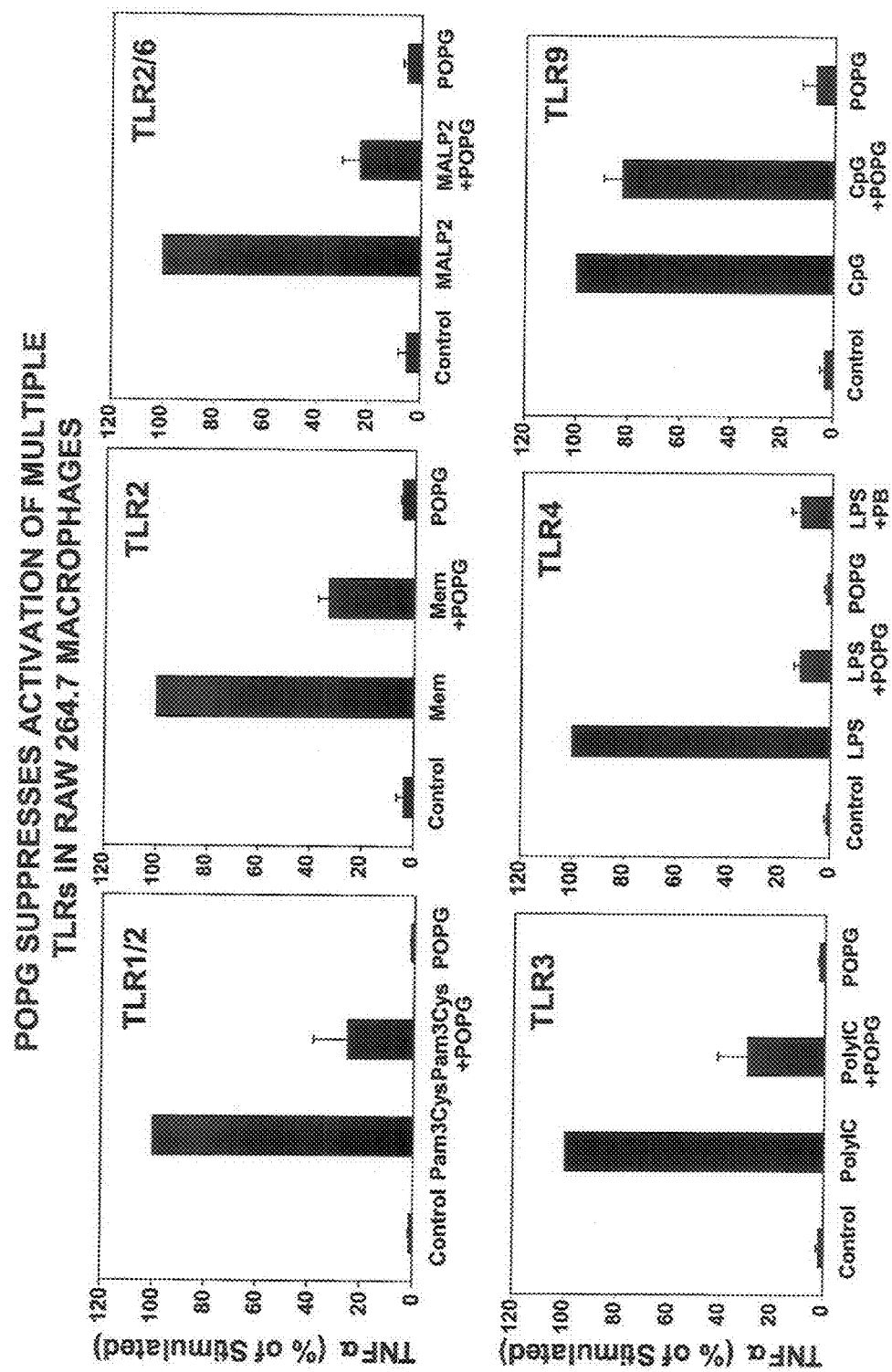
FIG. 32 shows that POPG inhibits activation of RAW 264.7 macrophages by multiple TLRs.

Monolayers of RAW 264.7 cells were stimulated with the TLR½ agonist, Pam3CysK4 (1 ug/ml); the TLR2 agonist, mycoplasma membrane (0.1 ug/ml protein); the TLR⅔ agonist MALP2 (0.1 ng/ml); the TLR3 agonist, polyI:C (100 ug/ml); the TLR4 agonist, LPS (10 ng/ml); and the TLR9 agonist, oligo CpG (10 ug/ml) for 5 hours in either the absence or presence of 200 ug/ml POPG, as indicated. The control consists of untreated cells. Cultures treated only with POPG and no agonists, are also shown in each panel. Cells treated with LPS and polymyxin B (1000 units) are also shown in the TLR4 panel. Following treatment, the medium was harvested, centrifuged to remove non-adherent cells and processed for detection of sereted TNFα by ELISA. Values shown in FIG. 32 are averages±SE for 3 independent experiments.

Example 9

This example demonstrates that POPG inhibits activation of primary bronchial epithelial cells by multiple TLRs.

Figure 33:
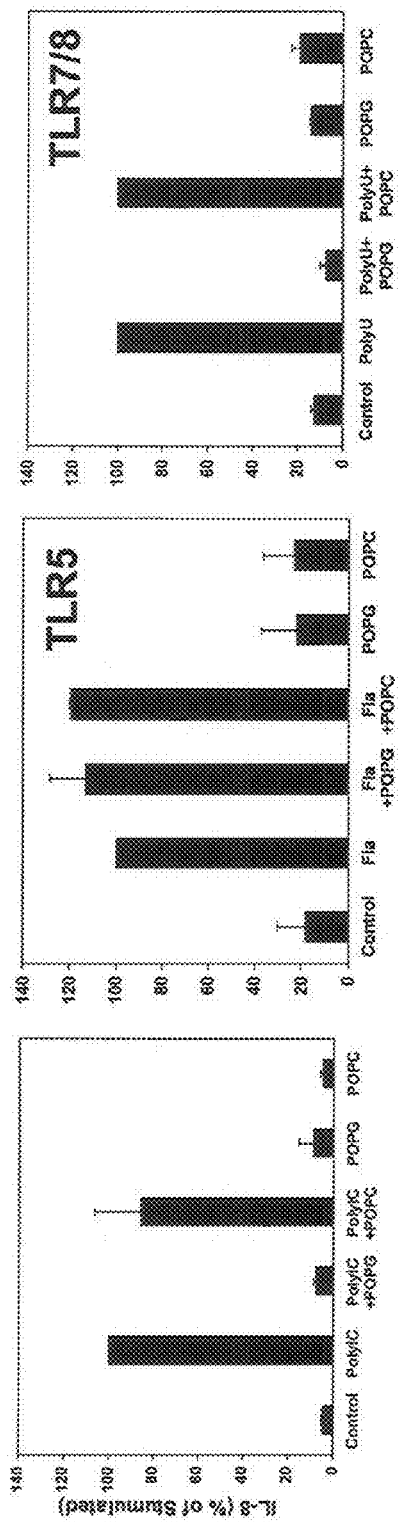
FIG. 33 shows that POPG inhibits activation of primary bronchial epithelial cells by multiple TLRs.

Monolayers of normal human bronchial epithelial cells were stimulated with the TLR3 agonist, polyI:C (0.1 ug/ml); the TLR5 agonist, flagellin (10 ng/ml) and the TLR⅞ agonist polyU (100 ug/ml) for 24 h in either the absence or presence of 200 ug/ml POPG, or POPC as indicated. Cultures were also treated with POPG or POPC alone, as additional controls. After 24 h the medium was harvested and centrifuged to remove non-adherent cells, and processed to detect IL-8 production by ELISA. Values shown in FIG. 33 are averages±SE for 3 independent experiments.

Example 10

This example demonstrates that POPG suppresses inflammatory cytokine production in BEAS2B, and normal human bronchial epithelial cells; induced by Respiratory Syncytial Virus (RSV).

Figure 34:
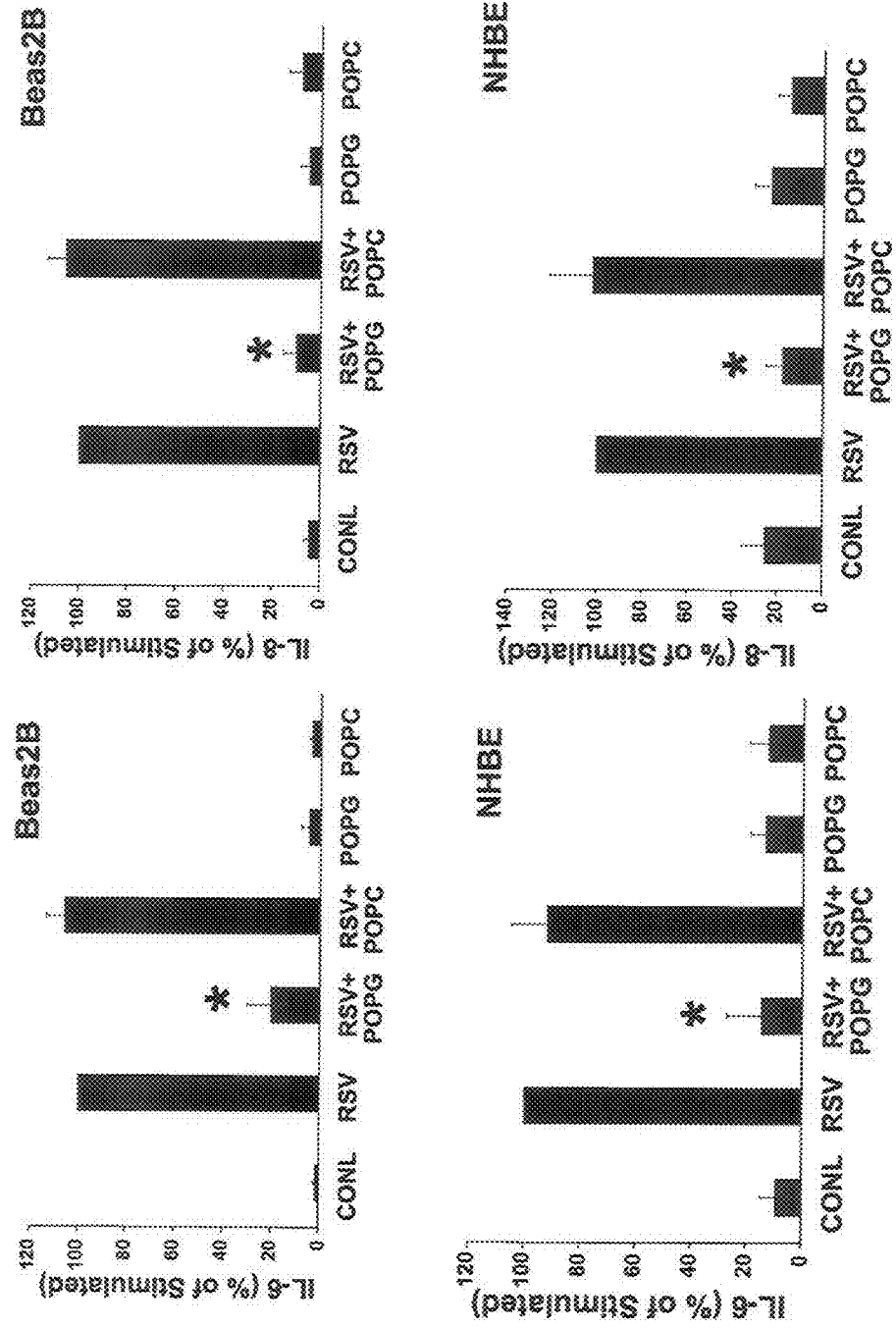
FIG. 34 shows that that POPG suppresses inflammatory cytokine production in BEAS2B, and normal human bronchial epithelial cells, induced by Respiratory Syncytial Virus (RSV).

Monolayers of the BEAS2B cell line, or normal human bronchial epithelial cells (NHBE), were either untreated (CONL), or infected with RSV at a multiplicity of 0.5-1; in either the presence or absence of 200 ug/ml POPG and POPC, as indicated. Additional control conditions exposed the monolayers to POPG, or POPC alone, as indicated. At 48 h after the initiation of infection, the medium was harvested and centrifuged to remove non-adherent cells. The supernatants were processed for detection of either IL-6, or IL-8 by ELISA. Values shown in FIG. 34 are means±SE for three independent experiments.

Example 11

This example demonstrates that POPG prevents the killing of BEAS2B cells by RSV.

Figure 35:
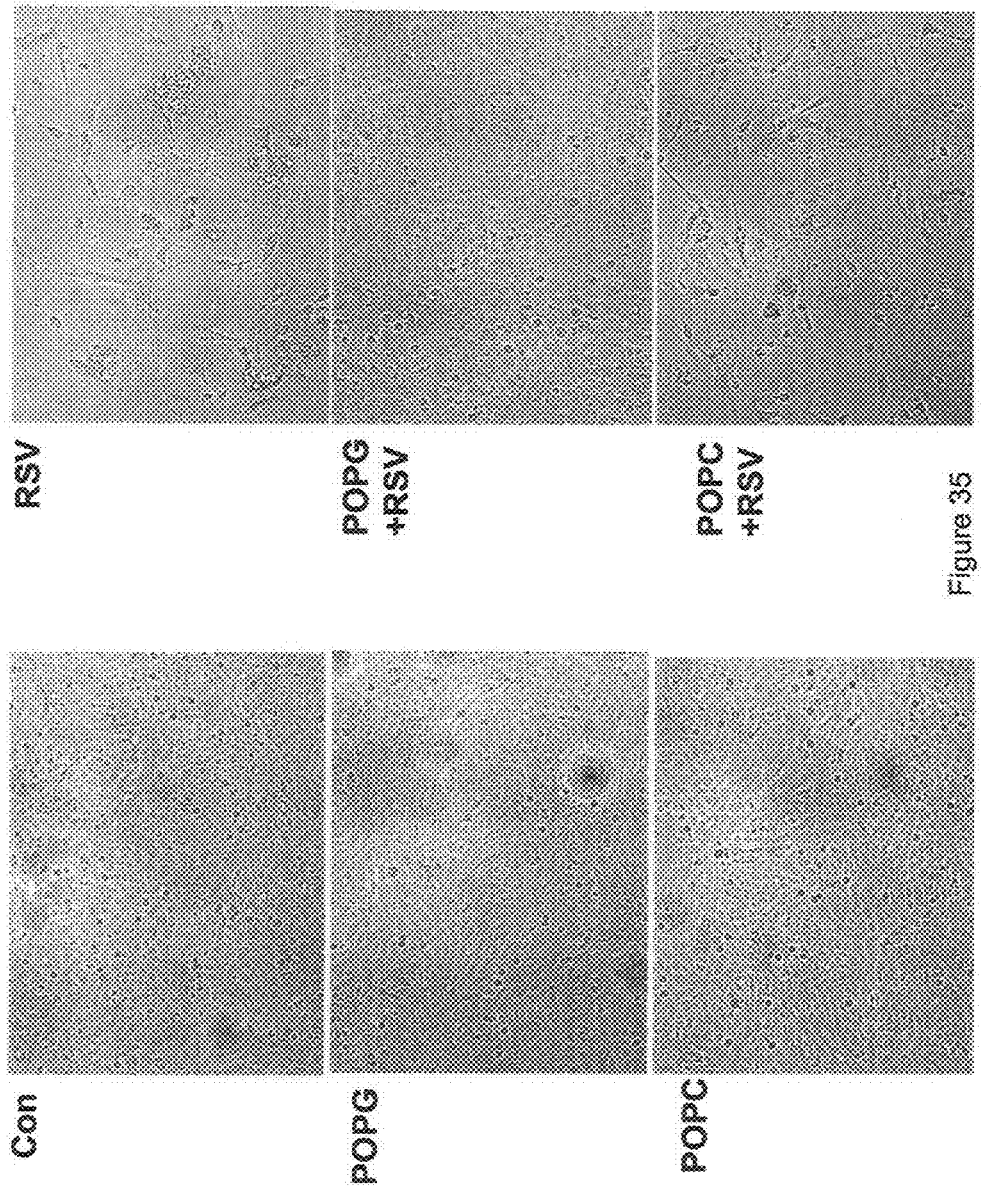
FIG. 35 shows that POPG prevents the killing of BEAS2B cells by RSV.

Monolayers of BEAS2B cells were infected with RSV at a multiplicity of 0.5-1, in either the presence or absence of 200 ug/ml POPG, or 200 ug/ml POPC, as indicated. After 72 h the cultures were subjected to photomicrography at a magnification of 200×, as shown in FIG. 35.

Example 12

This example demonstrates that POPG prevents the killing of normal human bronchial epithelial cells by RSV.

Figure 36:
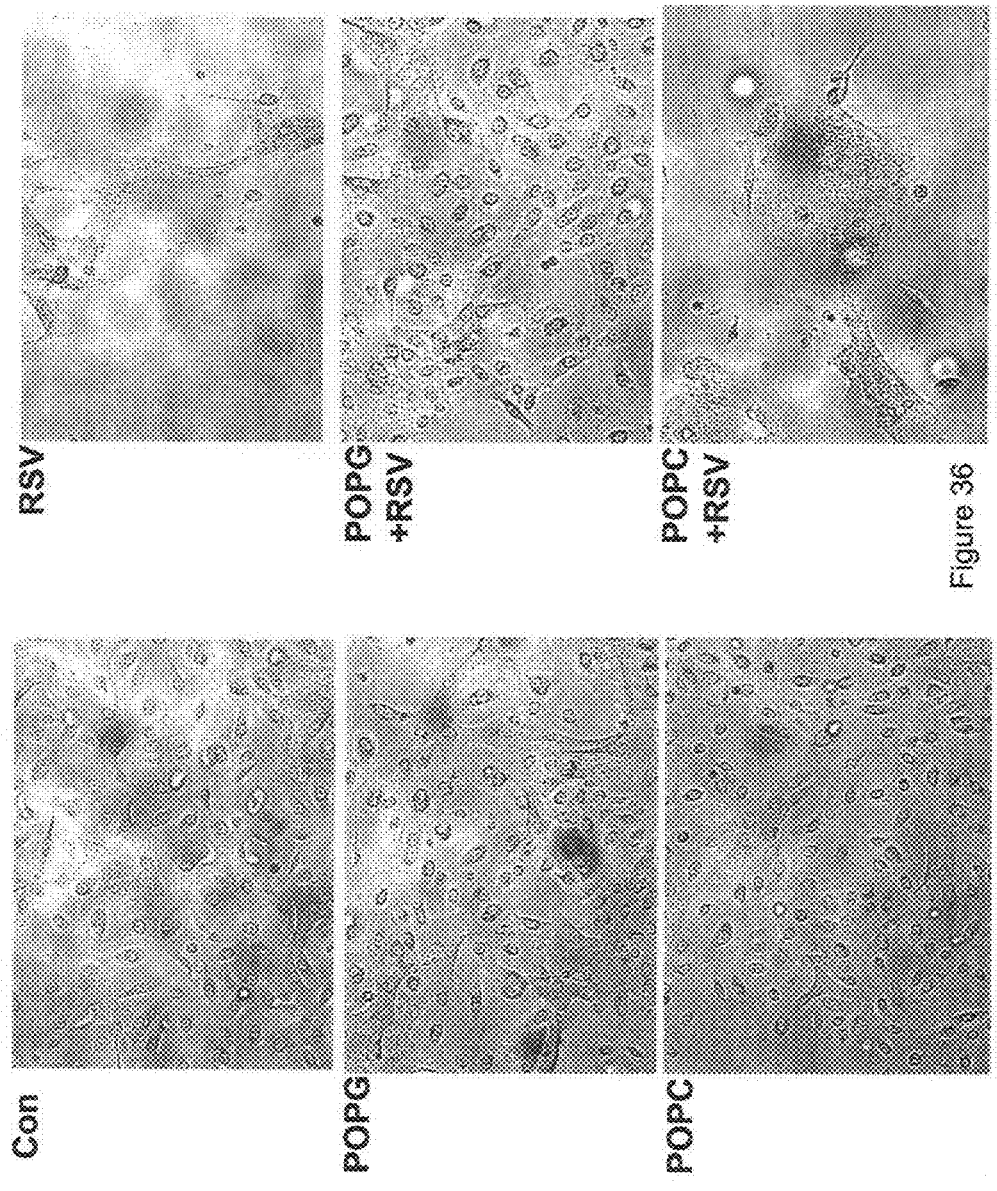
FIG. 36 shows that POPG prevents the killing of normal human bronchial epithelial cells by RSV.

Monolayers of normal human bronchial epithelial cells were infected with RSV at a multiplicity of 0.5-1, in either the presence or absence of 200 ug/ml POPG, or 200 ug/ml POPC, as indicated. After 72 h the cultures were subjected to photomicrography at a magnification of 200×, as shown in FIG. 36.

Example 13

This example demonstrates that POPG binds RSV with high affinity and specificity, and inhibits IL-8 production from epithelial cells in a concentration-dependent manner.

Solid phase phospholipids (10 ug) were adsorbed to microtiter wells by evaporation of ethanol solvent. The wells were blocked with albumin and exposed to varying concentrations of RSV as shown in the left panel of FIG. 37. The wells were washed 3 times with phosphate buffered saline and the bound virus was detected by ELISA using polyclonal rabbit anti-RSV.

Cultures of BEAS2B cells were treated with RSV at a multiplicity of 0.5 in either the absence or the presence of varying concentrations of POPG as indicated. After 48 hours, the culture supernatants were harvested and centrifuged, and the IL-8 production was quantified by ELISA. IL-8 levels are shown in the right panel of FIG. 37.

Example 14

This example demonstrates that POPG blocks the binding of RSV to epithelial cells.

Figure 38:
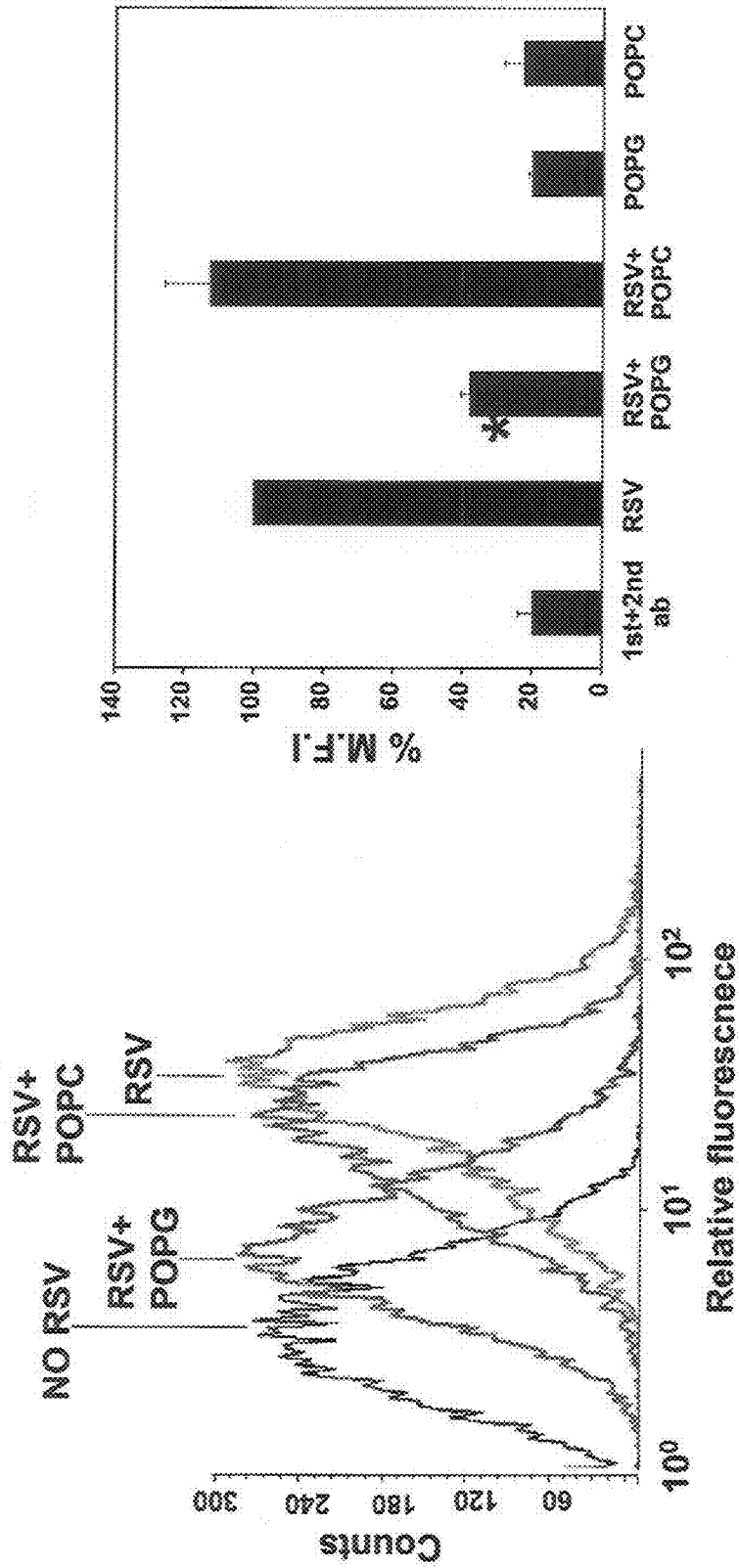
FIG. 38 shows that POPG blocks the binding of RSV to epithelial cells.

Suspensions of 3×10$^5$ Hep2 cells were treated with RSV at a multiplicity of 50, at 37 C for 10 min, in either the absence of lipid, or the presence of 200 ug/ml POPG, or POPC, as indicated. The cells were next shifted to 0 C and washed 3 times with PBS. The cells were then incubated with monoclonal mouse anti-RSV antibody for 1 h at 0 C in PBS containing 5% BSA. The unbound antibody was removed by washing the cells 3 times with PBS, 5% BSA. Next, the cells were incubated with phycoerythrin conjugated rabbit anti-mouse antibody in PBS, 5% BSA for 2 h. Following this incubation the cells were washed 3 times with PBS and fixed overnight with 1% buffered formalin. The fixed cell preparation was washed 3 times with PBS and subjected to FACScan analysis as shown in the left panel of FIG. 38. The summary of the mean fluorescence intensity (MFI) for all conditions is shown in the right panel of FIG. 38.

Example 15

This example demonstrates that POPG arrests the progression of RSV infection.

Figure 39:
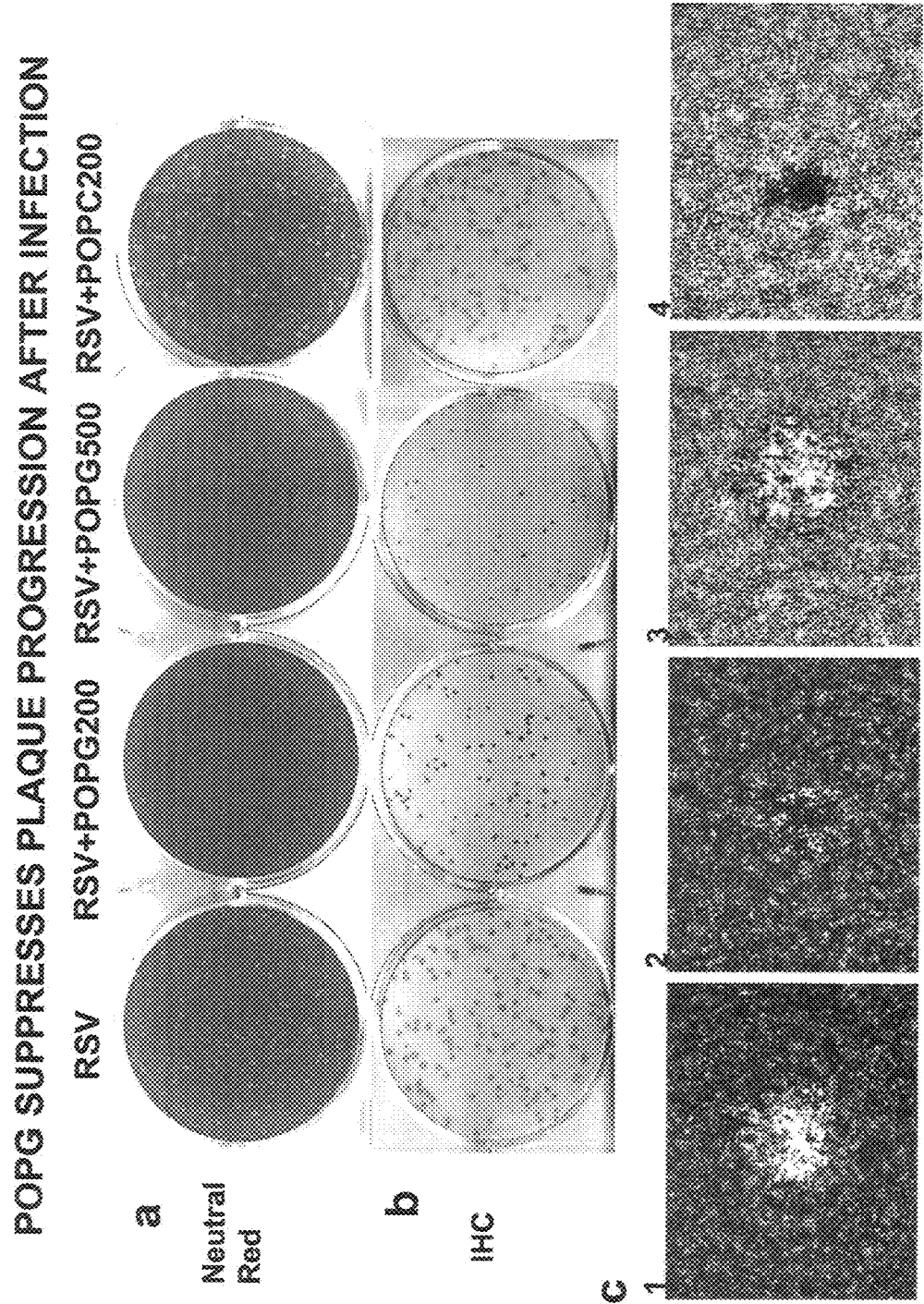
FIG. 39 shows that POPG arrests the progression of RSV infection.

Monolayers of Hep2 cells were subjected to RSV infection at levels that produce ca 100 plaques per well in quantitative plaque assays. The virus was incubated with the cells for 5 hours prior to agar overlay. The agar overlays contained either no additions, or POPG (200-500 ug/ml) or POPC (500 ug/ml). Panel a of FIG. 39 shows the appearance of plaques after 5 days of culture following fixation and staining with neutral red. Panel b of FIG. 39 shows the appearance of the monolayers after fixation and staining with anti-RSV antibody (IHC), which reveals the presence of bullseye plaques as a result of RSV treatment alone, or RSV plus POPC treatment; and the appearance of indefinite minute plaques (not visible with neutral red staining), as a result of RSV plus POPG treatment. Panel c of FIG. 39 shows the magnification of individual plaques resulting from RSV (1), or RSV+POPG (2) treatment, and stained with neutral red; or RSV (3), or RSV+POPG (4) treatment stained by IHC.

Example 16

This example demonstrates the quantification of the arrest of plaque progression.

Figure 40:
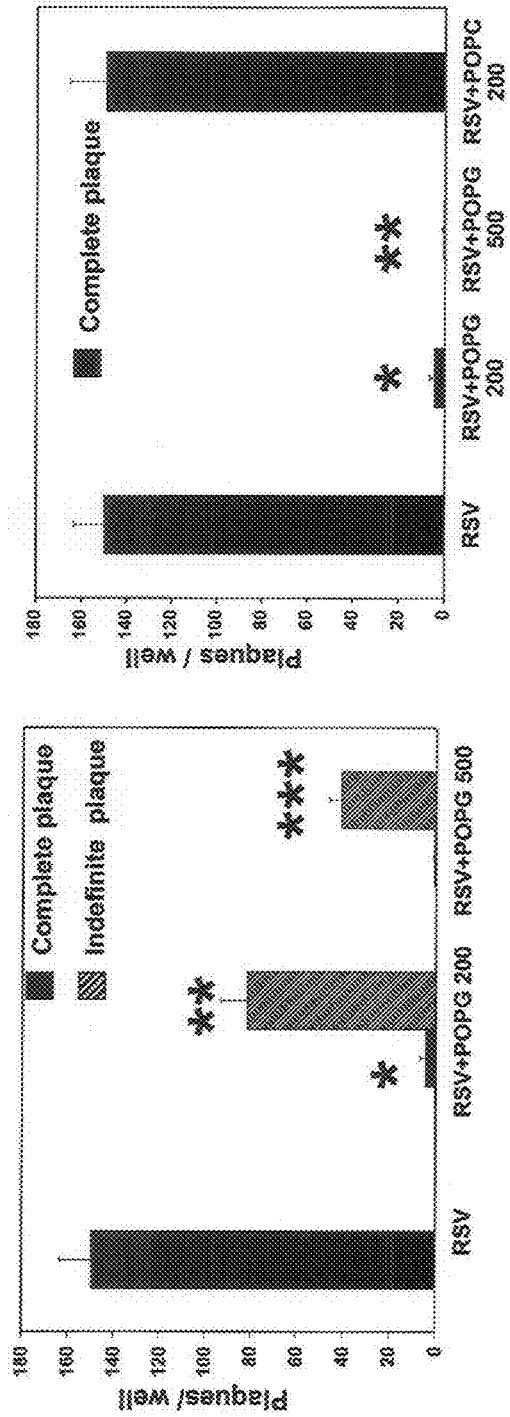
FIG. 40 shows the quantification of the arrest of plaque progression.

The effects of POPG upon plaque formation as shown in Panel a of FIG. 39 were quantified in 3 independent experiments and are presented in this figure. The left panel of FIG. 40 provides the numbers of definite, and minute indefinite plaques formed in the absence and presence of POPG (200-500 ug/ml) as indicated. The right panel of FIG. 40 provides the numbers of definite plaques observed in the absence and presence of either POPG or POPC (200-500 ug/ml) as indicated.

Example 17

This example demonstrates that POPG suppresses RSV infection in vivo.

Figure 41:
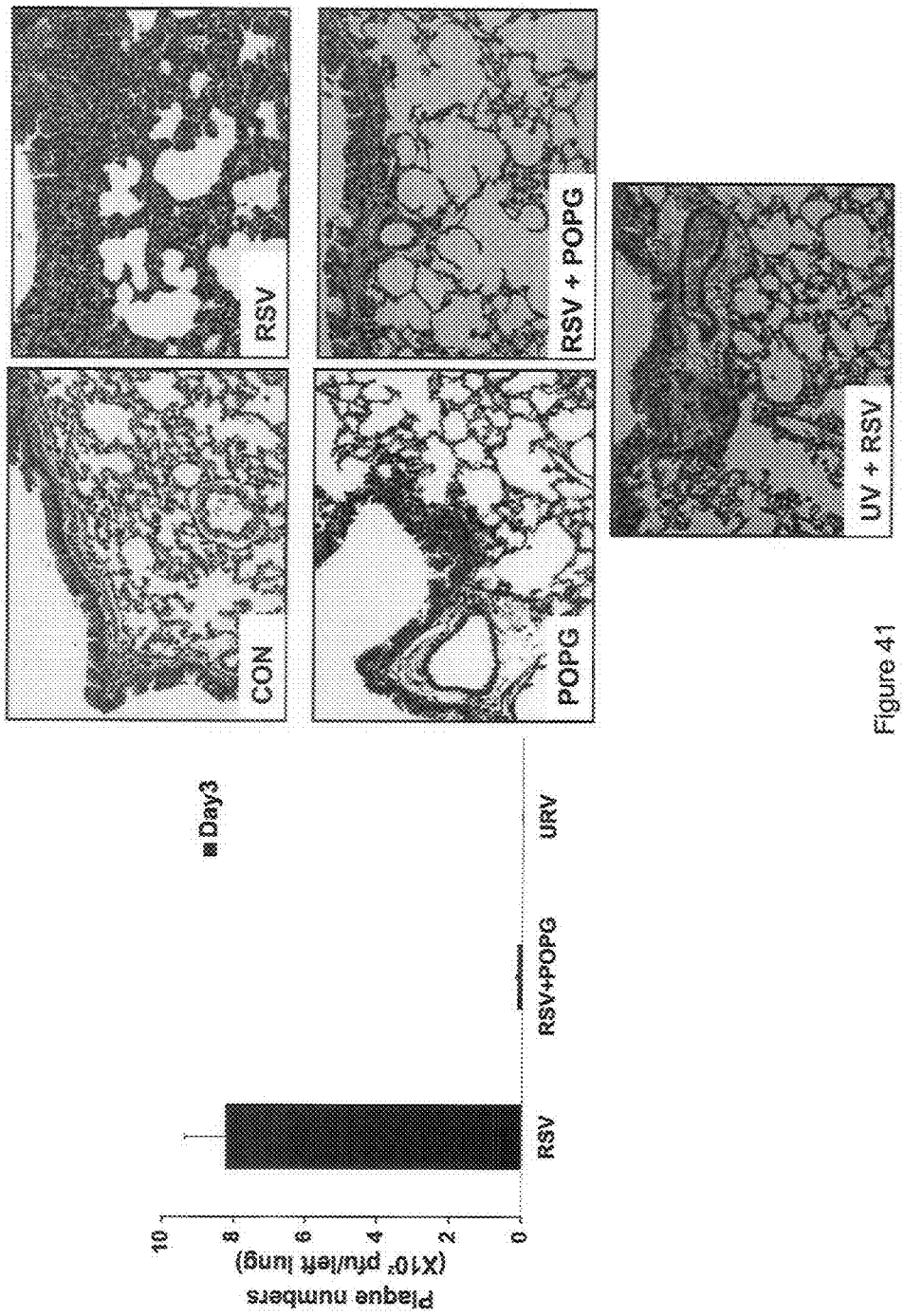
FIG. 41 shows that POPG suppresses RSV infection in vivo.

Groups of 8 mice were inoculated with 10$^7$ RSV in either the absence (RSV), or presence of 200 ug/ml POPG (RSV+POPG). Control experiments consisted of UV inactivated RSV (URV), or saline treatment (CON), or POPG treatment without virus (POPG). Three days after the inoculations, the animals were killed and the lungs harvested and processed for viral content by quantitative plaque assay (left panel of FIG. 41), and histopathology (right panel of FIG. 41)

Example 18

This example demonstrates that nanodisc POPG suppresses activation of TLR4 by LPS in macrophages and TLRs 2,3 and 6 in epithelial cells.

Figure 42:
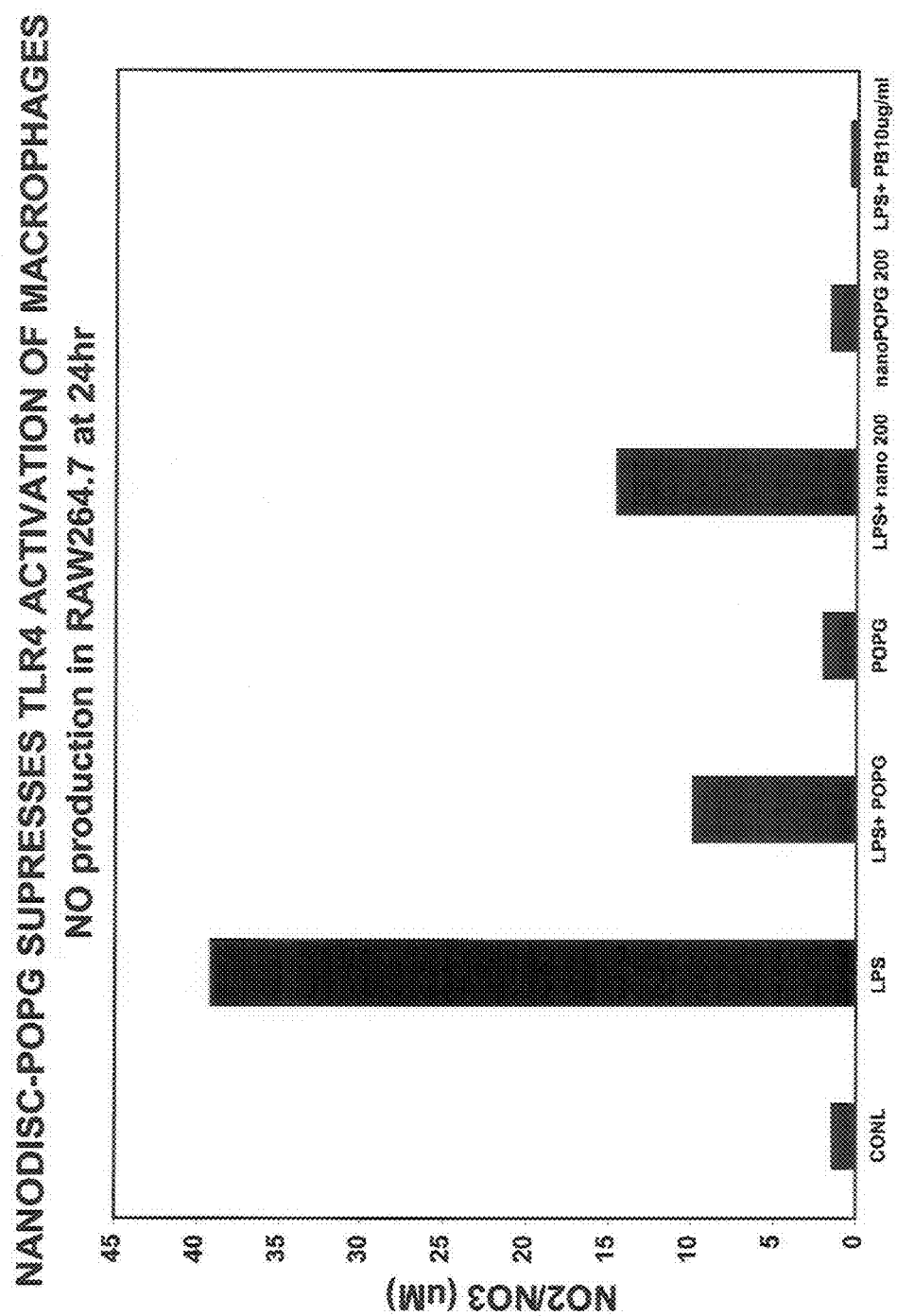
FIG. 42 shows that nanodisc POPG suppresses activation of TLR4 in macrophages.

Monolayers of RAW 264.7 cells were untreated (CONL) or challenged with 10 ng/ml LPS for 24 h (LPS), in the absence or presence of 200 ug/ml POPG in the form of liposomes (POPG) or as nanodiscs (nano). Additional control experiments included treatment of the cells with POPG or nanodisc POPG in the absence of LPS, or treatment with LPS and polymyxin B (PB), as indicated. At 24 h following the LPS challenge, the culture supernatants were harvested and the production of NO was measured using the Greiss reaction. Results are shown in FIG. 42.

Figure 43:
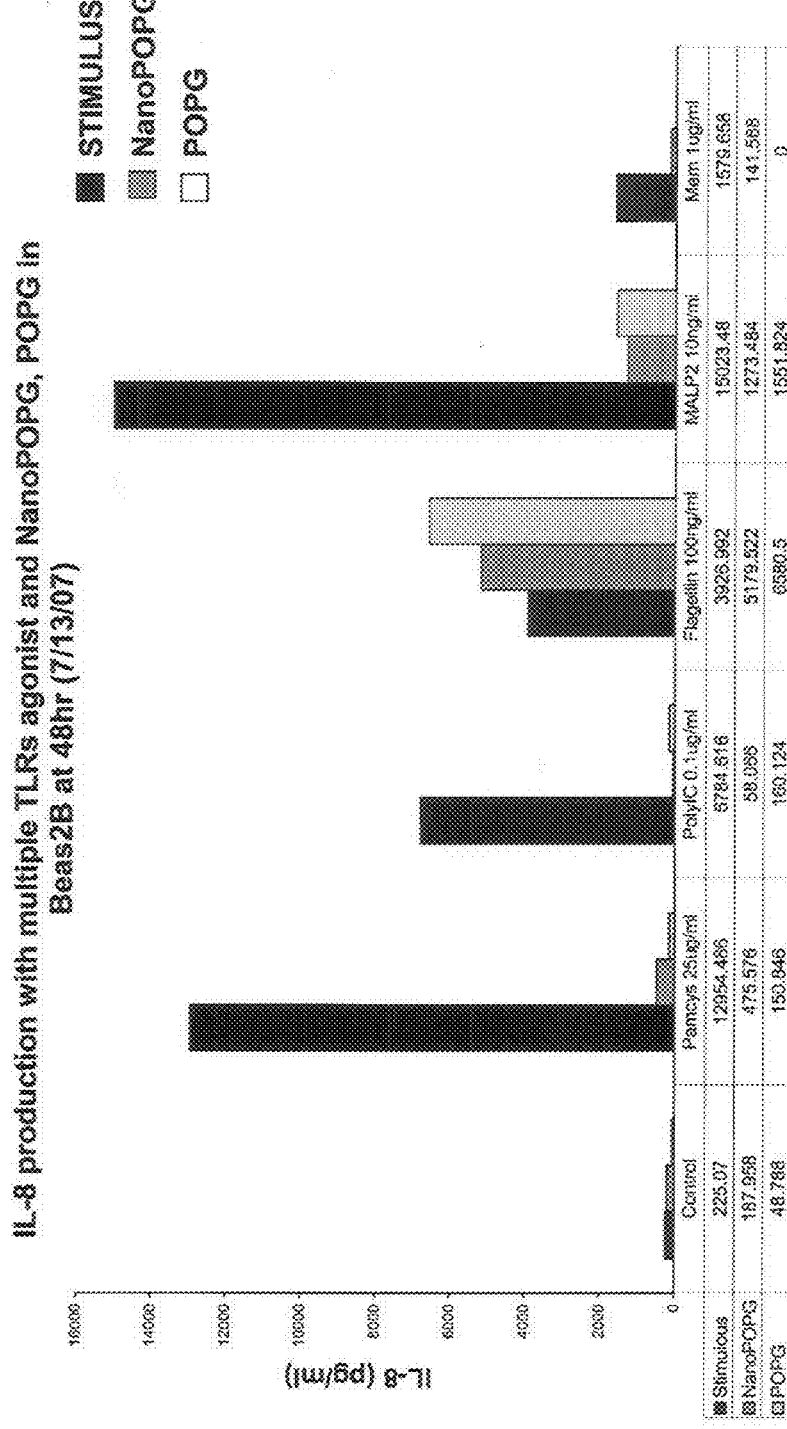
FIG. 43 shows that nanodisc POPG suppresses activation of TLRs 2,3 and 6 in epithelial cells.

Monolayers of BEAS2B cells were challenged with the TLR½ agonist, Pam3Cys (25 ug/ml); the TLR⅔ agonist MALP2 (10 ng/ml); the TLR2 agonist mycoplasma membrane (Mem) (1 ug/ml); the TLR3 agonist, poly I:C (0.1 ug/ml); and the TLR5 agonist, flagellin (100 ng/ml). For each agonist parallel incubations were performed containing 200 ug/ml POPG as liposomes, or 200 ug/ml POPG as nanodiscs as indicated. After 48 h, the culture supernatants were harvested and the secretion of IL-8 was measured using ELISA, as shown in FIG. 43. FIG. 43 also shows the negative results of nanodisc POPG upon TLR5 activation of the cells.

Example 19

This example demonstrates that nanodisc PG of various species is effective at preventing cytopathology in cells induced by RSV and that both liposome and nanodisc POPG inhibit plaque formation by RSV.

Figure 44:
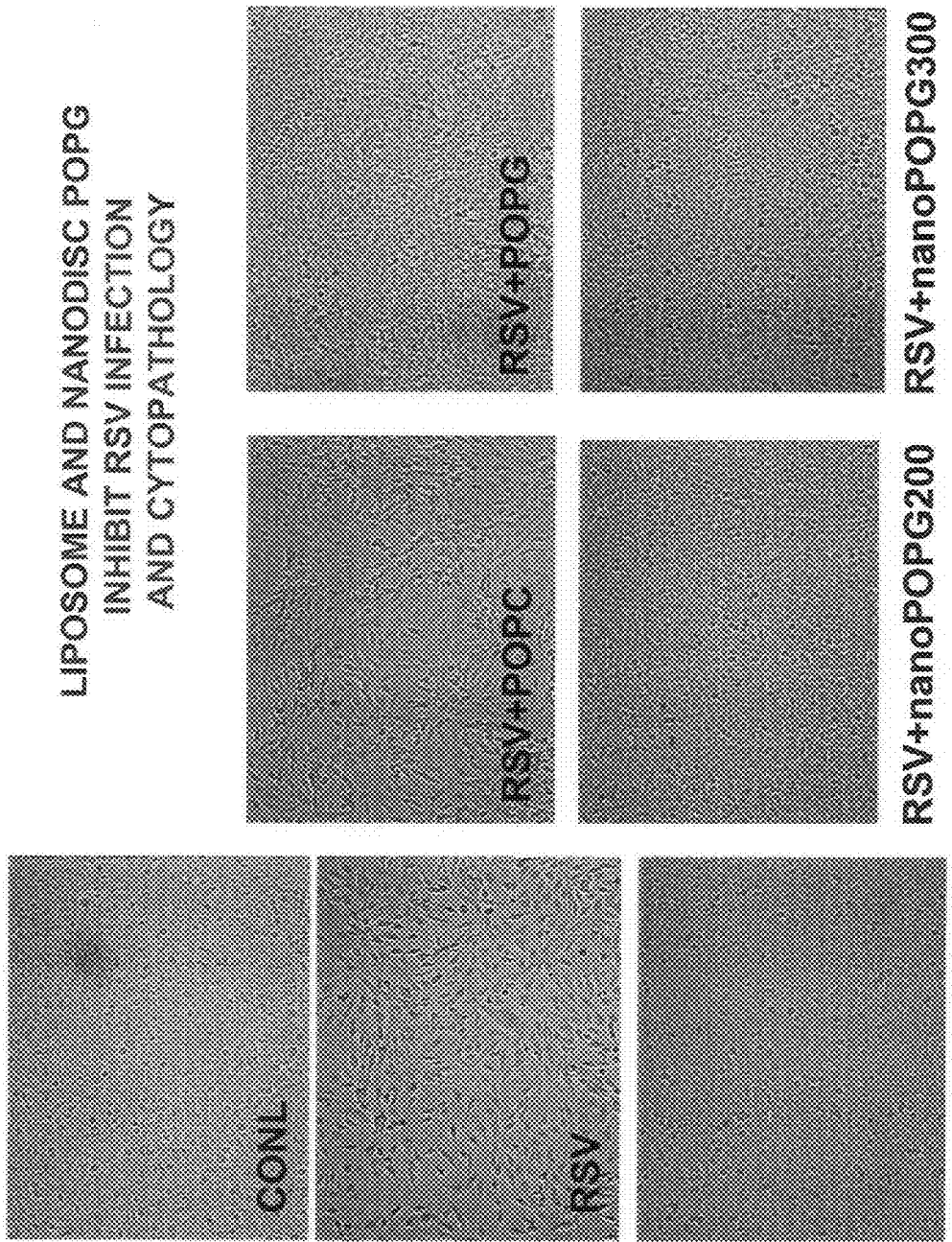
FIG. 44 shows that nanodisc PG of various species is effective at preventing cytopathology in cells induced by RSV.
Figure 45:
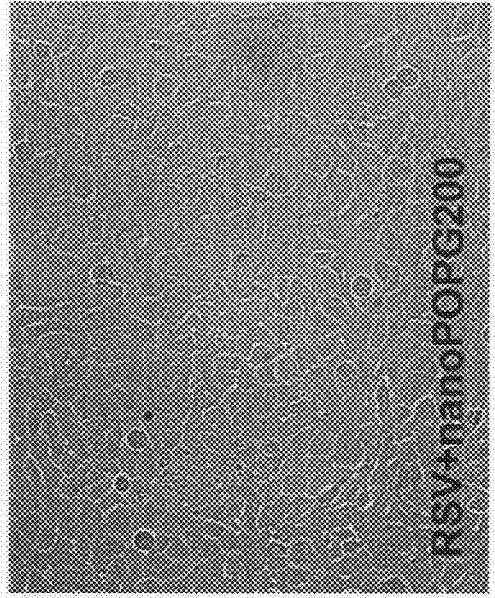
FIG. 45 shows that nanodisc PG of various species is effective at preventing cytopathology in cells induced by RSV.
Figure 45:
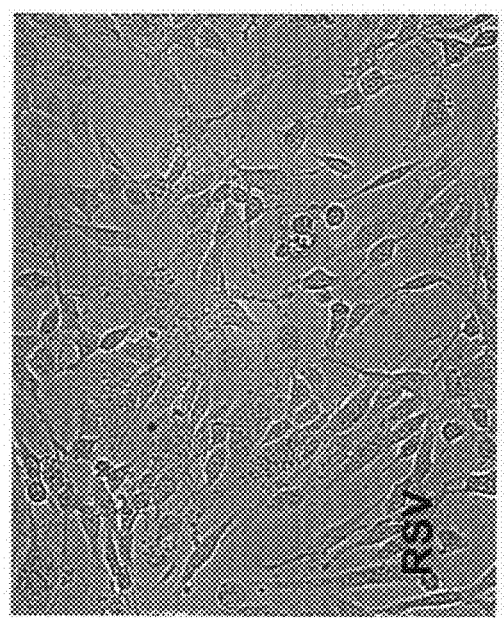
Figure 45:
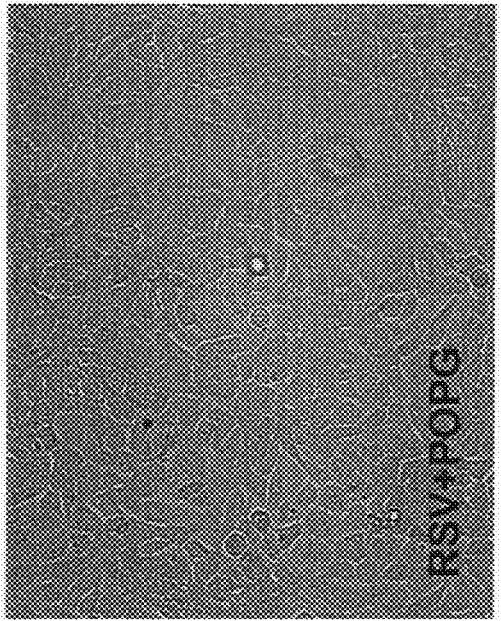

Monolayers of BEAS2B cells were either uninfected (CONL) or challenged with RSV at a multiplicity of 0.5/cell (RSV). Where indicated in the FIG. 44, RSV challenged cells were also treated with POPC (200 ug/ml) or POPG (200 ug/ml) liposomes; or POPG nanodiscs (nanoPOPG) at concentrations ranging from 100-300 ug/ml. At 72 h after infection, the cultures were examined by photomicrography at a magnification of 200×, as shown in FIG. 44. Selected panels and fields are also shown at 400× magnification in FIG. 45.

Figure 46:
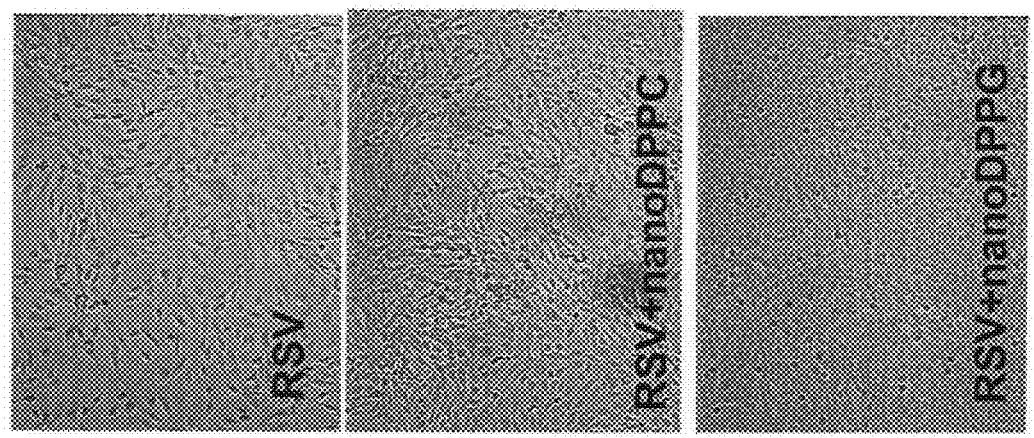
FIG. 46 shows that nanodisc PG of various species is effective at preventing cytopathology in cells induced by RSV.

To demonstrate that lipid inhibition of RSV infection is molecular class specific, monolayers of BEAS2B cells were either uninfected (CONL), or challenged with RSV at a multiplicity of 0.5/cell (RSV). Where indicated in FIG. 46, RSV challenged cells were also treated with nanodisc forms of dipalmitoyl-phosphatidylcholine (nanoDPPC), palmitoyl-oleoyl-phosphatidylcholine (nanoPOPC), or dioleoyl-phosphatidylcholine (nanoDOPC), dipalmitoyl-phosphatidylglycerol (nanoDPPG), dimyristoyl-phosphatidylglycerol (nanoDMPG), or dioleoyl-phosphatidylglycerol (nanoDOPG). At 72 h after infection, the cultures were examined by photomicrography at a magnification of 200×. As shown in FIG. 46, nanodisc PGs, but not PCs, disrupted RSV infection and cytopathology.

Figure 47:
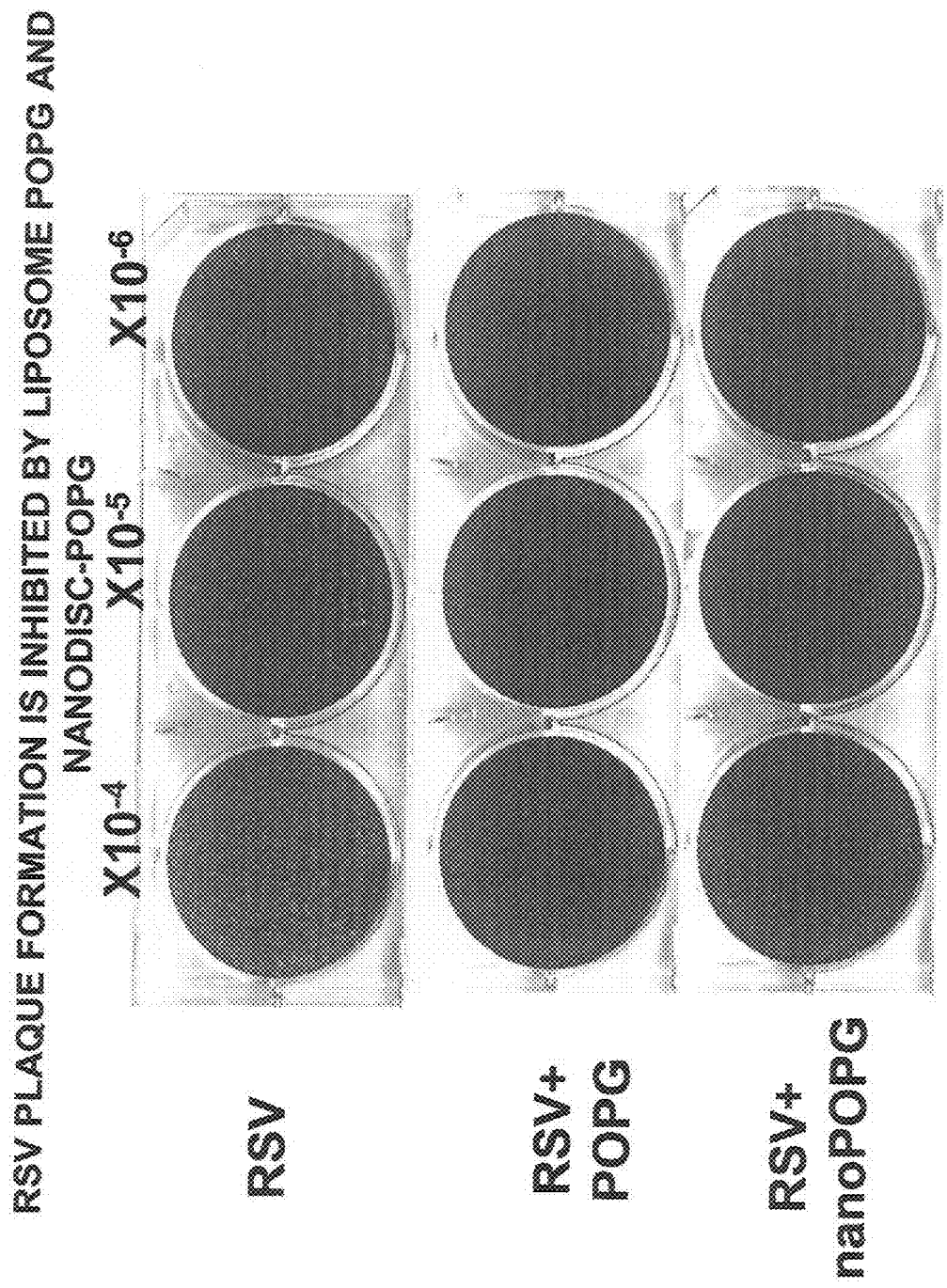
FIG. 47 shows that both liposome and nanodisc POPG inhibit plaque formation by RSV.

Quantitative viral plaque assays were performed in the absence (RSV) and the presence of liposomal and nanodisc lipids (RSV+POPG, and RSV+nano-POPG) as indicated in FIG. 47, using the indicated dilutions of virus from a stock of $2\times10^7$/ml RSV. Plaque formation progressed for 5 days, after which the cultures were fixed, and stained with neutral red. The results presented in FIG. 47 indicate that RSV plaque formation is inhibited by liposome POPG and nanodisc POPG.

Figure 48:
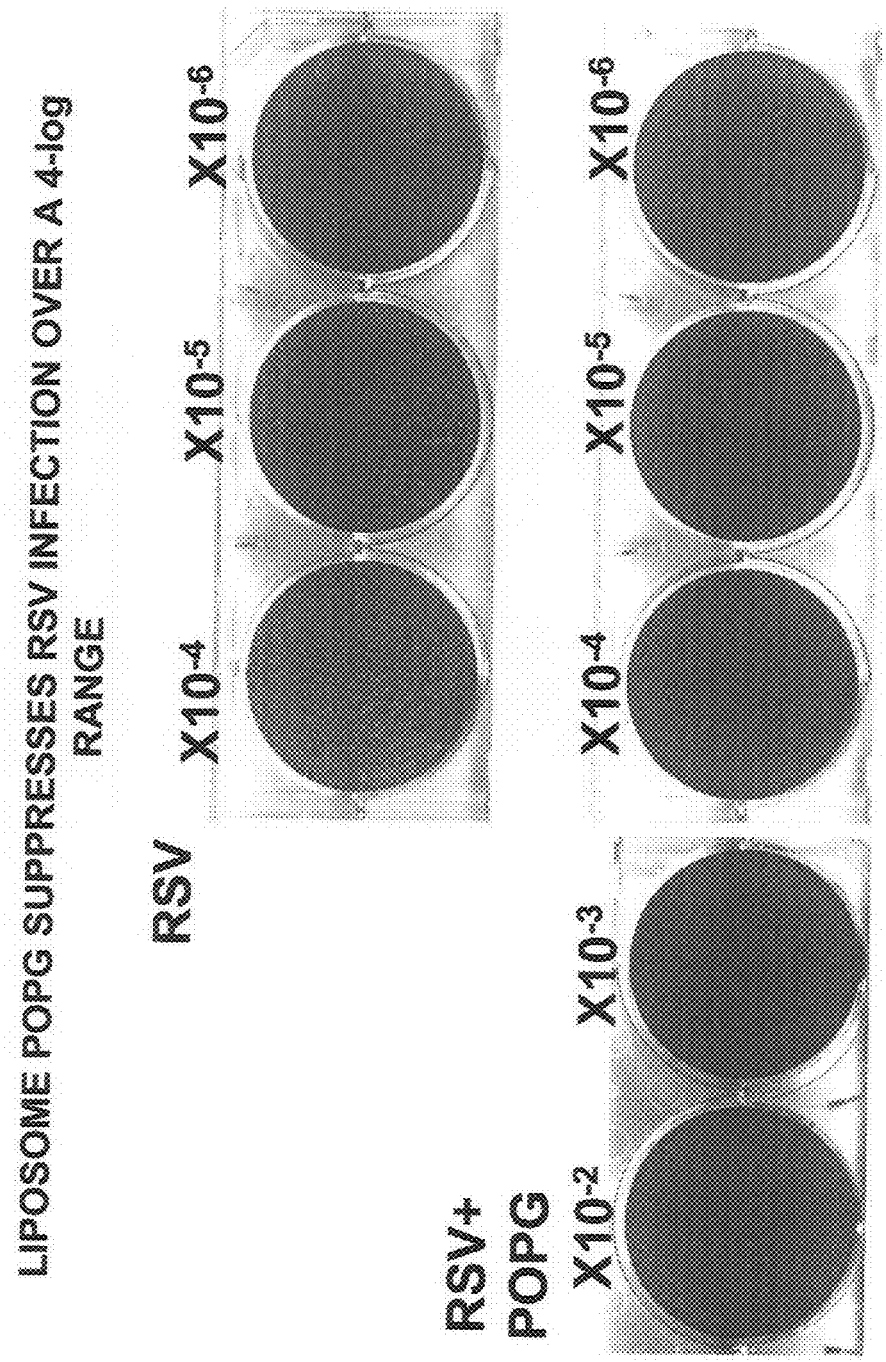
FIG. 48 shows that both liposome and nanodisc POPG inhibit plaque formation by RSV.

Quantitative viral plaques assays were performed in the absence (RSV) and presence of liposomal POPG (RSV+POPG). These samples are identical to those shown for RSV and liposome POPG in FIG. 47, but also show the inhibition of plaque formation by liposomal POPG, with much higher viral challenges ($10^{-2}$, $10^{-3}$ dilutions). The results presented in FIG. 48 indicate that liposome POPG suppresses plaque formation over a 4-log(10,000-fold) range.

Example 20

This example demonstrates that liposome POPG prevents the cytopathology and the inflammation—induced by influenza virus.

Figure 49:
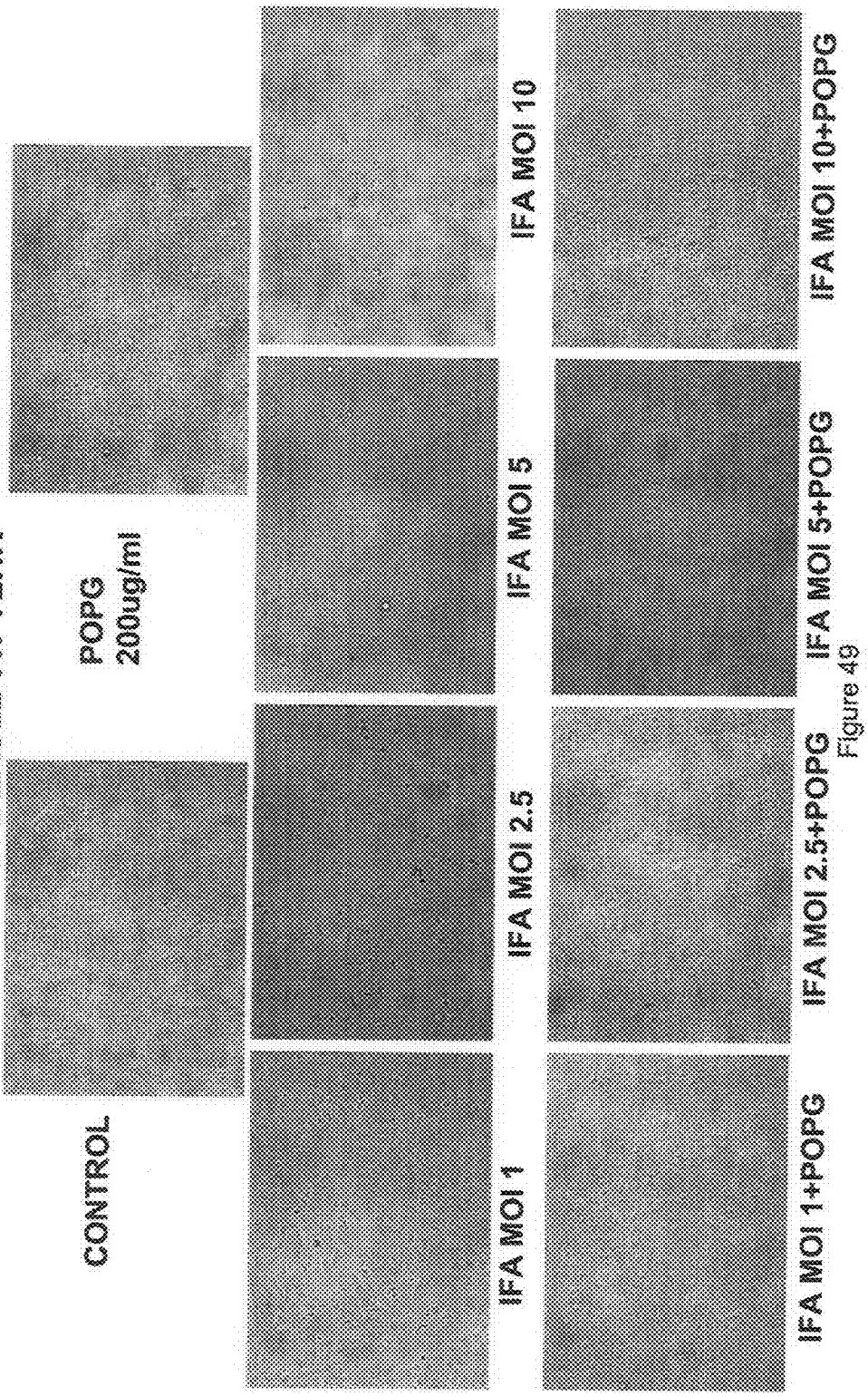
FIG. 49 shows that liposome POPG prevents the cytopathology and the inflammation induced by influenza virus.

Monolayers of BEAS2B cells were infected with influenza-A virus $H_3N_2$ (IFA), at the multiplicities of infection (moi) indicated, in either the absence or presence of 200 ug/ml POPG as indicated. The cells were examined for cytopathic effects and cell death at 72 after infection by photomicrography at 200× magnification, as shown in FIG. 49. These results indicate that POPG prevents cell death induced by influenza A infection in BEAS2B cells at 72 h.

Figure 50:
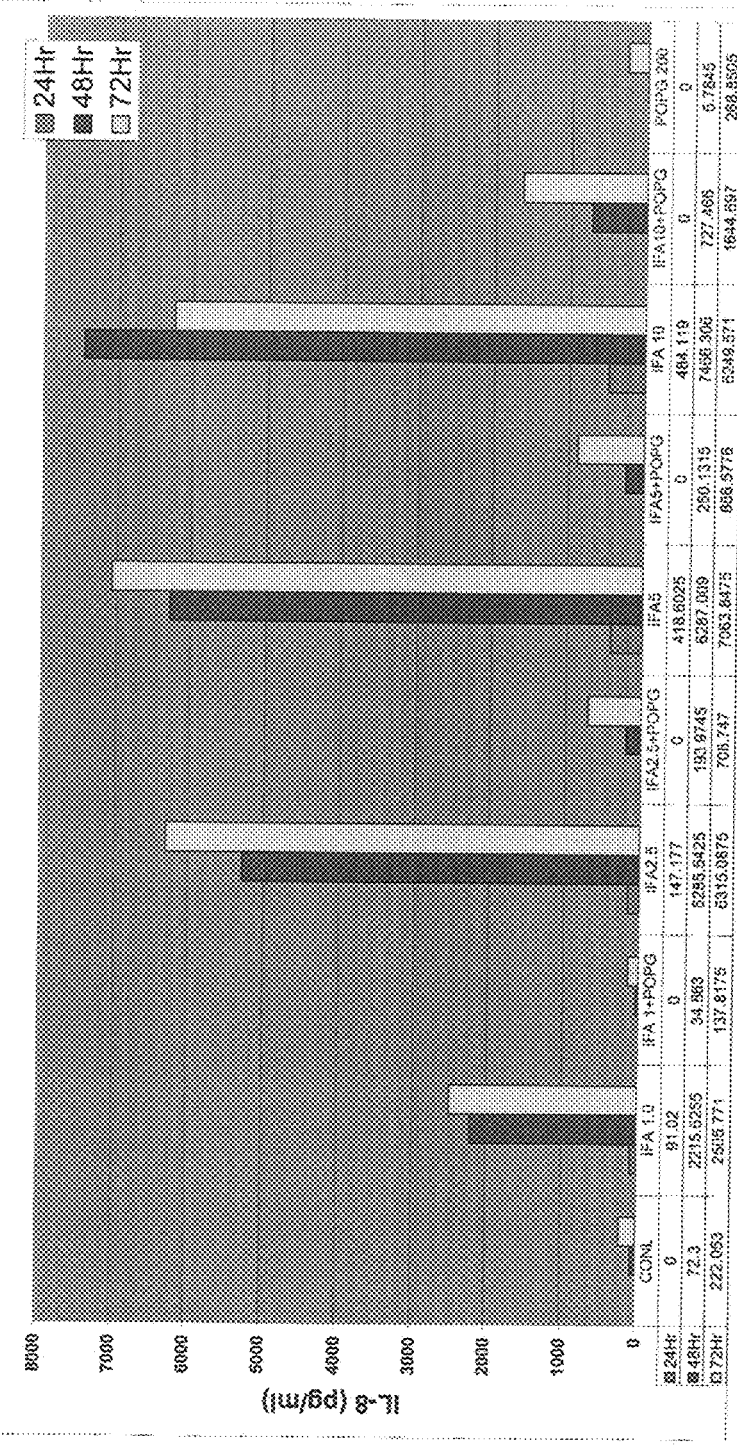
FIG. 50 shows that liposome POPG prevents the cytopathology and the inflammation induced by influenza virus.

Monolayers of BEAS2B cells were either untreated (CONL), or challenged with influenza-A virus $H_3N_2$ (IFA), at multiplicies ranging from 1-10 as indicated. Liposomes composed of 200 ug/ml POPG were added 30 minutes prior to viral infection (IFA+POPG), where indicated. An additional control condition in which cells were treated with POPG and no IFA was also conducted. The culture supernatants were harvested at 24, 48 and 72 h after infection and processed for IL-8 detection by ELISA, as shown in FIG. 50. The results indicate that POPG suppresses influenza-A induced IL-8 production in epithelial cells.

Each reference described or cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to inhibit inflammation associated with a toll-like receptor (TLR) selected from the group consisting of: TLR1, TLR2, TLR3, TLR6, TLR7, TLR8 and TLR10, comprising administering by inhalation to an individual who has, or is at risk of developing said inflammation, an amount of a pure preparation of an anionic lipid selected from the group consisting of unsaturated phosphatidylglycerol, and saturated short chain phosphatidylglycerol and derivatives thereof, wherein the amount of the anionic lipid is effective to inhibit said inflammation, and wherein the anionic lipid has the following characteristics:
a) has a hydrophobic portion;
b) has a negatively charged portion; and
c) has an uncharged, polar portion.

2. The method of claim 1, wherein the pure preparation of the anionic lipid is administered as a composition.

3. The method of claim 2, wherein the composition further comprises at least one additional agent for treating inflammation.

4. The method of claim 2, wherein the composition is administered to the respiratory tract of the individual.

5. The method of claim 2, wherein the composition is administered to the individual prior to any indication of inflammation.

6. The method of claim 2, wherein the composition is administered to individual subsequent to identification of a symptom of or confirmation of inflammation.

7. The method of claim 1, wherein the individual is a neonatal infant.

8. The method of claim 3, wherein the additional agent is an antibiotic.

* * * * *

UNITED STATES PATENT AND TRADEMARK OFFICE
CERTIFICATE OF CORRECTION

PATENT NO. : 9,861,649 B2
APPLICATION NO. : 14/318303
DATED : January 9, 2018
INVENTOR(S) : Voelker et al.

Page 1 of 1

It is certified that error appears in the above-identified patent and that said Letters Patent is hereby corrected as shown below:

On the Title Page

Item (12) "Voelker" should read -- Voelker, et al. --.

Item (72) Inventor is corrected to read:
-- Dennis R. Voelker, Greenwood Village CO (US);
Mari Numata-Nakamura, Kanagawa (JP) --.

Signed and Sealed this
Fourteenth Day of August, 2018

Andrei Iancu
*Director of the United States Patent and Trademark Office*